US010244755B2

(12) United States Patent
Fischer et al.

(10) Patent No.: US 10,244,755 B2
(45) **Date of Patent: *Apr. 2, 2019**

(54) FUNGICIDAL ACTIVE COMPOUND COMBINATIONS

(71) Applicant: Bayer CropScience Aktiengesellschaft, Monheim am Rhein (DE)

(72) Inventors: Reiner Fischer, Deutschland (DE); Peter Dahmen, Deutschland (DE); Ulrike Wachendorff-Neumann, Deutschland (DE)

(73) Assignee: BAYER CROPSCIENCE AKTIENGESELLSCHAFT, Monheim am Rhein (DE)

( * ) Notice: Subject to any disclaimer, the term of this patent is extended or adjusted under 35 U.S.C. 154(b) by 375 days.

This patent is subject to a terminal disclaimer.

(21) Appl. No.: 14/853,367

(22) Filed: Sep. 14, 2015

(65) Prior Publication Data

US 2016/0000076 A1 Jan. 7, 2016

Related U.S. Application Data

(63) Continuation of application No. 11/576,753, filed as application No. PCT/EP2005/010522 on Sep. 29, 2005, now Pat. No. 9,155,312.

(30) Foreign Application Priority Data

Oct. 8, 2004 (DE) ........................ 10 2004 049 041

(51) Int. Cl.

| | |
|---|---|
| ***A01N 43/64*** | (2006.01) |
| ***A01N 43/56*** | (2006.01) |
| ***A01N 43/653*** | (2006.01) |
| ***A01N 25/32*** | (2006.01) |
| ***A01N 61/00*** | (2006.01) |
| ***A01N 37/10*** | (2006.01) |
| ***A01N 43/28*** | (2006.01) |
| ***A01N 43/88*** | (2006.01) |
| *C07D 231/06* | (2006.01) |

(52) U.S. Cl.

CPC ............. *A01N 43/56* (2013.01); *A01N 25/32* (2013.01); *A01N 37/10* (2013.01); *A01N 43/28* (2013.01); *A01N 43/64* (2013.01); *A01N 43/653* (2013.01); *A01N 43/88* (2013.01); *A01N 61/00* (2013.01); *C07D 231/06* (2013.01)

(58) Field of Classification Search

CPC ...... A01N 43/653; A01N 43/64; A01N 25/32; A01N 43/56; C07D 231/06

USPC ........................................................ 514/383

See application file for complete search history.

(56) References Cited

U.S. PATENT DOCUMENTS

| | | | | |
|---|---|---|---|---|
| 5,599,828 | A | 2/1997 | Zeun et al. | |
| 5,789,430 | A | 8/1998 | Jautelat et al. | |
| 5,859,039 | A | 1/1999 | Jautelat et al. | |
| 5,998,455 | A | 12/1999 | Knauf-Beiter et al. | |
| 6,306,850 | B1 | 10/2001 | Dutzmann et al. | |
| 6,355,634 | B1 | 3/2002 | Isenring et al. | |
| 6,407,100 | B1 | 6/2002 | Isenring et al. | |
| 6,602,823 | B1 | 8/2003 | Röchling et al. | |
| 7,420,062 | B2 | 9/2008 | Fischer et al. | |
| 7,569,517 | B2 | 8/2009 | Fischer et al. | |
| 7,727,933 | B2 | 6/2010 | Fischer et al. | |
| 9,155,312 | B2 * | 10/2015 | Fischer .................. | A01N 43/56 |
| 2002/0173529 | A1 | 11/2002 | Dutzmann et al. | |
| 2005/0101639 | A1 | 5/2005 | Ammermann et al. | |
| 2005/0165076 | A1 | 7/2005 | Ammermann et al. | |
| 2006/0004070 | A1 | 1/2006 | Wachendorff-Neumann et al. | |
| 2006/0014738 | A1 | 1/2006 | Wachendorff-Neumann et al. | |
| 2006/0035942 | A1 | 2/2006 | Wachendorff-Neumann et al. | |
| 2007/0021303 | A1 | 1/2007 | Rosinger et al. | |
| 2007/0054804 | A1 | 3/2007 | Suty-Heinze | |
| 2007/0060579 | A1 | 3/2007 | Wachendorff-Neumann et al. | |
| 2007/0129252 | A1 | 6/2007 | Fischer et al. | |
| 2007/0225167 | A1 | 9/2007 | Fischer et al. | |
| 2008/0188371 | A1 | 8/2008 | Fischer et al. | |
| 2008/0221167 | A1 | 9/2008 | Fischer et al. | |
| 2008/0269051 | A1 | 10/2008 | Suty-Heinze et al. | |
| 2008/0269263 | A1 | 10/2008 | Dahmen et al. | |
| 2009/0069178 | A1 | 3/2009 | Suty-Heinze et al. | |
| 2009/0170918 | A1 | 7/2009 | Wolf | |
| 2009/0306109 | A1 | 12/2009 | Dutzmann et al. | |
| 2010/0240924 | A1 | 9/2010 | Fischer et al. | |
| 2011/0033433 | A1 | 2/2011 | Davies et al. | |
| 2011/0034496 | A1 | 2/2011 | Häuser-Hahn et al. | |
| 2011/0059991 | A1 | 3/2011 | Fischer et al. | |

FOREIGN PATENT DOCUMENTS

| | | | |
|---|---|---|---|
| AU | 2002337167 | B2 | 8/2008 |
| DE | 277 829 | A1 | 4/1990 |
| GB | 2 262 037 | A | 6/1993 |
| JP | 57-112311 | A2 | 7/1982 |

(Continued)

OTHER PUBLICATIONS

Bauer, T.A., et al., "Response of Selected Weed Species to Postemergence Imazethapyr and Bentazon," *Weed Tech.* 9:236-242, The Weed Science Society of America, United States (1995).

Blackshaw, R.E., "HOE-39866 Use in Chemical Fallow Systems," *Weed Tech.* 3:420-428, The Weed Science Society of America, United States (1989).

Blackshaw, R.E., "Synergistic Mixes of DPX-A7881 and Clopyralid in Canola (*Brassica napus*)," *Weed Tech.* 3:690-695, The Weed Science Society of America, United States (1989).

Blackshaw, R.E., et al., "Herbicide Combinations for Postemergent Weed Control in Safflower (*Carthamus tinctorius*)," *Weed Tech.* 4:97-104, The Weed Science Society of America, United States (1990).

Blouin, D.C., et al., "Analysis of Synergistic and Antagonistic Effects of Herbicides Using Nonlinear Mixed-Model Methodology," *Weed Tech.* 18:464-472, The Weed Science Society of America, United States (2004).

(Continued)

*Primary Examiner* — Mina Haghighatian
*Assistant Examiner* — Mei Ping Chui
(74) *Attorney, Agent, or Firm* — McBee Moore Woodward & Vanik IP, LLC

(57) ABSTRACT

Safeners for herbicides are suitable for increasing the microbicidal activity of fungicides.

15 Claims, No Drawings

(56) References Cited

FOREIGN PATENT DOCUMENTS

| | | | |
|---|---|---|---|
| JP | 60-123405 A2 | | 7/1985 |
| WO | WO2002337167 B2 | * | 5/2003 |
| WO | WO 2004/000022 A1 | | 12/2004 |

OTHER PUBLICATIONS

Bradley, P.R., et al., "Response of Sorghum (*Sorghum bicolor*) to Atrazine, Ammonium Sulfate, and Glyphosate," *Weed Tech.* 14:15-18, The Weed Science Society of America, United States (2000).
Buker, III, R.S., et al., "Confirmation and Control of a Paraquat-Tolerant Goosegrass (*Eleusine indica*) Biotype," *Weed Tech.* 16:309-313, The Weed Science Society of America, United States (2002).
Burke, I.C., et al., "CGA-362622 Antagonizes Annual Grass Control with Clethodim," *Weed Tech.* 16:749-754, The Weed Science Society of America, United States (2002).
Flint, J.L., et al., "Analyzing Herbicide Interactions, A Statistical Treatment of Colby's Method," *Weed Tech.* 2:304-309, The Weed Science Society of America, United States (1988).
Gillespie, G.R., and Nalewaja, J.D., "Wheat (*Triticum aestivum*) Response to Triallate Plus Chlorsulfuron," *Weed Tech.* 3:20-23, The Weed Science Society of America, United States (1989).
Green, J.M., et al., "Metribuzin and Chlorimuron Mixtures for Preemergence Broadleaf Weed Control in Soybeans, *Glycine max,"* *Weed Tech.* 2:355-363, The Weed Science Society of America, United States (1988).
Harker, N.K., and O'Sullivan, P.A., "Synergistic Mixtures of Sethoxydim and Fluazifop on Annual Grass Weeds," *Weed Tech.* 5:310-316, The Weed Science Society of America, United States (1991).
Kent, L.M., et al., "Effect of Ammonium Sulfate, Imazapyr, and Environment on the Phytotoxicity of Imazethapyr," *Weed Tech.* 5:202-205, The Weed Science Society of America, United States (1991).
Kotoula-Syka, E., et al., "Interactions between SAN 582H and Selected Safeners on Grain Sorghum (*Sorghum bicolor*) and Corn (*Zea mays*)," *Weed Tech.* 10:299-304, The Weed Science Society of America, United States (1996).
Lanclos, D.Y., et al., "Glufosinate Tank-Mix Combinations in Glufosinate-Resistant Rice (*Oryza sativa*)," *Weed Tech.* 16:659-663, The Weed Science Society of America, United States (2002).
Norris, J.L., et al., "Weed Control from Herbicide Combinations with Three Formulations of Glyphosate," *Weed Tech.* 15:552-558, The Weed Science Society of America, United States (2001).
Novosel, K.M., et al., "Metolachlor Efficacy as Influenced by Three Acetolactate Synthase-Inhibiting Herbicides," *Weed Tech.* 12:248-253, The Weed Science Society of America, United States (1998).
Palmer, E.W., et al., "Broadleaf Weed Control in Soybean (*Glycine max*) with CGA-277476 and Four Postemergence Herbicides," *Weed Tech.* 14:617-623, The Weed Science Society of America, United States (2000).
Rummens, F.H.A., "An Improved Definition of Synergistic and Antagonistic Effects," *Weed Science* 23(1):4-6, The Weed Science Society of America, United States (1975).
Salzman, F.P., and Renner, K.A., "Response of Soybean Combinations of Clomazone, Metribuzin, Linuron, Alachlor, and Atrazine," *Weed Tech.* 6:922-929, The Weed Science Society of America, United States (1992).
Scott, R.C., et al., "Spray Adjuvant, Formulation, and Environmental Effects of Synergism from Post-Applied Tank Mixtures of SAN 582H with Fluazifop-P, Imazethapyr, and Sethoxydim," *Weed Tech.* 12:463-469, The Weed Science Society of America, United States (1998).
Shaw, D.R. and Arnold, J.C., "Weed Control from Herbicide Combinations with Glyphosate," *Weed Tech.* 16:1-6, The Weed Science Society of America, United States (2002).
Snipes, C.E., and Allen, R.L., "Interaction of Graminicides Applied in Combination with Pyrithiobac," *Weed Tech.* 10:889-892, The Weed Science Society of America, United States (1996).
Wehtje, G. and Walker, R.H., "Interaction of Glyphosate and 2,4-DB for the Control of Selected Morningglory (*Ipomoea* spp.) Species," *Weed Tech.* 11:152-156, The Weed Science Society of America, United States (1997).
Zhang, W., et al., "Fenoxaprop Interactions for Barnyardgrass (*Echinochloa crus-galli*) Control in Rice," *Weed Tech.* 19:293-297, The Weed Science Society of America, United States (2005).
International Search Report for International Patent Application No. PCT/EP2005/010522, European Patent Office, Rijswijk, Netherlands, dated Dec. 12, 2005.
Database Caplus Online, Chemical Abstracts Service, Columbus, Ohio, United States, Database accession No. 89:39538, Szerszen, J.B., et al., "Interactions between and among grain sorghum, sorghum downy mildew, and the seed herbicide antidotes Concep II, Concep, and Screen," *Phytopathology* (*Ecology and Epidemiology*) 78(12):1648-1655, The American Phytopathological Society, United States (Dec. 1998).
Database Caplus Online, Chemical Abstracts Service, Columbus, Ohio, United States, Database accession No. 1976:554950, Burchill, R. T. and Butt, D.J., "Apple spray programs used at East Malling to control scab and mildew," Report—East Mailing Research Station (Maidstone , England), pp. 161-165, CODEN: EMRSAV; ISSN: 0306-6398, United Kingdom (1974).
English language Abstract of the Japanese Patent Publication No. JP 57-112311 A2, Database Caplus Online, Chemical Abstracts Service, Columbus, Ohio, United States, Database accession No. 1982:522066, (1982).
English language Abstract of the Japanese Patent Publication No. JP 60-123405 A2, Database Caplus Online, Chemical Abstracts Service, Columbus, Ohio, United States, Database accession No. 1985:591458, (1985).
English language Abstract of the German Democratic Republic Patent Publication No. DD 277 829 A1, Database Caplus Online, Chemical Abstracts Service, Columbus, Ohio, United States, Database accession No. 1991:77036, (1990).
Tomlin, C., ed., *The Pesticide Manual*, 1242-1245, British Crop Protection Council, Farnham, UK (1997).
Opposition Proceeding in European Patent No. EP-B-1482798, Mar. 5, 2007-Nov. 9, 2009.
Prosecution History of European Patent Appl. No. 03735610.2 (European Counterpart of U.S. Appl. No. 10/518,742), Jul. 13, 2006-Sep. 25, 2009.
Partial English language translation of Prosecution History of European Patent Appl. No. 03735610.2, Jul. 13, 2006-Sep. 25, 2009.
Partial English language translation of Opposition Proceeding in European Patent No. EP-B-1482798, Feb. 26, 2007-Nov. 9, 2009.
"Azoxystrobin data sheet," Compendium of Pesticide Common Names, accessed at http://www.alanwood.net/pesticides/azoxystrobin.html, accessed on Apr. 8, 2009, 1 page.
"Kresoxim-methyl data sheet," Compendium of Pesticide Common Names, accessed at http://www.alanwood.net/pesticides/kresoxim-methyl.html, accessed on Apr. 8, 2009, 1 page.
"Metominostrobin data sheet," Compendium of Pesticide Common Names, accessed at http://www.alanwood.net/pesticides/metominostrobin.html, accessed on Apr. 8, 2009, 1 page.
Definition of "daimuron," alanwood.net, accessed at http://www.alanwood.net/pesticides/index_cn_frame.html , accessed on Nov. 1, 2010, 1 page.

* cited by examiner

FUNGICIDAL ACTIVE COMPOUND COMBINATIONS

The invention relates to the use of safeners for increasing the activity of fungicides, to combinations of fungicides and safeners and to their use for controlling unwanted microorganisms.

Numerous triazole derivatives, strobilurins, aniline derivatives, dicarboximides, carboxamides and other chemical compounds are already used for controlling unwanted microorganisms (see, for example, The Pesticide Manual, 13th Edition, Farnham, 2003).

However, since the environmental and economic requirements imposed on modern-day fungicides are continually increasing, with regard, for example, to the spectrum of action, toxicity, selectivity, application rate, formation of residues, and favourable preparability, and since, furthermore, there may be problems, for example, with resistances, a constant task is to develop new fungicides which in some areas at least have advantages over their known counterparts.

Surprisingly, it has now been found that safeners, i.e. compounds which improve the compatibility of crop plants with herbicides, are suitable for increasing the activity of fungicides against unwanted microorganisms, in particular phytopathogenic fungi.

This is even more surprising since generally safeners on their own have no effect on the unwanted microorganisms.

Accordingly, the invention provides the use of compounds which improve the compatibility of crop plants with herbicides (safeners) for increasing the microbicidal, in particular fungicidal, activity of fungicides.

The safener is generally a crop plant compatibility-improving compound from the following group of compounds (group 1):

4-dichloroacetyl-1-oxa-4-azaspiro[4.5]decane (AD-67, MON-4660), 1-dichloroacetylhexahydro-3,3,8a-trimethylpyrrolo[1,2-a]pyrimidin-6(2H)-one (dicyclonon, BAS-145138), 4-dichloroacetyl-3,4-dihydro-3-methyl-2H-1,4-benzoxazine (benoxacor), 1-methylhexyl 5-chloroquinolin-8-oxyacetate(cloquintocet-mexyl—cf. also related compounds in EP-A-0 086750, EP-A-0 094349, EP-A-0191736, EP-A-0492366), 3-(2-chlorobenzyl)-1-(1-methyl-1-phenylethyl)urea (cumyluron), α-(cyano-methoximino)phenylacetonitrile (cyometrinil), 2,4-dichlorophenoxyacetic acid (2,4-D), 4-(2,4-dichlorophenoxy)butyric acid (2,4-DB), 1-(1-methyl-1-phenylethyl)-3-(4-methylphenyl)urea (daimuron, dymron), 3,6-dichloro-2-methoxybenzoic acid (dicamba), S-1-methyl-1-phenylethyl piperidine-1-thiocarboxylate (dimepiperate), 2,2-dichloro-N-(2-oxo-2-(2-propenylamino)ethyl)-N-(2-propenyl)acetamide (DKA-24), 2,2-dichloro-N,N-di-2-propenylacetamide (dichlormid), 4,6-dichloro-2-phenylpyrimidine (fenclorim), ethyl 1-(2,4-dichlorophenyl)-5-trichloromethyl-1H-1,2,4-triazole-3-carboxylate (fenchlorazole-ethyl—cf. also related compounds in EP-A-01174562 and EP-A-346620), phenylmethyl 2-chloro 4-trifluoromethylthiazole-5-carboxylate (flurazole), 4-chloro-N-(1,3-dioxolan-2-ylmethoxy)-α-trifluoroacetophenone oxime (fluxofenim), 3-dichloroacetyl-5-(2-furanyl)-2,2-dimethyloxazolidine (furilazole, MON-13900), ethyl 4,5-dihydro-5,5-diphenyl-3-isoxazolecarboxylate (isoxadifen-ethyl—cf. also related compounds in WO-A-95/07897), 1-(ethoxycarbonyl)ethyl 3,6-dichloro-2-methoxybenzoate (lactidichlor), (4-chloro o-tolyloxy)acetic acid (MCPA), 2-(4-chloro-o-tolyloxy)propionic acid (mecoprop), diethyl 1-(2,4-dichlorophenyl)-4,5-dihydro-5-methyl-1H-pyrazole-3,5-dicarboxylate (mefenpyr-diethyl—cf. also related compounds in WO-A-91/07874), 2-dichloromethyl-2-methyl-1,3-dioxolane (MG-191), 2-propenyl-1-oxa-4-azaspira[4.5]decane 4-carbodithioate (MG-838), 1,8-naphthalic anhydride, α-(1,3-dioxolan-2-yl-methoximino)phenylacetonitrile (oxabetrinil), 2,2-dichloro-N-(1,3-dioxolan-2 ylmethyl)-N-(2-propenyl) acetamide (PPG-1292), 3-dichloroacetyl-2,2-dimethyloxazolidine (R-28725), 3-dichloroacetyl-2,2,5-trimethyloxazolidine (R-29148), 4-(4-chloro-o-tolyl) butyric acid, 4-(4-chloro-phenoxy)butyric acid, diphenylmethoxy acetic acid, methyl diphenylmethoxyacetate, ethyl diphenylmethoxyacetate, methyl 1-(2-chlorophenyl)-5-phenyl-1H-pyrazole-3-carboxylate, ethyl 1-(2,4-dichlorophenyl)-5-methyl-1H-pyrazole-3-carboxylate, ethyl 1-(2,4-dichlorophenyl)-5-isopropyl-1H-pyrazole-3-carboxylate, ethyl 1-(2,4-dichlorophenyl)-5-(1,1-dimethylethyl)-1H-pyrazole-3-carboxylate, ethyl 1-(2,4-dichlorophenyl)-5-phenyl-1H-pyrazole-3-carboxylate (cf. also related compounds in EP-A-0269806 and EP-A-0333131), ethyl 5-(2,4-dichlorobenzyl)-2-isoxazoline-3-carboxylate, ethyl 5-phenyl-2-isoxazoline-3-carboxylate, ethyl 5-(4-fluorophenyl)-5-phenyl-2-isoxazoline-3-carboxylate (cf. also related compounds in WO-A-91/08202), 1,3-dimethylbut-1-yl 5-chloroquinolin-8-oxyacetate, 4-allyloxybutyl 5-chloroquinolin-8-oxyacetate, 1-allyloxyprop-2-yl 5-chloroquinolin-8-oxyacetate, methyl 5-chloroquinoxalin-8-oxyacetate, ethyl 5-chloroquinolin-8-oxyacetate, allyl 5-chloroquinoxalin-8-oxyacetate, 2-oxoprop-1-yl 5-chloroquinolin-8-oxyacetate, diethyl 5-chloroquinolin-8-oxymalonate, diallyl 5-chloroquinoxalin-8-oxymalonate, diethyl 5-chloro-quinolin-8-oxymalonate (cf. also related compounds in EP-A-0582198), 4-carboxychroman-4-yl-acetic acid (AC-304415, cf. EP-A-0613618), 4-chlorophenoxyacetic acid, 3,3'-dimethyl-4-methoxybenzophenone, 1-bromo-4-chloromethylsulphonylbenzene, 1-[4-(N-2-methoxy-benzoylsulphamoyl)phenyl]-3-methylurea (alias N-(2-methoxybenzoyl)-4-[(methylamino-carbonyl)amino] benzenesulphonamide), 1-[4-(N-2-methoxybenzoylsulphamoyl)phenyl]-3,3-dimethylurea, 1-[4-(N-4,5-dimethylbenzoylsulphamoyl)phenyl]-3-methylurea, 1-[4-(N-naphthyl-sulphamoyl)phenyl]-3,3-dimethylurea, N-(2-methoxy-5-methylbenzoyl)-4-(cyclopropylamino-carbonyl)benzenesulphonamide, and/or one of the following compounds of the general formulae (I-a), (I-b), (I-c)

(I-a)

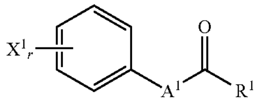

(I-b)

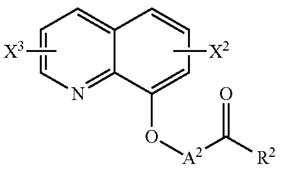

(I-c)

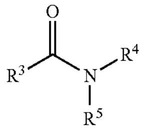

where r represents a number 0, 1, 2, 3, 4 or 5, $A^1$ represents one of the divalent heterocyclic groupings shown below

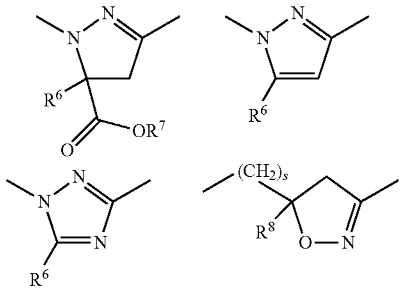

s represents 0, 1, 2, 3, 4 or 5, $A^2$ represents optionally $C_1$-$C_4$-alkyl-, $C_1$-$C_4$-alkoxy-carbonyl- and/or $C_1$-$C_4$-alkenyloxycarbonyl-substituted alkanediyl with 1 or 2 carbon atoms, $R^1$ represents hydroxyl, mercapto, amino, $C_1$-$C_6$-alkoxy, $C_1$-$C_6$-alkylthio, $C_1$-$C_6$-alkylamino or di($C_1$-$C_4$-alkyl)amino, $R^2$ represents hydroxyl, mercapto, amino, $C_1$-$C_7$-alkoxy, $C_1$-$C_6$-alkenyloxy, $C_1$-$C_6$-alkenyloxy-$C_1$-$C_6$-alkoxy, $C_1$-$C_6$-alkylthio, $C_1$-$C_6$-alkylamino or di($C_1$-$C_4$-alkyl)amino, $R^3$ represents in each case optionally fluorine-, chlorine- and/or bromine-substituted $C_1$-$C_4$-alkyl, $R^4$ represents hydrogen, in each case optionally fluorine-, chlorine- and/or bromine-substituted $C_1$-$C_6$-alkyl, $C_2$-$C_6$-alkenyl or $C_2$-$C_6$-alkynyl, $C_1$-$C_4$-alkoxy-$C_1$-$C_4$-alkyl, dioxolanyl-$C_1$-$C_4$-alkyl, furyl, furyl-$C_1$-$C_4$-alkyl, thienyl, thiazolyl, piperidinyl, or optionally fluorine-, chlorine- and/or bromine- or $C_1$-$C_4$-alkyl-substituted phenyl, $R^5$ represents hydrogen, in each case optionally fluorine-, chlorine- and/or bromine-substituted $C_1$-$C_6$-alkyl, $C_2$-$C_6$-alkenyl or $C_2$-$C_6$-alkynyl, $C_1$-$C_4$-alkoxy-$C_1$-$C_4$-alkyl, dioxolanyl-$C_1$-$C_4$-alkyl, furyl, furyl-$C_1$-$C_4$-alkyl, thienyl, thiazolyl, piperidinyl, or optionally fluorine-, chlorine- and/or bromine- or $C_1$-$C_4$-alkyl-substituted phenyl, $R^4$ and $R^5$ together also represent $C_3$-$C_6$-alkanediyl or $C_2$-$C_5$-oxaalkanediyl, each of which is optionally substituted by $C_1$-$C_4$-alkyl, phenyl, furyl, a fused-on benzene ring or by two substituents which together with the C atom to which they are attached form a 5- or 6-membered carbocycle, $R^6$ represents hydrogen, cyano, halogen, or represents in each case optionally fluorine-, chlorine- and/or bromine-substituted $C_1$-$C_4$-alkyl, $C_3$-$C_6$-cycloalkyl or phenyl, $R^7$ represents hydrogen, optionally hydroxyl-, cyano-, halogen- or $C_1$-$C_4$-alkoxy-substituted $C_1$-$C_6$-alkyl, $C_3$-$C_6$-cycloalkyl or tri($C_1$-$C_4$-alkyl)silyl, $R^8$ represents hydrogen, cyano, halogen, or represents in each case optionally fluorine-, chlorine- and/or bromine-substituted $C_1$-$C_4$-alkyl, $C_3$-$C_6$-cycloalkyl or phenyl, $X^1$ represents nitro, cyano, halogen, $C_1$-$C_4$-alkyl, $C_1$-$C_4$-haloalkyl, $C_1$-$C_4$-alkoxy or $C_1$-$C_4$-haloalkoxy, $X^2$ represents hydrogen, cyano, nitro, halogen, $C_1$-$C_4$-alkyl, $C_1$-$C_4$-haloalkyl, $C_1$-$C_4$-alkoxy or $C_1$-$C_4$-haloalkoxy, $X^3$ represents hydrogen, cyano, nitro, halogen, $C_1$-$C_4$-alkyl, $C_1$-$C_4$-haloalkyl, $C_1$-$C_4$-alkoxy or $C_1$-$C_4$-haloalkoxy, and/or the following compounds of the general formulae (I-d), (I-e)

(I-d)

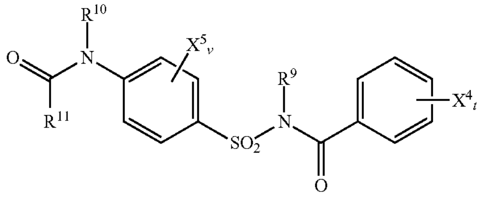

(I-e)

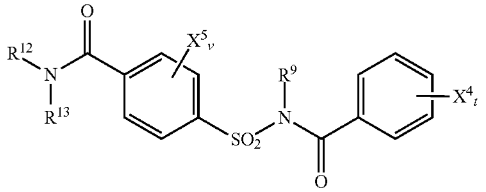

where t represents 0, 1, 2, 3, 4 or 5, v represents 0, 1, 2, 3 or 4, $R^9$ represents hydrogen or $C_1$-$C_4$-alkyl, $R^{10}$ represents hydrogen or $C_1$-$C_4$-alkyl, $R^{11}$ represents hydrogen, in each case optionally cyano-, halogen- or $C_1$-$C_4$-alkoxy-substituted $C_1$-$C_6$-alkyl, $C_1$-$C_6$-alkoxy, $C_1$-$C_6$-alkylthio, $C_1$-$C_6$-alkylamino or di($C_1$-$C_4$-alkyl)amino, or in each case optionally cyano-, halogen- or $C_1$-$C_4$-alkyl-substituted $C_3$-$C_6$-cycloalkyl, $C_3$-$C_6$-cycloalkyloxy, $C_3$-$C_6$-cycloalkylthio or $C_3$-$C_6$-cycloalkylamino, $R^{12}$ represents hydrogen, optionally cyano-, hydroxyl-, halogen- or $C_1$-$C_4$-alkoxy-substituted $C_1$-$C_6$-alkyl, in each case optionally cyano- or halogen-substituted $C_3$-$C_6$-alkenyl or $C_3$-$C_6$-alkynyl, or optionally cyano-, halogen- or $C_1$-$C_4$-alkyl-substituted $C_3$-$C_6$-cycloalkyl, $R^{13}$ represents hydrogen, optionally cyano-, hydroxyl-, halogen- or $C_1$-$C_4$-alkoxy-substituted $C_1$-$C_6$-alkyl, in each case optionally cyano- or halogen-substituted $C_3$-$C_6$-alkenyl or $C_3$-$C_6$-alkynyl, optionally cyano-, halogen- or $C_1$-$C_4$-alkyl-substituted $C_3$-$C_6$-cycloalkyl, or optionally nitro-, cyano-, halogen-, $C_1$-$C_4$-alkyl-, $C_1$-$C_4$-haloalkyl-, $C_1$-$C_4$-alkoxy- or $C_1$-$C_4$-haloalkoxy-substituted phenyl, or together with $R^{19}$ represents in each case optionally $C_1$-$C_4$-alkyl-substituted $C_2$-$C_6$-alkanediyl or $C_2$-$C_5$-oxaalkanediyl, $X^4$ represents nitro, cyano, carboxyl, carbamoyl, formyl, sulphamoyl, hydroxyl, amino, halogen, $C_1$-$C_4$-alkyl, $C_1$-$C_4$-haloalkyl, $C_1$-$C_4$-alkoxy or $C_1$-$C_4$-haloalkoxy, and $X^5$ represents nitro, cyano, carboxyl, carbamoyl, formyl, sulphamoyl, hydroxyl, amino, halogen, $C_1$-$C_4$-alkyl, $C_1$-$C_4$-haloalkyl, $C_1$-$C_4$-alkoxy or $C_1$-$C_4$-haloalkoxy.

In the definitions above and below, the saturated or unsaturated hydrocarbon radicals, such as an alkyl, alkenyl or alkanediyl, are in each case straight-chain or branched—including in combination with heteroatoms, such as an alkoxy.

Unless indicated otherwise, optionally substituted radicals may be mono- or polysubstituted, where in the case of polysubstitution the substituents may be identical or different.

The definition $C_1$-$C_7$-alkyl comprises the largest range defined here for an alkyl radical. Specifically, this definition comprises the meanings methyl, ethyl, n-, isopropyl, n-, iso-, sec-, tert-butyl, n-pentyl, 1-methylbutyl, 2-methylbutyl, 3-methylbutyl, 1-ethylpropyl, 1,1-dimethyl-propyl, 1,2-dimethylpropyl, 2,2-dimethylpropyl, and in each case all isomeric hexyls (such as, for example, n-hexyl, 1-methylpentyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl) and heptyls (such as, for example, n-heptyl, 1-methylhexyl, 1-ethylpentyl, 2-ethylpentyl, 1-propylbutyl).

These definitions can also be applied to alkyl radicals in combined meanings, such as, for example, in alkoxy, alkylamine, haloalkyl or cycloalkylalkyl. The scope of definition is determined by the range of carbon atoms given in each case.

The definition $C_2$-$C_6$-alkenyl comprises the largest range defined here for an alkenyl radical. Specifically, this definition comprises in particular the meanings vinyl, 1-propenyl, 2-propenyl, 1-butenyl, 2-butenyl, 3-butenyl, 1-methyl-4-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 2-ethyl-2-propenyl, 1-propylvinyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,2-dimethyl-1-butenyl, 1,3-dimethyl-1-butenyl, 1,2-dimethyl-1-butenyl, 2,3-dimethyl-1-butenyl, 3,3-dimethyl-1-butenyl, 1-ethyl-1-butenyl, 2-ethyl-1-butenyl, 1,1-dimethyl-2-butenyl, 1,2-dimethyl-2-butenyl, 1,3-dimethyl-2-butenyl, 2,3-dimethyl-2-butenyl, 1-ethyl-2-butenyl, 2-ethyl-2-butenyl, 1,1-dimethyl-3-butenyl, 1,2-dimethyl-3-butenyl, 1,3-dimethyl-3-butenyl, 2,2-dimethyl-3-butenyl, 2,3-dimethyl-3-butenyl, 1-ethyl-3-butenyl, 2-ethyl-3-butenyl, 1,1,2-trimethyl-2-propenyl, 1-ethyl-1-methyl-2-propenyl and 1-ethyl-2-methyl-2-propenyl.

These definitions can also be applied to alkenyl radicals in the combined meanings, such as, for example, in alkenyloxy or haloalkenyl. The scope of the definition is determined by the range of carbon atoms given in each case.

The definition $C_2$-$C_6$-alkynyl comprises the largest range defined here for an alkynyl radical. Specifically, this definition comprises in particular the meanings ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 3-methyl-1-butynyl, 1-methyl-2-butynyl, 1-methyl-3-butynyl, 2-methyl-3-butynyl, 1,1-dimethyl-2-propynyl, -ethyl-2-propynyl, 1-hexynyl, 2-hexynyl, 3-hexynyl, 4-hexynyl, 5-hexynyl, 3-methyl-1-pentynyl, 4-methyl-1-pentynyl, 1-methyl-2-pentynyl, 4-methyl-2-pentynyl, 1-methyl-3-pentynyl, 2-methyl-3-pentynyl, 1-methyl-4-pentynyl, 2-methyl-4-pentynyl, 3-methyl-4-pentynyl, 3,3-dimethyl-1-butynyl, 1,1-dimethyl-2-butynyl, 1-ethyl-2-butynyl, 1,1-dimethyl-3-butynyl, 1,2-dimethyl-3-butynyl, 2,2-dimethyl-3-butynyl, 1-ethyl-3-butynyl and 2-ethyl-3-butynyl.

These definitions can also be applied to alkynyl radicals in combined meanings, such as, for example, in alkynyloxy or haloalkynyl. The scope of the definition is determined by a range of carbon atoms given in each case.

The definition $C_3$-$C_6$-cycloalkyl comprises the largest range defined here for a cycloalkyl radical. Specifically, this definition comprises the meanings cyclopropyl, cyclobutyl, cyclopentyl and cyclohexyl.

These definitions can also be applied to cycloalkyl radicals in combined meanings, such as, for example, in halocycloalkyl, cycloalkylamino or cycloalkylalkyl. The scope of the definition is determined by the range of carbon atoms given in each case.

Depending inter alia on the nature of the substituents, the compounds of the formulae (I-a), (I-b), (I-c), (I-d) and (I-e) can be present as geometrical and/or optical isomers or isomer mixtures of varying composition which, if appropriate, may be separated in a customary manner. Both the pure isomers and the isomer mixtures can be used in the compositions according to the invention and employed for the use according to the invention. However, hereinbelow, for the sake of simplicity, only compounds of the formulae (I-a), (I-b), (I-c), (I-d) and (I-e) are referred to, although what is meant are both the pure compounds and, if appropriate, any mixtures having varying proportions of isomeric compounds.

Preferred meanings of the symbols and indices of the groups given in formulae (I-a), (I-b), (I-c), (I-d) and (I-c) are defined below.

r preferably represents 0, 1, 2, 3 or 4, $A^1$ preferably represents one of the divalent heterocyclic groupings shown below

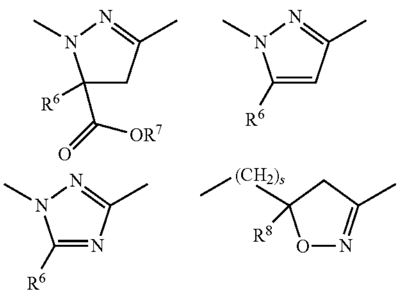

s preferably represents 0, 1, 2, 3 or 4, $A^2$ preferably represents in each case optionally methyl-, ethyl-, methoxycarbonyl-, ethoxycarbonyl- or allyloxycarbonyl-substituted methylene or ethylene.

$R^1$ preferably represents hydroxyl, mercapto, amino, methoxy, ethoxy, n- or i-propoxy, n-, i-, s- or t-butoxy, methylthio, ethylthio, n- or i-propylthio, n-, i-, s- or t-butylthio, methylamino, ethylamino, n- or i-propylamino, n-, i-, s- or t-butylamino, dimethylamino or diethylamino, $R^2$ preferably represents hydroxyl, mercapto, amino, methoxy, ethoxy, n- or i-propoxy, n-, i-, s- or t-butoxy, 1-methylhexyloxy, allyloxy, 1-allyloxymethylethoxy, methylthio, ethylthio, n- or i-propylthio, n-, i-, s- or t-butylthio, methylamino, ethylamino, n- or i-propylamino, n-, i-, s- or t-butylamino, dimethylamino or diethylamino, $R^3$ preferably represents in each case optionally fluorine-, chlorine- and/or bromine-substituted methyl, ethyl, n- or i-propyl, $R^4$ preferably represents hydrogen, in each case optionally fluorine- and/or chlorine-substituted methyl, ethyl, n- or i-propyl, n-, i-, s- or t-butyl, propenyl, butenyl, propynyl or butynyl, methoxymethyl, ethoxymethyl, methoxyethyl, ethoxyethyl, dioxolanylmethyl, furyl, furylmethyl, thienyl, thiazolyl, piperidinyl, or optionally fluorine-, chlorine-, methyl-, ethyl-, n- or i-propyl-, n-, i-, s- or t-butyl-substituted phenyl, $R^5$ preferably represents hydrogen, in each case optionally fluorine- and/or chlorine-substituted methyl, ethyl, n- or i-propyl, n-, i-, a- or t-butyl, propenyl, butenyl, propynyl or butynyl, methoxymethyl, ethoxymethyl, methoxyethyl, ethoxyethyl, dioxolanylmethyl, furyl, furylmethyl, thienyl, thiazolyl, piperidinyl, or optionally fluorine-, chlorine-, methyl-, ethyl-, n- or i-propyl-, n-, i-, s- or t-butyl-substituted phenyl, or together with R represents one of the radicals $—CH_2—O—CH_2—CH_2—$ and $—CH_2—CH_2—O—CH_2—CH_2—$, which are optionally substituted by methyl, ethyl, furyl, phenyl, a fused-on benzene ring or by two substituents which together with the C atom to which they are attached form a 5- or 6-membered carbocycle, $R^6$ preferably represents hydrogen, cyano, fluorine, chlorine, bromine, or represents in each case optionally fluorine-, chlorine- and/or bromine-substituted methyl, ethyl, n- or i-propyl, cyclopropyl, cyclobutyl, cyclopentyl, cyclohexyl or phenyl, $R^7$ preferably represents hydrogen, optionally hydroxyl-, cyano-, fluorine-, chlorine-, methoxy-, ethoxy-, n- or i-propoxy-substituted methyl, ethyl, n- or i-propyl, n-, i-, s- or t-butyl, $R^8$ preferably represents hydrogen, cyano, fluorine, chlorine, bromine, or represents in each case optionally fluorine-, chlorine- and/or bromine-substituted methyl, ethyl, n- or i-propyl, n-, i-, s- or t-butyl, cyclopropyl, cyclobutyl, cyclopentyl, cyclohexyl or phenyl, $X^1$ preferably represents nitro, cyano, fluorine, chlorine, bromine, methyl, ethyl, n- or i-propyl, n-, i-, a- or t-butyl, difluoromethyl, dichloromethyl, trifluoromethyl, trichloromethyl, chlorodifluoromethyl, fluorodichloromethyl, methoxy, ethoxy, n- or i-propoxy, difluoromethoxy or trifluoromethoxy, $X^2$ preferably represents hydrogen, nitro, cyano, fluorine, chlorine, bromine, methyl, ethyl, n- or i-propyl, n-, i-, s- or t-butyl, difluoromethyl, dichloromethyl, trifluoromethyl, trichloromethyl, chlorodifluoromethyl, fluorodichloromethyl, methoxy, ethoxy, n- or i-propoxy, difluoromethoxy or trifluoromethoxy, $X^3$ preferably represents hydrogen, nitro, cyano, fluorine, chlorine, bromine, methyl, ethyl, n- or i-propyl, n-, i-, s- or t-butyl, difluoromethyl, dichloromethyl, trifluoromethyl, trichloromethyl, chlorodifluoromethyl, fluorodichloromethyl, methoxy, ethoxy, n- or i-propoxy, difluoromethoxy or trifluoromethoxy, t preferably represents the number 0, 1, 2, 3 or 4, v preferably represents the number 0, 1, 2 or 3, $R^9$ preferably represents hydrogen, methyl, ethyl, n- or i-propyl, $R^{10}$ preferably represents hydrogen, methyl, ethyl, n- or i-propyl, $R^{11}$ preferably represents hydrogen, in each case optionally cyano-, fluorine-, chlorine-, methoxy-, ethoxy-, n- or i-propoxy-substituted methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, n-, i-, s- or t-butylthio, methylamino, ethylamino, n- or i-propylamino, n-, i-, a- or t-butylamino, dimethylamino or diethylamino, or in each case optionally cyano-, fluorine-, chlorine-, bromine-, methyl-, ethyl-, n- or i-propyl-substituted cyclopropyl, cyclobutyl, cyclopentyl, cyclohexyl, cyclopropyloxy, cyclobutyloxy, cyclopentyloxy, cyclohexyloxy, cyclopropylthio, cyclobutylthio, cyclopentylthio, cyclohexylthio, cyclopropylamino, cyclobutylamino, cyclopentylamino or cyclohexylamino, $R^{12}$ preferably represents hydrogen, in each case optionally cyano-, hydroxyl-, fluorine-, chlorine-, methoxy-, ethoxy-, n- or i-propoxy-substituted methyl, ethyl, n- or i-propyl, n-, i- or s-butyl, in each case optionally cyano-, fluorine-, chlorine- or bromine-substituted propenyl, butenyl, propynyl or butynyl, or in each case optionally cyano-, fluorine-, chlorine-, bromine-, methyl-, ethyl-, n- or i-propyl-substituted cyclopropyl, cyclobutyl, cyclopentyl or cyclohexyl, $R^{13}$ preferably represents hydrogen, in each case optionally cyano-, hydroxyl-, fluorine-, chlorine-, methoxy-, ethoxy-, n- or i-propoxy-substituted methyl, ethyl, n- or i-propyl, n-, i- or s-butyl, in each case optionally cyano-, fluorine-, chlorine- or bromine-substituted propenyl, butenyl, propynyl or butynyl, in each case optionally cyano-, fluorine-, chlorine-, bromine-, methyl-, ethyl-, n- or i-propyl-substituted cyclopropyl, cyclobutyl, cyclopentyl or cyclohexyl, or optionally nitro-, cyano-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, difluoromethoxy- or trifluoromethoxy-substituted phenyl, or together with $R^{12}$ represents in each case optionally methyl- or ethyl-substituted butane-1,4-diyl (trimethylene), pentane-1,5-diyl, 1-oxa-butane-1,4-diyl or 3-oxa-pentane-1,5-diyl, $X^4$ preferably represents nitro, cyano, carboxyl, carbamoyl, formyl, sulphamoyl, hydroxyl, amino, fluorine, chlorine, bromine, methyl, ethyl, n- or i-propyl, n-, i-, s- or t-butyl, trifluoromethyl, methoxy, ethoxy, n- or i-propoxy, difluoromethoxy or trifluoromethoxy, $X^5$ preferably represents nitro, cyano, carboxyl, carbamoyl, formyl, sulphamoyl, hydroxyl, amino, fluorine, chlorine, bromine, methyl, ethyl, n- or i-propyl, n-, i-, s- or t-butyl, trifluoromethyl, methoxy, ethoxy, n- or i-propoxy, difluoromethoxy or trifluoromethoxy.

Examples of compounds of the formula (I-a) which are very particularly preferred as safeners according to the invention are listed in the table below.

Specifically, particular mention may made of the following compounds of the formula (I-a):

TABLE 1

(I-a)

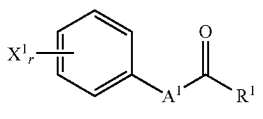

| No. | $X^1_r$ | $A^1$ | $R^1$ |
|---|---|---|---|
| I-a-1 | 2-Cl, 4-Cl | 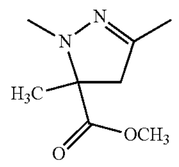 | $OCH_3$ |
| I-a-2 | 2-Cl, 4-Cl | 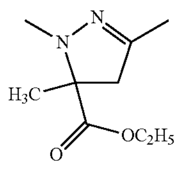 | $OCH_3$ |

TABLE 1-continued (I-a)

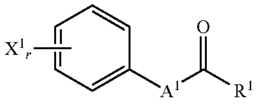

| No. | $X^1_r$ | $A^1$ | $R^1$ |
| --- | --- | --- | --- |
| I-a-3 | 2-Cl, 4-Cl | 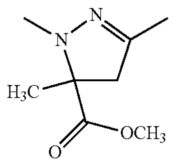 | $OC_2H_5$ |
| I-a-4 | 2-Cl, 4-Cl | 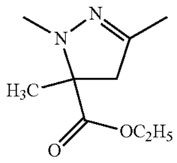 | $OC_2H_5$ |
| I-a-5 | 2-Cl | 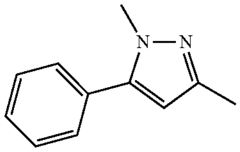 | $OCH_3$ |
| I-a-6 | 2-Cl, 4-Cl | 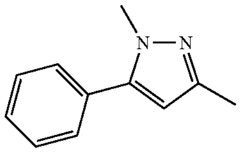 | $OCH_3$ |
| I-a-7 | 2-F | 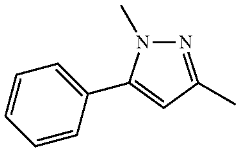 | $OCH_3$ |
| I-a-8 | 2-F | 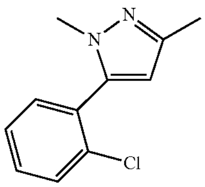 | $OCH_3$ |
| I-a-9 | 2-Cl, 4-Cl | 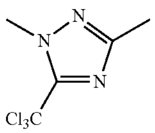 | $OC_2H_5$ |
| I-a-10 | 2-Cl, 4-$CF_3$ | 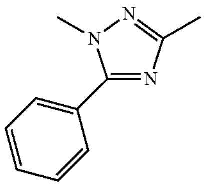 | $OCH_3$ |

TABLE 1-continued (I-a)

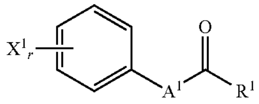

| No. | $X^1_r$ | $A^1$ | $R^1$ |
| --- | --- | --- | --- |
| I-a-11 | 2-Cl | 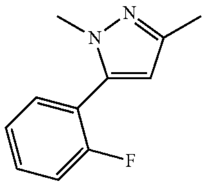 | $OCH_3$ |
| I-a-12 | — | 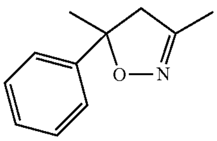 | $OC_2H_5$ |
| I-a-13 | 2-Cl, 4-Cl | 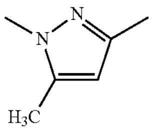 | $OC_2H_5$ |
| I-a-14 | 2-Cl, 4-Cl | 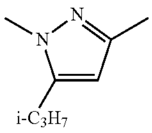 | $OC_2H_5$ |
| I-a-15 | 2-Cl, 4-Cl | 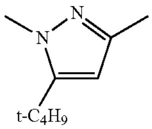 | $OC_2H_5$ |
| I-a-16 | 2-Cl, 4-Cl | 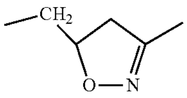 | $OC_2H_5$ |
| I-a-17 | 2-Cl, 4-Cl | 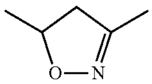 | $OC_2H_5$ |
| I-a-18 | — | 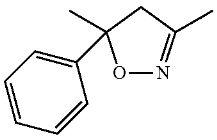 | OH |

Specifically, particular mention may furthermore be made of the following compounds of the formula (I-b):

TABLE 2

(I-b)

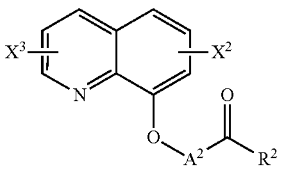

| No. | $X^2$ | $X^3$ | $A^2$ | $R^2$ |
|---|---|---|---|---|
| I-b-1 | 5-Cl | H | $CH_2$ | OH |
| I-b-2 | 5-Cl | H | $CH_2$ | $OCH_3$ |
| I-b-3 | 5-Cl | H | $CH_2$ | $OC_2H_5$ |
| I-b-4 | 5-Cl | H | $CH_2$ | $OC_3H_7$-n |
| I-b-5 | 5-Cl | H | $CH_2$ | $OC_3H_7$-i |
| I-b-6 | 5-Cl | H | $CH_2$ | $OC_4H_9$-n |
| I-b-7 | 5-Cl | H | $CH_2$ | $OCH(CH_3)C_5H_{11}$-n |
| I-b-8 | 5-Cl | 2-F | $CH_2$ | OH |
| I-b-9 | 5-Cl | 2-Cl | $CH_2$ | OH |
| I-b-10 | 5-Cl | H | $CH_2$ | $OCH_2CH{=}CH_2$ |
| I-b-11 | 5-Cl | H | $CH_2$ | $OC_4H_9$-i |
| I-b-12 | 5-Cl | H | $CH_2$ | $OCH(CH_3)CH_2OCH_2CH{=}CH_2$ |
| I-b-13 | 5-Cl | H | 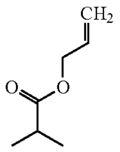 | $OCH_2CH{=}CH_2$ |
| I-b-14 | 5-Cl | H | 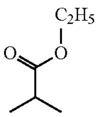 | $OC_2H_5$ |
| I-b-15 | 5-Cl | H | 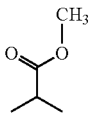 | $OCH_3$ |

Specifically, particular mention may furthermore be made of the following compounds of the formula (I-c):

TABLE 3

(I-c)

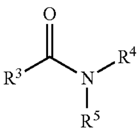

| No. | $R^3$ | $N(R^4R^5)$ |
|---|---|---|
| IV-c-1 | $CHCl_2$ | $N(CH_2CH{=}CH_2)_2$ |
| I-c-2 | $CHCl_2$ | 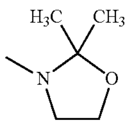 |
| I-c-3 | $CHCl_2$ | 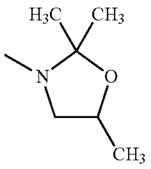 |

TABLE 3-continued (I-c)

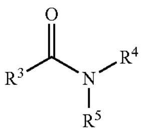

| No. | $R^3$ | $N(R^4R^5)$ |
|---|---|---|
| I-c-4 | $CHCl_2$ | 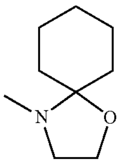 |
| I-c-5 | $CHCl_2$ | 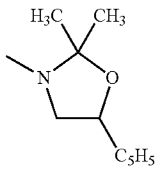 |
| I-c-6 | $CHCl_2$ | 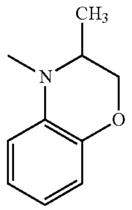 |
| I-c-7 | $CHCl_2$ | 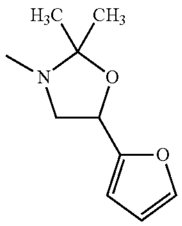 |

Specifically, particular mention may furthermore be made of the following compounds of the formula (I-d):

TABLE 4

(I-d)

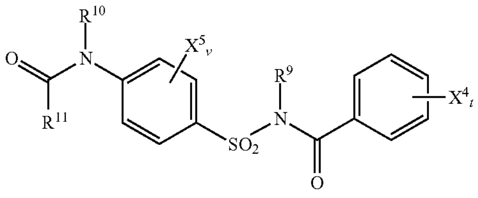

| No. | $R^9$ | $R^{10}$ | $R^{11}$ | $X^4{}_t$ | $X^5{}_v$ |
|---|---|---|---|---|---|
| I-d-1 | H | H | $CH_3$ | 2-$OCH_3$ | — |
| I-d-2 | H | H | $C_2H_5$ | 2-$OCH_3$ | — |
| I-d-3 | H | H | $C_3H_7$-n | 2-$OCH_3$ | — |
| I-d-4 | H | H | $C_3H_7$-i | 2-$OCH_3$ | — |
| I-d-5 | H | H | 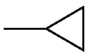 | 2-$OCH_3$ | — |
| I-d-6 | H | H | $CH_3$ | 2-$OCH_3$, 5-$CH_3$ | — |
| I-d-7 | H | H | $C_2H_5$ | 2-$OCH_3$, 5-$CH_3$ | — |

TABLE 4-continued (I-d)

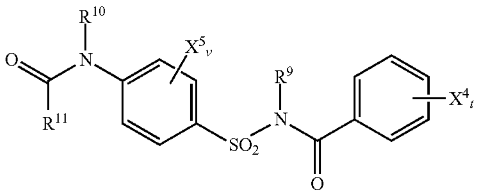

| No. | $R^9$ | $R^{10}$ | $R^{11}$ | $X^4_t$ | $X^5_v$ |
|---|---|---|---|---|---|
| I-d-8 | H | H | $C_3H_7$-n | 2-$OCH_3$, 5-$CH_3$ | — |
| I-d-9 | H | H | $C_3H_7$-i | 2-$OCH_3$, 5-$CH_3$ | — |
| I-d-10 | H | H | 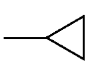 | 2-$OCH_3$, 5-$CH_3$ | — |
| I-d-11 | H | H | $OCH_3$ | 2-$OCH_3$, 5-$CH_3$ | — |
| I-d-12 | H | H | $OC_2H_5$ | 2-$OCH_3$, 5-$CH_3$ | — |
| I-d-13 | H | H | $OC_3H_7$-i | 2-$OCH_3$, 5-$CH_3$ | — |
| I-d-14 | H | H | $SCH_3$ | 2-$OCH_3$, 5-$CH_3$ | — |
| I-d-15 | H | H | $SC_2H_5$ | 2-$OCH_3$, 5-$CH_3$ | — |
| I-d-16 | H | H | $SC_3H_7$-i | 2-$OCH_3$, 5-$CH_3$ | — |
| I-d-17 | H | H | $NHCH_3$ | 2-$OCH_3$, 5-$CH_3$ | — |
| I-d-18 | H | H | $NHC_2H_5$ | 2-$OCH_3$, 5-$CH_3$ | — |
| I-d-19 | H | H | $NHC_3H_7$-i | 2-$OCH_3$, 5-$CH_3$ | — |
| I-d-20 | H | H | 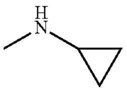 | 2-$OCH_3$, 5-$CH_3$ | — |
| I-4-21 | H | H | $NHCH_3$ | 2-$OCH_3$ | — |
| I-d-22 | H | H | $NHC_3H_7$-i | 2-$OCH_3$ | — |
| I-d-23 | H | H | $N(CH_3)_2$ | 2-$OCH_3$ | — |
| I-d-24 | H | H | $N(CH_3)_2$ | 3-$CH_3$, 4-$CH_3$ | — |
| I-d-25 | H | H | $CH_2$—O—$CH_3$ | 2-$OCH_3$ | — |

Specifically, particular mention may furthermore be made of the following compounds of the formula (I-e):

TABLE 5

(I-e)

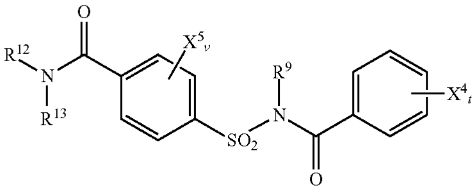

| No. | $R^9$ | $R^{12}$ | $R^{13}$ | $X^4_t$ | $X^5_v$ |
|---|---|---|---|---|---|
| I-e-1 | H | H | $CH_3$ | 2-$OCH_3$ | — |
| I-e-2 | H | H | $C_2H_5$ | 2-$OCH_3$ | — |
| I-e-3 | H | H | $C_3H_7$-n | 2-$OCH_3$ | — |
| I-e-4 | H | H | $C_3H_7$-i | 2-$OCH_3$ | — |
| I-e-5 | H | H | 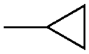 | 2-$OCH_3$ | — |
| I-e-6 | H | $CH_3$ | $CH_3$ | 2-$OCH_3$ | — |
| I-e-7 | H | H | $CH_3$ | 2-$OCH_3$, 5-$CH_3$ | — |
| I-e-8 | H | H | $C_2H_5$ | 2-$OCH_3$, 5-$CH_3$ | — |
| I-e-9 | H | H | $C_3H_7$-n | 2-$OCH_3$, 5-$CH_3$ | — |
| I-e-10 | H | H | $C_3H_7$-i | 2-$OCH_3$, 5-$CH_3$ | — |
| I-e-11 | H | H | 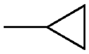 | 2-$OCH_3$, 5-$CH_3$ | — |
| I-e-12 | H | $CH_3$ | $CH_3$ | 2-$OCH_3$, 5-$CH_3$ | — |

Most preferred safeners of group 1 are cloquintocet-mexyl, fenchlorazol-ethyl, isoxadifen-ethyl, mefenpyr-diethyl, furilazole, fenclorim, cumyluron, dymron, dimepiperate and the compounds i-e-5 and i-e-11, and particular emphasis is given to cloquintocet-mexyl and mefenpyr-diethyl.

The compounds of the general formula (I-a) to be used as safeners are known and/or can be prepared by processes known per se (cf. WO 91/07874, WO 95/07897).

The compounds of the general formula (I-b) to be used as safeners are known and/or can be prepared by processes known per se (cf. EP-A 0 191 736).

The compounds of the general formula (I-c) to be used as safeners are known and/or can be prepared by processes known per se (cf. DE-A 22 18 097, DE-A 23 50 547).

The compounds of the general formula (I-d) to be used as safeners are known and/or can be prepared by processes known per se (cf. DE-A 196 21 522, U.S. Pat. No. 6,235,680).

The compounds of the general formula (I-e) to be used as safeners are known and/or can be prepared by processes known per se (cf. WO 99/66795, U.S. Pat. No. 6,251,827).

Further safeners mentioned in group 1 are described, for example, in C.D.S. Tomlin (Ed.), The Pesticide Manual, 13th Edition, British Crop Protection Council, Farnham, 2003.

The fungicides used according to the invention are generally one or more compounds from groups (2) to (24):

Group (2) Strobilurins of the General Formula (II)

(II)

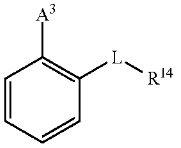

in which $A^3$ represents one of the groups

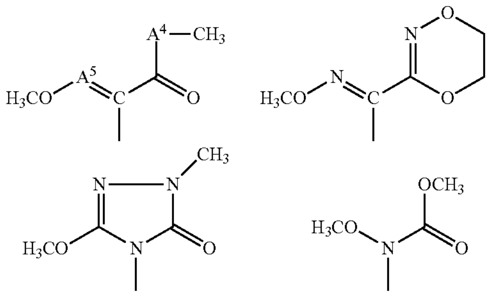

$A^4$ represents NH or O, $A^5$ represents N or CH,

L represents one of the groups

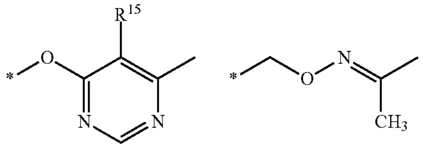

-continued

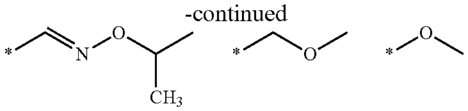

where the bond marked with an asterisk (*) is attached to the phenyl ring, $R^{14}$ represents phenyl, phenoxy or pyridinyl, each of which is optionally mono- or disubstituted by identical or different substituents from the group consisting of chlorine, cyano, methyl and trifluoromethyl, or represents 1-(4-chlorophenyl)pyrazol-3-yl or represents 1,2-propanedionebis(O-methyloxime)-1-yl, $R^{15}$ represents hydrogen or fluorine;

Group (3) Triazoles of the General Formula (III)

(III)

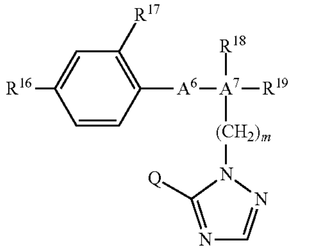

in which

Q represents hydrogen or SH, m represents 0 or 1, $R^{16}$ represents hydrogen, fluorine, chlorine, phenyl or 4-chlorophenoxy, $R^{17}$ represents hydrogen or chlorine, $A^6$ represents a direct bond, $-CH_2-$, $-(CH_2)_2-$ or $-O-$, $A^6$ furthermore represents $*-CH_2-CHR^{20}-$ or $*-CH{=}CR^{20}-$ where the bond marked with * is attached to the phenyl ring, and $R^{18}$ and $R^{20}$ furthermore together represent $-CH_2-CH_2-CH[CH(CH_3)_2]-$ or $-CH_2-CH_2-C(CH_3)_2$, $A^7$ represents C or Si (silicon), $A^6$ further represents $-N(R^{20})-$ and $A^7$ furthermore together with $R^{18}$ and $R^{19}$ represents the groups $C{=}N-R^{21}$, in which case $R^{20}$ and $R^{21}$ together represent the group

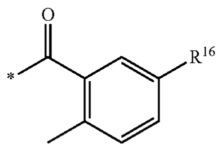

where the bond marked with * is attached to $R^{20}$, $R^{18}$ represents hydrogen, hydroxyl or cyano, $R^{19}$ represents 1-cyclopropylethyl, 1-chlorocyclopropyl, $C_1$-$C_4$-alkyl, $C_1$-$C_6$-hydroxyalkyl, $C_1$-$C_4$-alkylcarbonyl, $C_1$-$C_2$-haloalkoxy-$C_1$-$C_2$-alkyl, trimethylsilyl-$C_1$-$C_2$-alkyl, monofluorophenyl or phenyl, $R^{18}$ and $R^{19}$ furthermore together represent $-O-CH_2-CH(R^{21})-O-$, $-O-CH_2-CH(R^{21})-CH_2-$ or $-O-CH$-(2-chlorophenyl)-, $R^{20}$ together with $R^{18}$ represents $-CH_2-CH_2-CH[CH(CH_3)_2]-$ or $-CH_2-CH_2-C(CH_3)_2-$, or $R^{20}$ and $R^{21}$ together represent the group

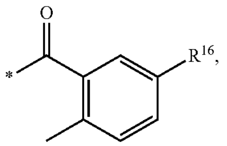

where the bond marked with * is attached to $R^{20}$, $R^{21}$ presents hydrogen, $C_1$-$C_4$-alkyl or bromine;

Group (4) Sulphenamides of the General Formula (IV)

(IV)

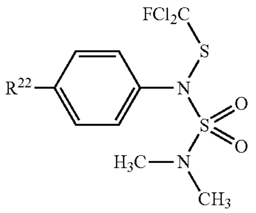

in which $R^{22}$ represents hydrogen or methyl;

Group (5) Valinamides Selected from (5-1) iprovalicarb (5-2) $N^1$-[2-(4-{[3-(4-chlorophenyl)-2-propynyl]oxy}-3-methoxyphenyl)ethyl]-$N^2$-(methylsulphonyl)-D-valinamide (5-3) benthiavalicarb Group (6) Carboxamides of the General Formula (V)

(V)

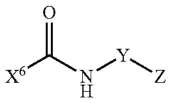

in which $X^6$ represents 2-chloro-3-pyridinyl, represents 1-methyl-pyrazol-4-yl which is substituted in the 3-position by methyl or trifluoromethyl and in the 5-position by hydrogen or chlorine, represents 4-ethyl-2-ethylamino-1,3-thiazol-5-yl, represents 1-methylcyclohexyl, represents 2,2-dichloro-1-ethyl-3-methylcyclopropyl, represents 2-fluoro-2-propyl or represents phenyl which is mono- to trisubstituted by identical or different substituents from the group consisting of chlorine and methyl, $X^6$ furthermore represents 3,4-dichloroisothiazol-5-yl, 5,6-dihydro-2-methyl-1,4-oxathiin-3-yl, 4-methyl-1,2,3-thiadiazol-5-yl, 4,5-dimethyl-2-trimethylsilylthiophen-3-yl, 1-methylpyrrol-3-yl which is substituted in the 4-position by methyl or trifluoromethyl and in the 5-position by hydrogen or chlorine, Y represents a direct bond, $C_1$-$C_6$-alkanediyl(alkylene) which is optionally substituted by chlorine, cyano or oxo or represents thiophenediyl, Y furthermore represents $C_2$-$C_6$-alkenediyl(alkenylene), Z represents hydrogen or the group

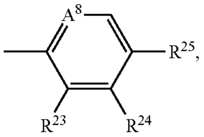

Z furthermore represents $C_1$-$C_6$-alkyl, $A^8$ represents CH or N, $R^{23}$ represents hydrogen, chlorine, phenyl which is optionally mono- or disubstituted by identical or different substituents from the group consisting of chlorine and di($C_1$-$C_3$-alkyl)aminocarbonyl, $R^{23}$ furthermore represents cyano or $C_1$-$C_6$-alkyl, $R^{24}$ represents hydrogen or chlorine, $R^{25}$ represents hydrogen, chlorine, hydroxyl, methyl or trifluoromethyl, $R^{25}$ furthermore represents di($C_1$-$C_3$-alkyl)aminocarbonyl, $R^{23}$ and $R^{24}$ furthermore together represent *—$CH(CH_3)$—$CH_2$—$C(CH_3)_2$— or *—$CH(CH_3)$—O—$C(CH_3)_2$— where the bond marked with * is attached to $R^{23}$;

Group (7) Dithiocarbamates Selected from (7-1) mancozeb (7-2) maneb (7-3) metiram (7-4) propineb (7-5) thiram (7-6) zineb (7-7) ziram Group (8) Acyalanines of the General Formula (VI)

(VI)

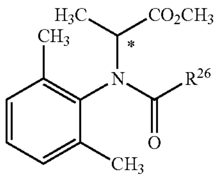

in which

* marks a carbon atom in the R or the S configuration, preferably in the S configuration, $R^{26}$ represents benzyl, furyl or methoxymethyl;

Group (9): Anilinpyrimidines of the General Formula (VII)

(VII)

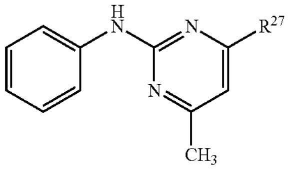

in which $R^{27}$ represents methyl, cyclopropyl or 1-propynyl;

Group (10): Benzimidazoles of the General Formula (VIII)

(VIII)

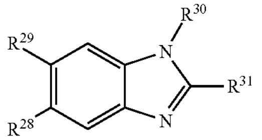

in which $R^{28}$ and $R^{29}$ each represent hydrogen or together represent —O—$CF_2$—O—, $R^{36}$ represents hydrogen, $C_1$-$C_4$-alkylaminocarbonyl or 3,5-dimethylisoxazol-4-ylsulphonyl, $R^{39}$ represents chlorine, methoxycarbonylamino, chlorophenyl, furyl or thiazolyl;

Group (11): Carbamates of the General Formula (IX)

(IX)

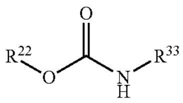

in which $R^{32}$ represents n- or isopropyl.

$R^{33}$ represents di($C_1$-$C_2$-alkyl)amino-$C_2$-$C_4$-alkyl or diethoxyphenyl, salts of these compounds also being included;

Group (12): Dicarboximides Selected from (12-1) captafol (12-2) captan (12-3) folpet (12-4) iprodione (12-5) procymidone (12-6) vinclozolin Group (13): Guanidines Selected from (13-1) dodine (13-2) guazatine (13-3) iminoctadine triacetate (13-4) iminoctadine tris(albesilate)

Group (14): Imidazoles Selected from (14-1) cyazofamid (14-2) prochloraz (14-3) triazoxide (14-4) pefurazoate Group (15): Morpholines of the General Formula (X)

(X)

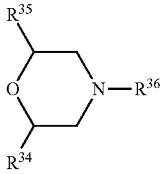

in which $R^{34}$ and $R^{35}$ independently of one another represent hydrogen or methyl, $R^{36}$ represents $C_1$-$C_{14}$-alkyl (preferably $C_{12}$-$C_{14}$-alkyl), $C_5$-$C_{12}$-cycloalkyl (preferably $C_{10}$-$C_{12}$-cycloalkyl), phenyl-$C_1$-$C_4$-alkyl, which may be substituted in the phenyl moiety by halogen or $C_1$-$C_4$-alkyl or represents acrylyl which is substituted by chlorophenyl and dimethoxyphenyl;

Group (16): Pyrroles of the General Formula (XI)

(XI)

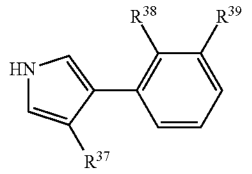

in which $R^{37}$ represents chlorine or cyano, $R^{38}$ represents chlorine or nitro, $R^{39}$ represents chlorine, $R^{38}$ and $R^{39}$ furthermore together represent —O—$CF_2$—O—;

Group (17): Phosphonates Selected from (17-1) fosetyl-Al (17-2) phosphonic acid;

Group (18): Phenylethanamides of the General Formula (XII)

(XII)

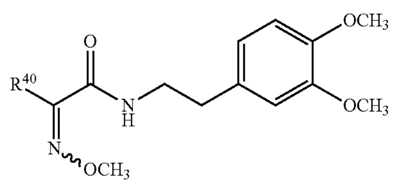

in which $R^{40}$ represents unsubstituted or fluorine-, chlorine-, bromine-, methyl- or ethyl-substituted phenyl, 2-naphthyl, 1,2,3,4-tetrahydronaphthyl or indanyl;

Group (19): Fungicides Selected from (19-1) acibenzolar-S-methyl (19-2) chlorothalonil (19-3) cymoxanil (19-4) edifenphos (19-5) famoxadone (19-6) fluazinam (19-7) copper oxychloride (19-8) copper hydroxide (19-9) oxadixyl (19-10) spiroxamine (19-11) dithianon (19-12) metrafenone (19-13) fenamidone (19-14) 2,3-dibutyl-6-chlorothieno[2,3-d]pyrimidin-4(3H)-one (19-15) probenazole (19-16) isoprothiolane (19-17) kasugamycin (19-18) phthalide (19-19) ferimzone (19-20) tricyclazole (19-21) N-({4-[(cyclopropylamino)carbonyl]phenyl}sulphonyl)-2-methoxybenzamide Group (20): (Thio)urea Derivatives Selected from (20-1) pencycuron (20-2) thiophanate-methyl (20-3) thiohanate-ethyl Group (21): Amides of the general formula (XIII)

(XIII)

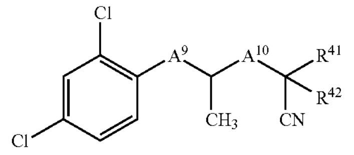

in which $A^9$ represents a direct bond or —O—, $A^{10}$ represents —C(═O)NH— or —NHC(═O)—, $R^{41}$ represents hydrogen or $C_1$-$C_4$-alkyl, $R^{42}$ represents $C_1$-$C_6$-alkyl;

Group (22): Triazolopyrimidines of the general formula (XIV)

(XIV)

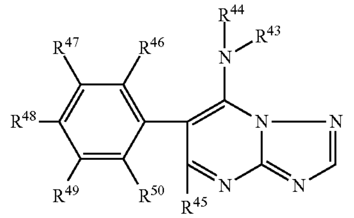

in which $R^{43}$ represents $C_1$-$C_6$-alkyl or $C_2$-$C_6$-alkenyl, $R^{44}$ represents $C_1$-$C_6$-alkyl, $R^{43}$ and $R^{44}$ furthermore together represent $C_1$-$C_6$-alkanediyl(alkylene) which is mono- or disubstituted by $C_1$-$C_6$-alkyl, $R^{45}$ represents bromine or chlorine, $R^{46}$ and $R^{50}$ independently of one another represent hydrogen, fluorine, chlorine or methyl, $R^{47}$ and $R^{49}$ independently of one another represent hydrogen or fluorine, $R^{48}$ represents hydrogen, fluorine or methyl, Group (23): Iodochromones of the General Formula (XV)

(XV)

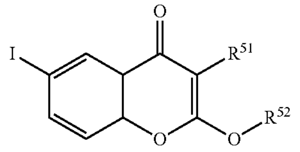

in which $R^{51}$ represents $C_1$-$C_6$-alkyl, $R^{52}$ represents $C_1$-$C_6$-alkyl, $C_2$-$C_6$-alkenyl or $C_2$-$C_6$-alkynyl;

Group (24): Biphenylcarboxamides of the General Formula (XVI)

(XVI)

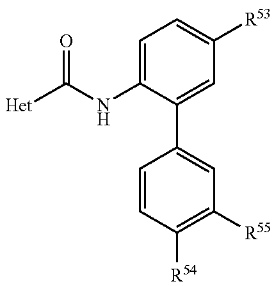

in which $R^{53}$ represents hydrogen or fluorine, $R^{51}$ represents fluorine, chlorine, bromine, methyl, trifluoromethyl, trifluoromethoxy, —CH═N—OMe or —C(Me)═N—OMe, $R^{55}$ represents hydrogen, fluorine, chlorine, bromine, methyl or trifluoromethyl, Het represents one of the radicals Het1 to Het7 below:

Het1

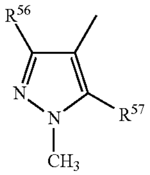

Het2

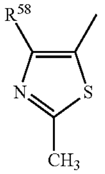

Het3

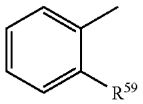

Het4

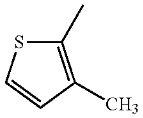

Het5

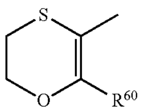

Het6

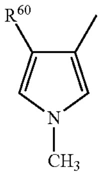

-continued

Het7

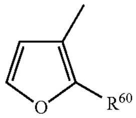

$R^{56}$ represents iodine, methyl, difluoromethyl or trifluoromethyl, $R^{57}$ represents hydrogen, fluorine, chlorine or methyl, $R^{58}$ represents methyl, difluoromethyl or trifluoromethyl, $R^{59}$ represents chlorine, bromine, iodine, methyl, difluoromethyl or trifluoromethyl, $R^{60}$ represents methyl or trifluoromethyl.

The formula (II) embraces the following preferred mixing partners of group (2):

(2-1) azoxystrobin (known from EP-A 0 382 375) of the formula

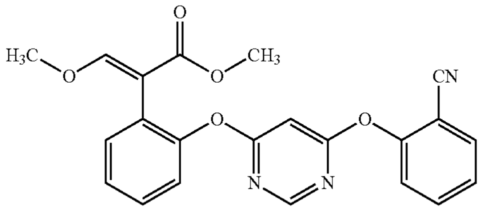 [SMILES: CO/C=C(/C(=O)OC)c1ccccc1Oc1cc(Oc2ccccc2C#N)ncn1]

(2-2) fluoxastrobin (known from DE-A 196 02 095) of the formula

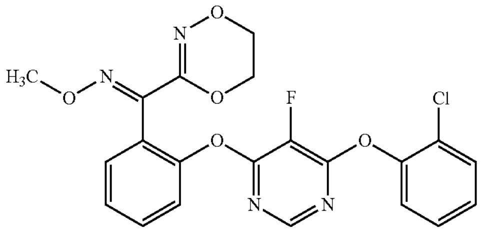 [SMILES: CO/N=C(/C1=NOCCO1)c1ccccc1Oc1ncnc(Oc2ccccc2Cl)c1F]

(2-3) (2E)-2-(2-{[6-(3-chloro-2-methylphenoxy)-5-fluoro-4-pyrimidinyl]oxy}phenyl)-2-(methoxy-imino)-N-methylethanamide (known from DE-A 196 46 407, EP-B 0 712 396) of the formula

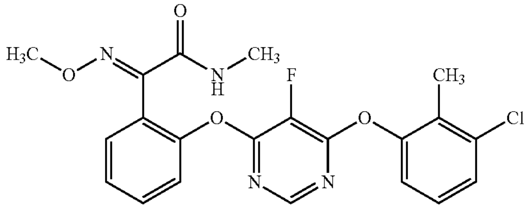 [SMILES: CNC(=O)/C(=N/OC)c1ccccc1Oc1ncnc(Oc2cccc(Cl)c2C)c1F]

(2-4) trifloxystrobin (known from EP-A 0 460 575) of the formula

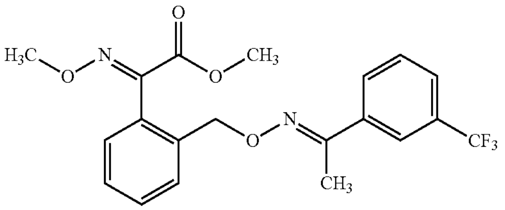 [SMILES: CO/N=C(/C(=O)OC)c1ccccc1CO/N=C(\C)c1cccc(C(F)(F)F)c1]

(2-5) (2E)-2-(methoxyimino)-N-methyl-2-(2-{[({(1E)-1-[3-(trifluoromethyl)phenyl]ethylidene}-amino)oxy] methyl}phenyl)ethanamide (known from EP-A 0 569 384) of the formula

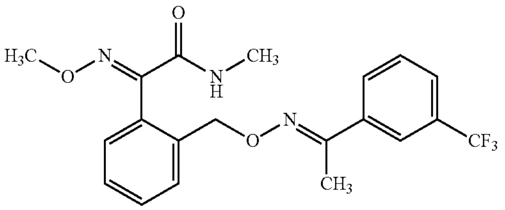 [SMILES: CNC(=O)/C(=N/OC)c1ccccc1CO/N=C(\C)c1cccc(C(F)(F)F)c1]

(2-6) (2E)-2-(methoxyimino)-N-methyl-2-{2-[(E)-({1-[3-(trifluoromethyl)phenyl)ethoxy}imino)-methyl] phenyl}ethanamide (known from EP-A 0 596 254) of the formula

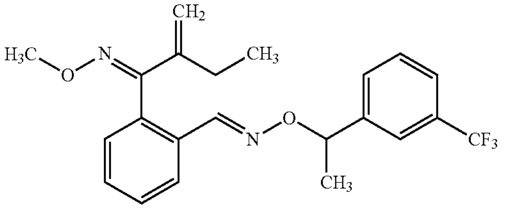 [SMILES: C=C(CC)/C(=N/OC)c1ccccc1/C=N/OC(C)c1cccc(C(F)(F)F)c1]

(2-7) orysastrobin (known from DE-A 195 39 324) of the formula

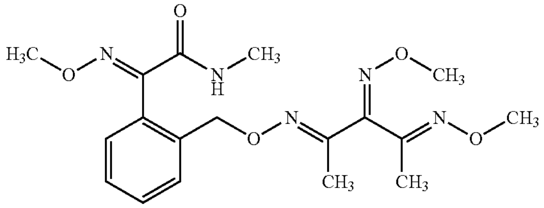

(2-8) 5-methoxy-2-methyl-4-(2-{[({(1E)-1-[3-(trifluoromethyl)phenyl]ethylidene}amino)oxy]-methyl}phenyl)-2,4-dihydro-3H-1,2,4-triazol-3-one (known from WO 98/23155) of the formula

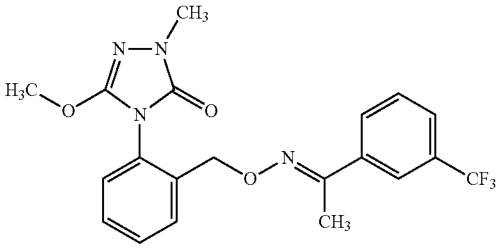 [SMILES: COc1nn(C)c(=O)n1-c1ccccc1CO/N=C(\C)c1cccc(C(F)(F)F)c1]

(2-9) kresoxim-methyl (known from EP-A 0 253 213) of the formula

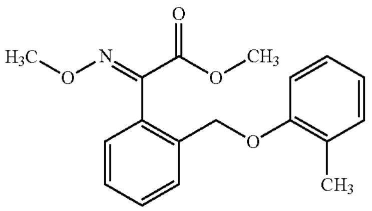 [SMILES: CO/N=C(/C(=O)OC)c1ccccc1COc1ccccc1C]

(2-10) dimoxystrobin (known from EP-A 0 398 692) of the formula

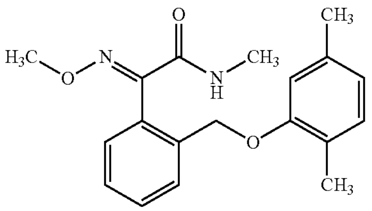 [SMILES: CNC(=O)/C(=N/OC)c1ccccc1COc1cc(C)ccc1C]

(2-11) picoxystrobin (known from EP-A 0 278 595) of the formula

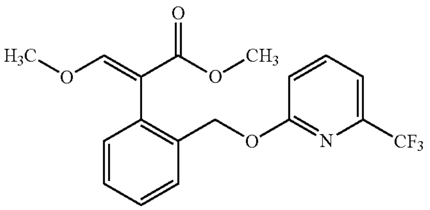 [SMILES: CO/C=C(/C(=O)OC)c1ccccc1COc1cccc(C(F)(F)F)n1]

(2-12) pyraclostrobin (known from DE-A 44 23 612) of the formula

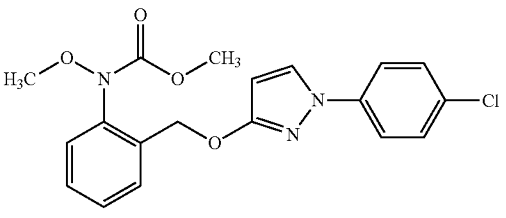 [SMILES: COC(=O)N(OC)c1ccccc1COc1ccn(-c2ccc(Cl)cc2)n1]

(2-13) metominostrobin (known from EP-A 0 398 692) of the formula

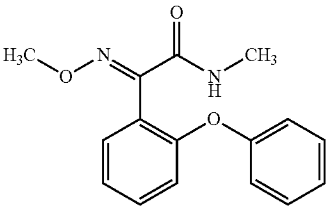 [SMILES: CNC(=O)/C(=N/OC)c1ccccc1Oc1ccccc1]

The formula (II) embraces the following preferred mixing partners of group (3):

(3-1) azaconazole (known from DE-A 25 51 560) of the formula

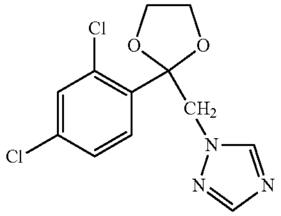 [SMILES: Clc1ccc(C2(Cn3cncn3)OCCO2)c(Cl)c1]

(3-2) etaconazole (known from DE-A 25 51 560) of the formula

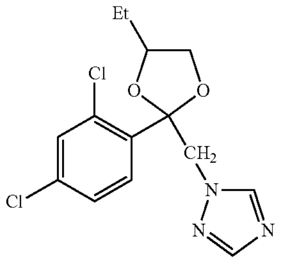 [SMILES: CCC1COC(Cn2cncn2)(c2ccc(Cl)cc2Cl)O1]

(3-3) propiconazole (known from DE-A 25 51 560) of the formula

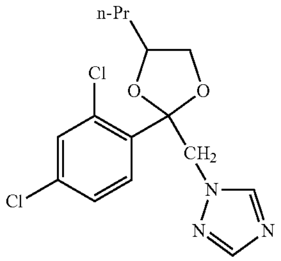

(3-4) difenoconazole (known from EP-A 0 112 284) of the formula

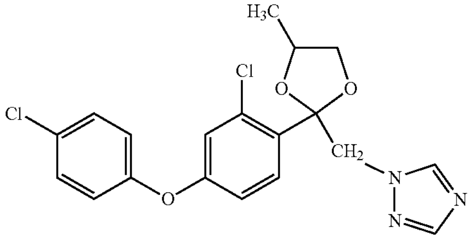 [SMILES: CC1COC(Cn2cncn2)(c2ccc(Oc3ccc(Cl)cc3)cc2Cl)O1]

(3-5) bromuconazole (known from EP-A 0 258 161) of the formula

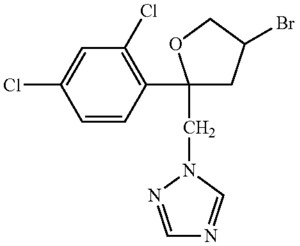 [SMILES: Clc1ccc(C2(Cn3cncn3)CC(Br)CO2)c(Cl)c1]

(3-6) cyproconazole (known from DE-A 34 06 993) of the formula

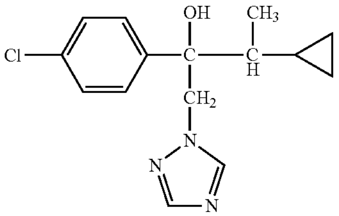 [SMILES: CC(C1CC1)C(O)(Cn1cncn1)c1ccc(Cl)cc1]

(3-7) hexaconazole (known from DE-A 30 42 303) of the formula

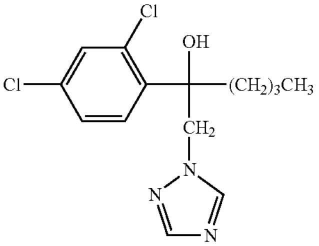

(3-8) penconazole (known from DE-A 27 35 872) of the formula

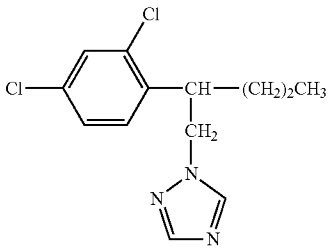
(3-9) myclobutanil (known from EP-A 0 145 294) of the formula
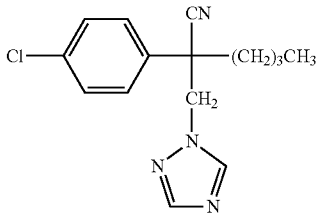
(3-10) tetraconazole (known from EP-A 0 234 242) of the formula
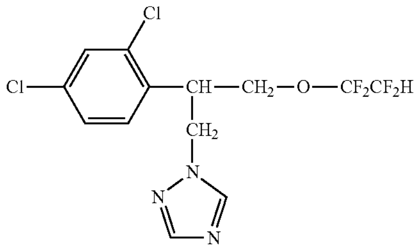
(3-11) flutriafol (known from EP-A 0 015 756) of the formula
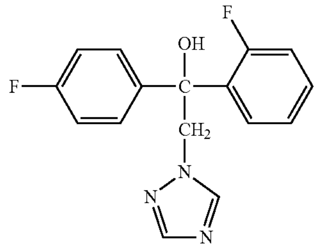 [SMILES: OC(Cn1cncn1)(c1ccc(F)cc1)c1ccccc1F]
(3-12) epoxiconazole (known from EP-A 0 196 038) of the formula
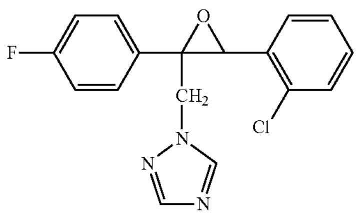 [SMILES: Fc1ccc(C2(Cn3cncn3)OC2c2ccccc2Cl)cc1]
(3-13) flusilazole (known from EP-A 0 068 813) of the formula
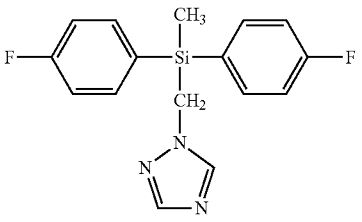 [SMILES: C[Si](Cn1cncn1)(c1ccc(F)cc1)c1ccc(F)cc1]
(3-14) simeconazole (known from EP-A 0 537 957) of the formula
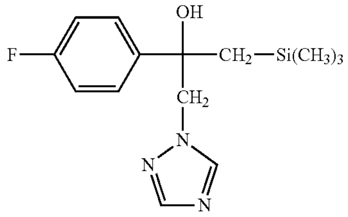
(3-15) prothioconazole (known from WO 96/16048) of the formula
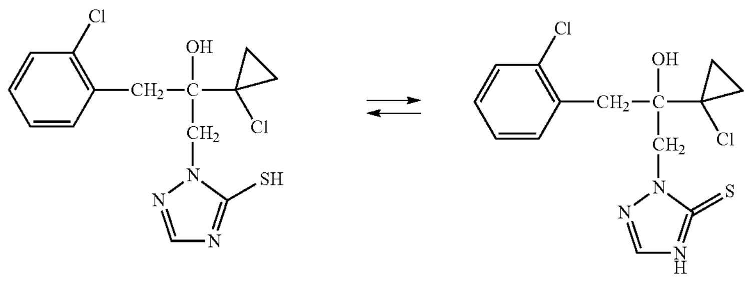

(3-16) fenbuconazole (known from DE-A 37 21 786) of the formula

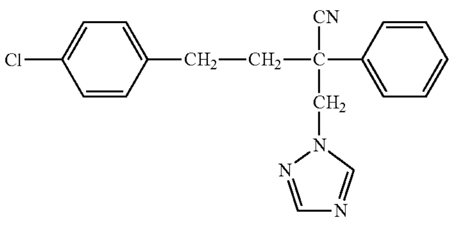 [SMILES: N#CC(CCc1ccc(Cl)cc1)(Cn1cncn1)c1ccccc1]

(3-17) tebuconazole (known from EP-A 0 040 345) of the formula

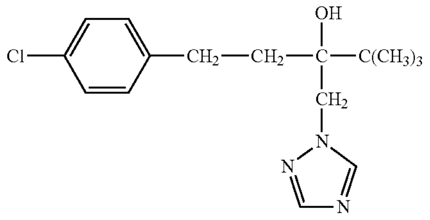 [SMILES: CC(C)(C)C(O)(CCc1ccc(Cl)cc1)Cn1cncn1]

(3-18) ipconazole (known from EP-A 0 329 397) of the formula

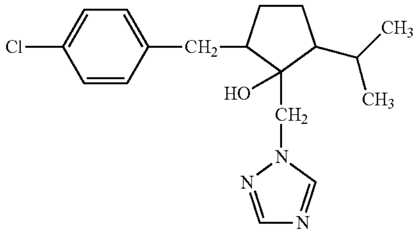 [SMILES: CC(C)C1CCC(Cc2ccc(Cl)cc2)C1(O)Cn1cncn1]

(3-19) metconazole (known from EP-A 0 329 397) of the formula

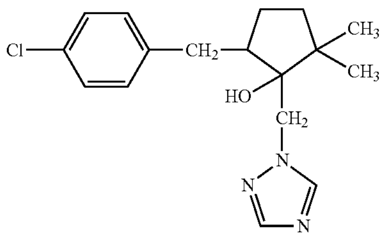 [SMILES: CC1(C)CCC(Cc2ccc(Cl)cc2)C1(O)Cn1cncn1]

(3-20) triticonazole (known from EP-A 0 378 953) of the formula

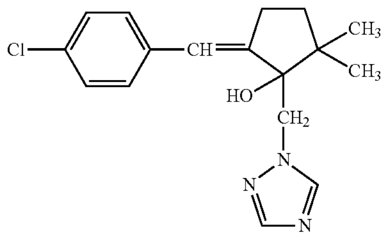 [SMILES: CC1(C)CCC(=Cc2ccc(Cl)cc2)C1(O)Cn1cncn1]

(3-21) bitertanol (known from DE-A 23 24 010) of the formula

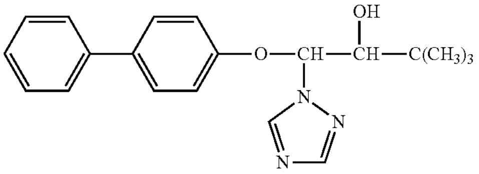 [SMILES: CC(C)(C)C(O)C(Oc1ccc(-c2ccccc2)cc1)n1cncn1]

(3-22) triadimenol (known from DE-A 23 24 010) of the formula

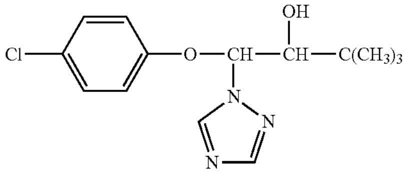 [SMILES: CC(C)(C)C(O)C(Oc1ccc(Cl)cc1)n1cncn1]

(3-23) triadimefon (known from DE-A 22 01 063) of the formula

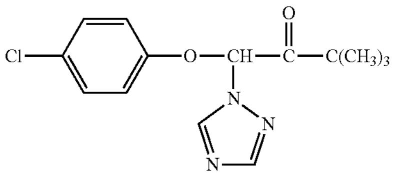 [SMILES: CC(C)(C)C(=O)C(Oc1ccc(Cl)cc1)n1cncn1]

(3-24) fluquinconazole (known from EP-A 0 183 458) of the formula

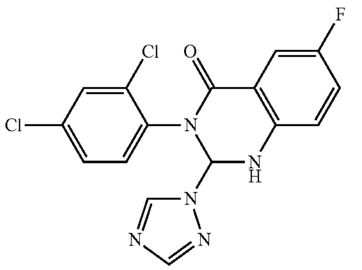 [SMILES: O=C1c2cc(F)ccc2NC(n2cncn2)N1c1ccc(Cl)cc1Cl]

(3-25) quinconazole (known from EP-A 0 183 458) of the formula

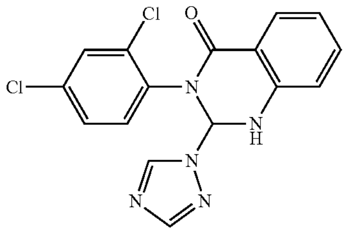 [SMILES: O=C1c2ccccc2NC(n2cncn2)N1c1ccc(Cl)cc1Cl]

The formula (IV) embraces the following preferred mixing partners of group (4):

(4-1) dichlofluanid (known from DE-A 11 93 498) of the formula

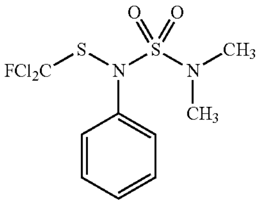

(4-2) tolylfluanid (known from DE-A 11 93 498) of the formula

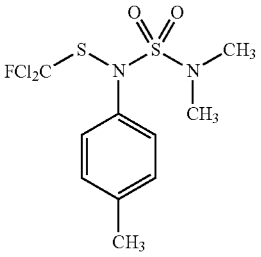

Preferred mixing partners of group (5) are (5-1) iprovalicarb (known from DE-A 40 26 966) of the formula

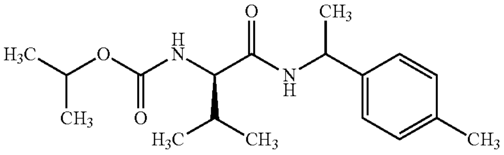 [SMILES: Cc1ccc(C(C)NC(=O)[C@H](NC(=O)OC(C)C)C(C)C)cc1]

(5-3) benthiavalicarb (known from WO 96/04252) of the formula

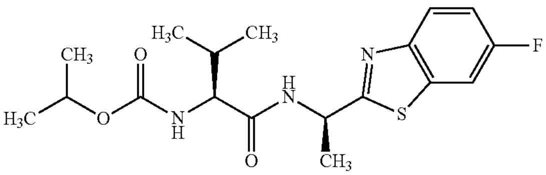 [SMILES: CC(C)OC(=O)N[C@H](C(=O)N[C@H](C)c1nc2ccc(F)cc2s1)C(C)C]

The formula (V) embraces the following preferred mixing partners of group (6):

(6-1) 2-chloro-N-(1,1,3-trimethylindan-4-yl)nicotinamide (known from EP-A 0 256 503) of the formula

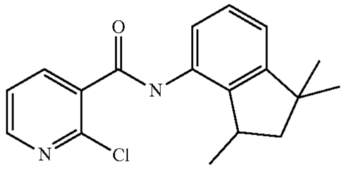 [SMILES: CC1CC(C)(C)c2cccc(NC(=O)c3cccnc3Cl)c21]

(6-2) boscalid (known from DE-A 195 31 813) of the formula

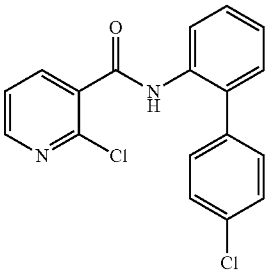 [SMILES: O=C(Nc1ccccc1-c1ccc(Cl)cc1)c1cccnc1Cl]

(6-3) furametpyr (known from EP-A 0 315 502) of the formula

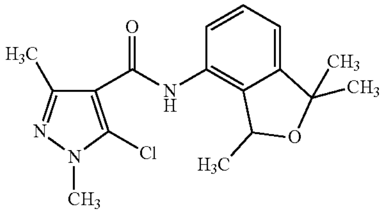

(6-4) N-(3-p-tolylthiophen-2-yl)-1-methyl-3-trifluoromethyl-1H-pyrazole-4-carboxamide (known from EP-A 0 737 682) of the formula

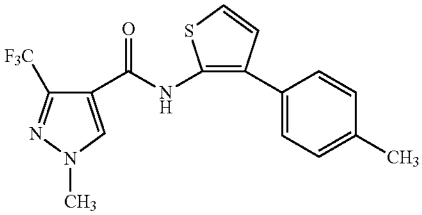 [SMILES: Cc1ccc(-c2ccsc2NC(=O)c2cn(C)nc2C(F)(F)F)cc1]

(6-5) ethaboxam (known from EP-A 0 639 574) of the formula

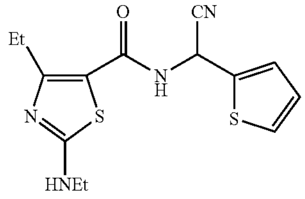

(6-6) fenhexamid (known from EP-A 0 339 418) of the formula

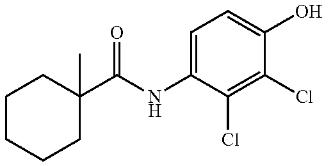 [SMILES: CC1(C(=O)Nc2ccc(O)c(Cl)c2Cl)CCCCC1]

(6-7) carpropamid (known from EP-A 0 341 475) of the formula

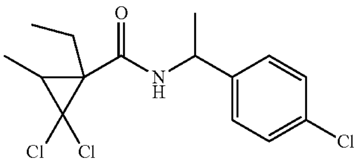 [SMILES: CCC1(C(=O)NC(C)c2ccc(Cl)cc2)C(C)C1(Cl)Cl]

(6-8) 2-chloro-4-(2-fluoro-2-methylpropionylamino)-N,N-dimethylbenzamide (known from EP-A 0 600 629) of the formula

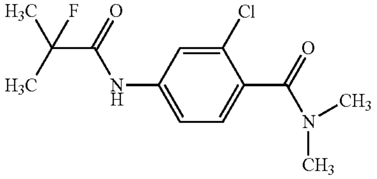 [SMILES: CN(C)C(=O)c1ccc(NC(=O)C(C)(C)F)cc1Cl]

(6-9) picobenzamid (known from WO 99/42447) of the formula

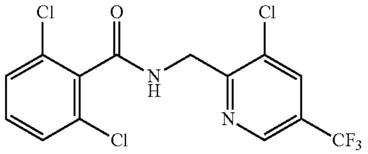 [SMILES: O=C(NCc1ncc(C(F)(F)F)cc1Cl)c1c(Cl)cccc1Cl]

(6-10) zoxamide (known from EP-A 0 604 019) of the formula

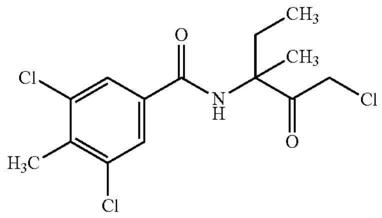 [SMILES: CCC(C)(NC(=O)c1cc(Cl)c(C)c(Cl)c1)C(=O)CCl]

(6-11) 3,4-dichloro-N-(2-cyanophenyl)isothiazole-5-carboxamide (known from WO 99/24413) of the formula

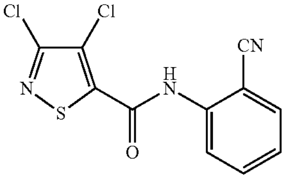 [SMILES: N#Cc1ccccc1NC(=O)c1snc(Cl)c1Cl]

(6-12) carboxin (known from U.S. Pat. No. 3,249,499) of the formula

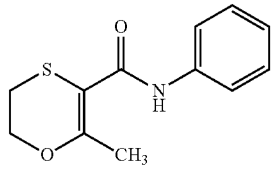 [SMILES: CC1=C(C(=O)Nc2ccccc2)SCCO1]

(6-13) tiadinil (known from U.S. Pat. No. 6,616,054) of the formula

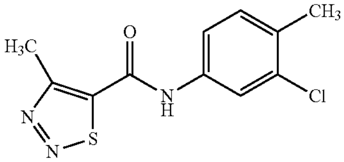 [SMILES: Cc1ccc(NC(=O)c2snnc2C)cc1Cl]

(6-14) penthiopyrad (known from EP-A 0 737 682) of the formula

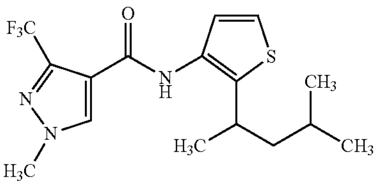 [SMILES: CC(C)CC(C)c1sccc1NC(=O)c1cn(C)nc1C(F)(F)F]

(6-15) silthiofam (known from WO 96/18631) of the formula

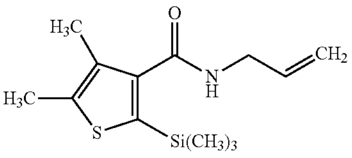

(6-16) N-[2-(1,3-dimethylbutyl)phenyl]-1-methyl-4-(trifluoroethyl)-1H-pyrrole-3-carboxamide (known from WO 02/38542) of the formula

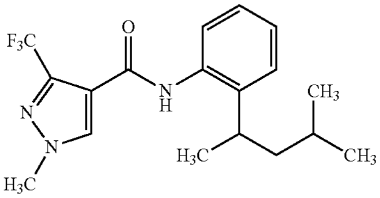 [SMILES: CC(C)CC(C)c1ccccc1NC(=O)c1cn(C)nc1C(F)(F)F]

Preferred mixing partners of group (7) are (7-1) mancozeb (known from DE-A 12 34 704) having the IUPAC name manganese ethylenebis(dithiocarbamate) (polymeric) complex with zinc salt (7-2) maneb (known from U.S. Pat. No. 2,504,404) of the formula

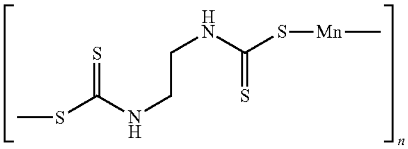

(7-3) metiram (known from DE-A 10 76 434) having the IUPAC name zinc ammoniate ethylenebis(dithiocarbamate)-poly(ethylenethiuram disulphide)

(7-4) propineb (known from GB 935 981) of the formula

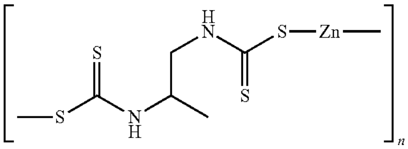

(7-5) thiram (known from U.S. Pat. No. 1,972,961) of the formula

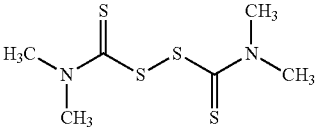

(7-6) zineb (known from DE-A 10 81 446) of the formula

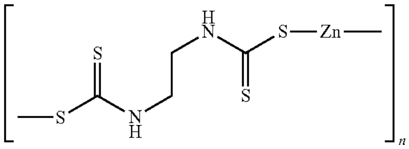

(7-7) ziram (known from U.S. Pat. No. 2,588,428) of the formula

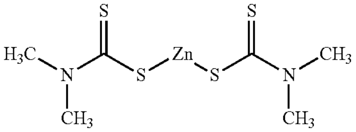

The formula (VI) embraces the following preferred mixing partners of group (8):

(8-1) benalaxyl (known from DE-A 29 03 612) of the formula

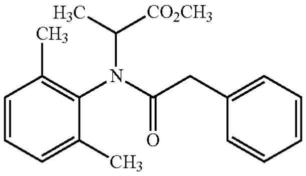

(8-2) furalaxyl (known from DE-A 25 13 732) of the formula

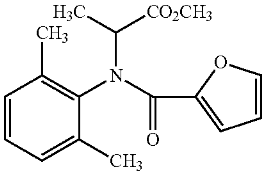 [SMILES: COC(=O)C(C)N(C(=O)c1ccco1)c1c(C)cccc1C]

(8-3) metalaxyl (known from DE-A 25 15 091) of the formula

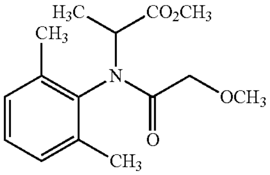

(8-4) metalaxyl-M (known from WO 96/01559) of the formula

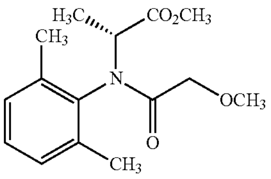

(8-5) benalaxyl-M of the formula

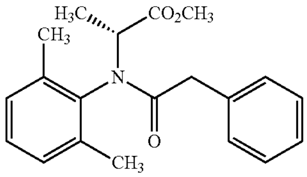 [SMILES: COC(=O)[C@@H](C)N(C(=O)Cc1ccccc1)c1c(C)cccc1C]

The formula (VII) embraces the following preferred mixing partners of group (9):

(9-1) cyprodinil (known from EP-A 0 310 550) of the formula

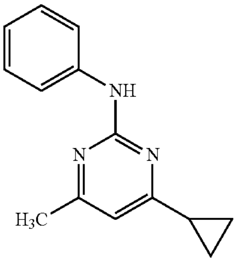 [SMILES: Cc1cc(C2CC2)nc(Nc2ccccc2)n1]

(9-2) mepanipyrim (known from EP-A 0 270 111) of the formula

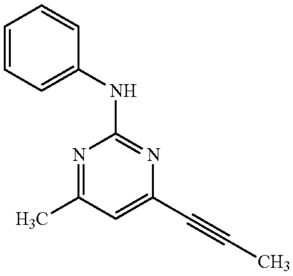 [SMILES: CC#Cc1cc(C)nc(Nc2ccccc2)n1]

(9-3) pyrimethanil (known from DD 151 404) of the formula

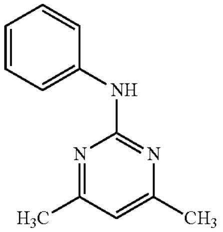

The formula (VIII) embraces the following preferred mixing partners of group (10):

(10-1) 6-chloro-5-[(3,5-dimethylisoxazol-4yl)sulphonyl]-2,2-difluoro-5H-[1,3]dioxolo[4,5-f]-benzimidazole (known from WO 97/06171) of the formula

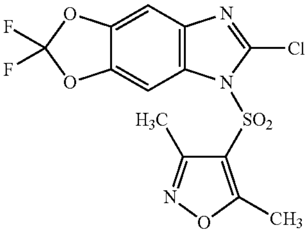 [SMILES: Cc1noc(C)c1S(=O)(=O)n1c(Cl)nc2cc3c(cc21)OC(F)(F)O3]

(10-2) benomyl (known from U.S. Pat. No. 3,631,176) of the formula

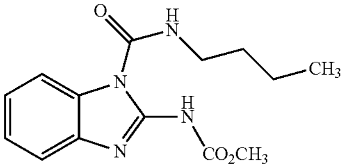 [SMILES: CCCCNC(=O)n1c(NC(=O)OC)nc2ccccc21]

(10-3) carbendazim (known from U.S. Pat. No. 3,010,968) of the formula

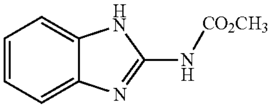 [SMILES: COC(=O)Nc1nc2ccccc2[nH]1]

(10-4) chlorfenazole of the formula

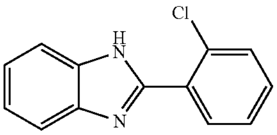 [SMILES: Clc1ccccc1-c1nc2ccccc2[nH]1]

(10-5) fuberidazole (known from DE-A 12 09 799) of the formula

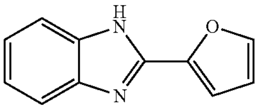 [SMILES: c1coc(-c2nc3ccccc3[nH]2)c1]

(10-6) thiabendazole (known from U.S. Pat. No. 3,206,468) of the formula

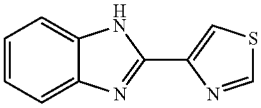 [SMILES: c1ccc2[nH]c(-c3cscn3)nc2c1]

The formula (IX) embraces the following preferred mixing partners of group (11):

(11-1) diethofencarb (known from EP-A 0 078 663) of the formula

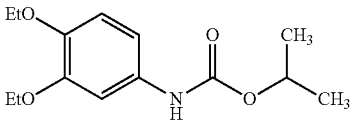 [SMILES: CCOc1ccc(NC(=O)OC(C)C)cc1OCC]

(11-2) propamocarb (known from U.S. Pat. No. 3,513,241) of the formula

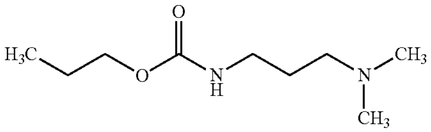

(11-3) propamocarb-hydrochloride (known from U.S. Pat. No. 3,513,241) of the formula

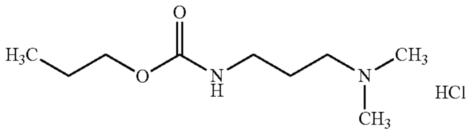

(11-4) propamocarb-fosetyl of the formula

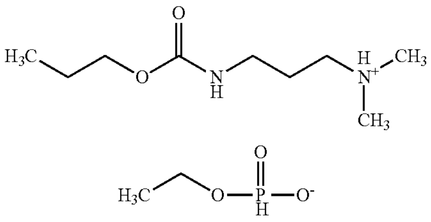

Preferred mixing partners of group (12) are (12-1) captafol (known from U.S. Pat. No. 3,178,447) of the formula

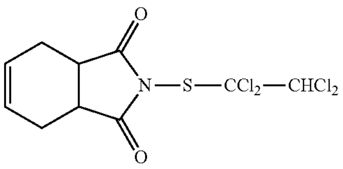

(12-2) captan (known from U.S. Pat. No. 2,553,770) of the formula

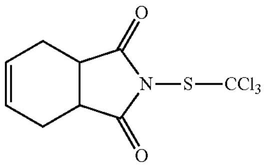

(12-3) folpet (known from U.S. Pat. No. 2,553,770) of the formula

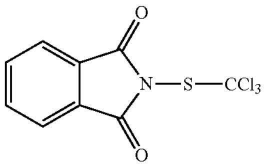

(12-4) iprodione (known from DE-A 21 49 923) of the formula

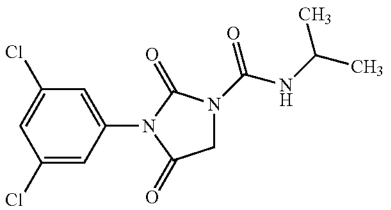 [SMILES: CC(C)NC(=O)N1CC(=O)N(c2cc(Cl)cc(Cl)c2)C1=O]

(12-5) procymidone (known from DE-A 20 12 656) of the formula

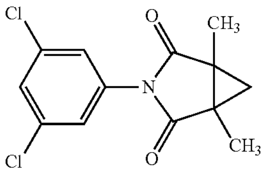 [SMILES: CC12CC1(C)C(=O)N(c1cc(Cl)cc(Cl)c1)C2=O]

(12-6) vinclozolin (known from DE-A 22 07 576) of the formula

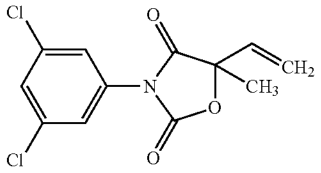 [SMILES: C=CC1(C)OC(=O)N(c2cc(Cl)cc(Cl)c2)C1=O]

Preferred mixing partners of group (13) are (13-1) dodine (known from GB 11 03 989) of the formula

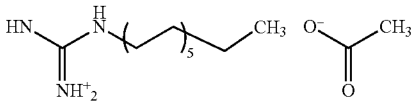

(13-2) guazatine (known from GB 11 14 155)

(13-3) iminoctadine triacetate (known from EP-A 0 155 509) of the formula

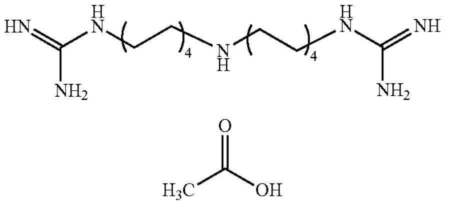

Preferred mixing partner of the group (14) are (14-1) cyazofamid (known from EP-A 0 298 196) of the formula

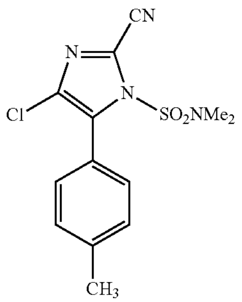

(14-2) prochloraz (known from DE-A 24 29 523) of the formula

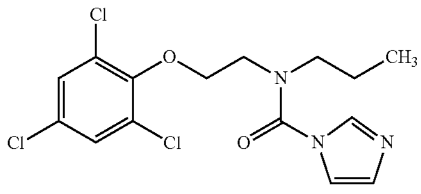 [SMILES: CCCN(CCOc1c(Cl)cc(Cl)cc1Cl)C(=O)n1ccnc1]

(14-3) triazoxide (known from DE-A 28 02 488) of the formula

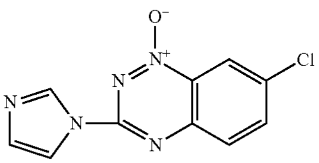 [SMILES: [O-][n+]1nc(-n2ccnc2)nc2ccc(Cl)cc21]

(14-4) pefurazoate (known from EP-A 0 248 086) of the formula

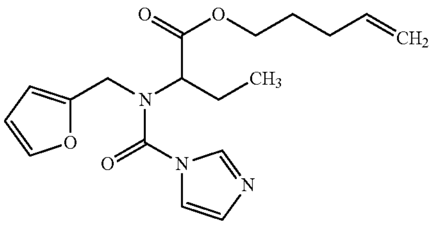 [SMILES: C=CCCCOC(=O)C(CC)N(Cc1ccco1)C(=O)n1ccnc1]

The formula (X) embraces the following preferred mixing partners of group (15):

(15-1) aldimorph (known from DD 140 041) of the formula

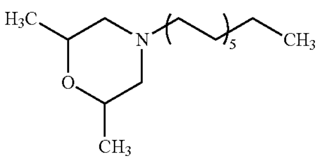

(15-2) tridemorph (known from GB 988 630) of the formula

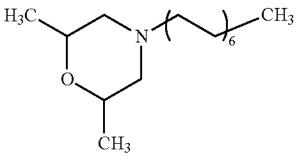

(15-3) dodemorph (known from DE-A 25 432 79) of the formula

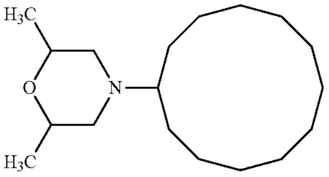 [SMILES: CC1CN(C2CCCCCCCCCCC2)CC(C)O1]

(15-4) fenpropimorph (known from DE-A 26 56 747) of the formula

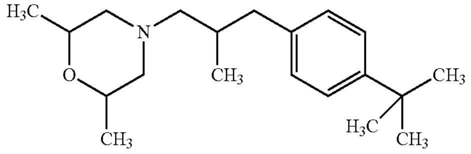 [SMILES: CC(Cc1ccc(C(C)(C)C)cc1)CN1CC(C)OC(C)C1]

(15-5) dimethomorph (known from EP-A 0 219 756) of the formula

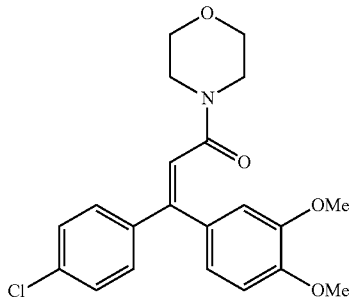 [SMILES: COc1ccc(/C(=C\C(=O)N2CCOCC2)c2ccc(Cl)cc2)cc1OC]

The formula (XI) embraces the following preferred mixing partners of group (16):

(16-1) fenpiclonil (known from EP-A 0 236 272) of the formula

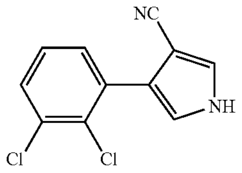 [SMILES: N#Cc1c[nH]cc1-c1cccc(Cl)c1Cl]

(16-2) fludioxonil (known from EP-A 0 206 999) of the formula

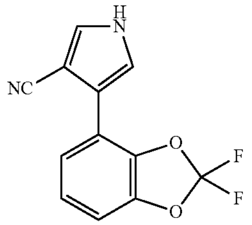 [SMILES: N#Cc1c[nH]cc1-c1cccc2c1OC(F)(F)O2]

(16-3) pyrrolnitrin (known from JP 65-25876) of the formula

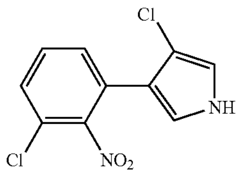 [SMILES: O=[N+]([O-])c1c(Cl)cccc1-c1c[nH]cc1Cl]

Preferred mixing partners of group (17) are (17-1) fosetyl-Al (known from DE-A 24 56 627) of the formula

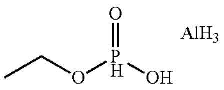

(17-2) phosphonic acid (known chemical) of the formula

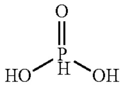

The formula (XII) embraces the following preferred mixing partners of group (18) which are known from WO 96/23793 and can in each case be present as E or Z isomers. Accordingly, compounds of the formula (XII) can be present as a mixture of different isomers or else in the form of a single isomer. Preference is given to compounds of the formula (XII) in the form of their E isomers:

(18-1) the compound 2-(2,3-dihydro-1H-inden-5-yl)-N-[2-(3,4-dimethoxyphenyl)ethyl]-2-(methoxy-imino)acetamide of the formula

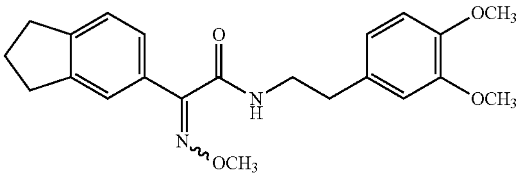 [SMILES: CON=C(C(=O)NCCc1ccc(OC)c(OC)c1)c1ccc2c(c1)CCC2]

(18-2) the compound N-[2-(3,4-dimethoxyphenyl)ethyl]-2-(methoxyimino)-2-(5,6,7,8-tetrahydro-naphthalen-2-yl) acetamide of the formula

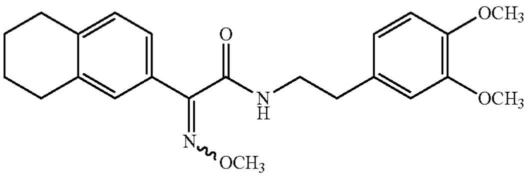 [SMILES: CON=C(C(=O)NCCc1ccc(OC)c(OC)c1)c1ccc2c(c1)CCCC2]

(18-3) the compound 2-(4-chlorophenyl)-N-[2-(3,4-dimethoxyphenyl)ethyl]-2-(methoxyimino)-acetamide of the formula

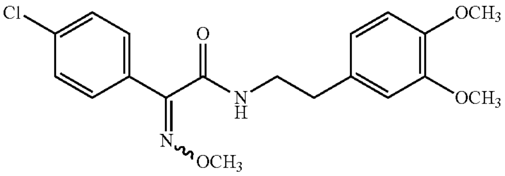

(18-4) the compound 2-(4-bromophenyl)-N-[2-(3,4-dimethoxyphenyl)ethyl]-2-(methoxyimino)-acetamide of the formula

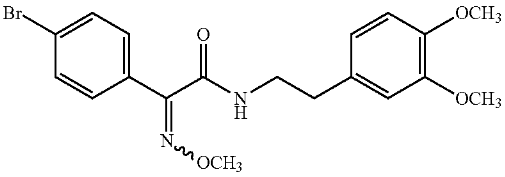 [SMILES: CON=C(C(=O)NCCc1ccc(OC)c(OC)c1)c1ccc(Cl)cc1]

(18-5) the compound 2-(4-methylphenyl)-N-[2-(3,4-dimethoxyphenyl)ethyl]-2-(methoxyimino)-acetamide of the formula

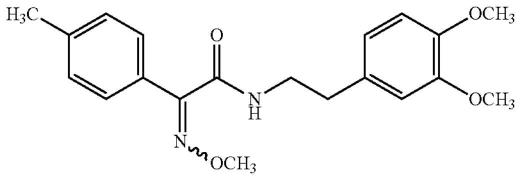 [SMILES: CON=C(C(=O)NCCc1ccc(OC)c(OC)c1)c1ccc(C)cc1]

(18-6) the compound 2-(4-ethylphenyl)-N-[2-(3,4-dimethoxyphenyl)ethyl]-2-(methoxyimino)-acetamide of the formula

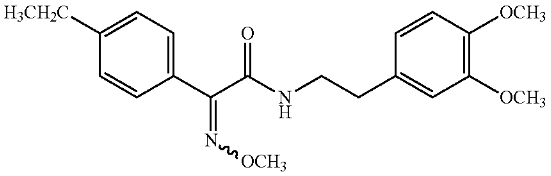

Preferred mixing partners of group (19) are (19-1) acibenzolar-S-methyl (known from EP-A 0 313 512) of the formula

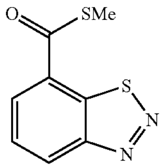 [SMILES: CSC(=O)c1cccc2nnsc12]

(19-2) chlorothalonil (known from U.S. Pat. No. 3,290,353) of the formula

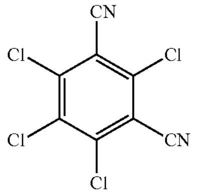 [SMILES: N#Cc1c(Cl)c(Cl)c(Cl)c(C#N)c1Cl]

(19-3) cymoxanil (known from DE-A 23 12 956) of the formula

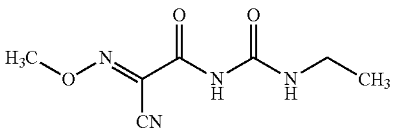

(19-4) edifenphos (known from DE-A 14 93 736) of the formula

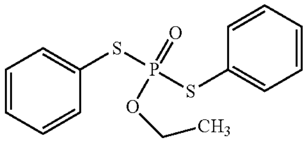 [SMILES: CCOP(=O)(Sc1ccccc1)Sc1ccccc1]

(19-5) famoxadone (known from EP-A 0 393 911) of the formula

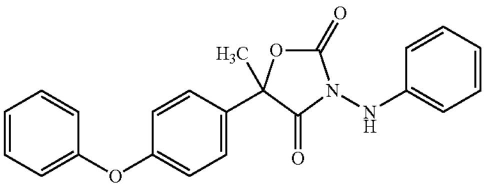 [SMILES: CC1(c2ccc(Oc3ccccc3)cc2)OC(=O)N(Nc2ccccc2)C1=O]

(19-6) fluazinam (known from EP-A 0 031257) of the formula

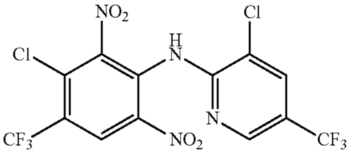 [SMILES: O=[N+]([O-])c1cc(C(F)(F)F)c(Cl)c([N+](=O)[O-])c1Nc1ncc(C(F)(F)F)cc1Cl]

(19-7) copper oxychloride (19-9) oxadixyl (known from DE-A 30 30 026) of the formula

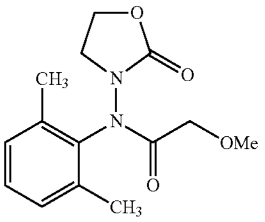 [SMILES: COCC(=O)N(c1c(C)cccc1C)N1CCOC1=O]

(19-10) spiroxamine (known from DE-A 37 35 555) of the formula

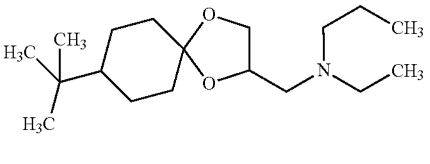 [SMILES: CCCN(CC)CC1COC2(CCC(C(C)(C)C)CC2)O1]

(19-11) dithianon (known from JP-A 44-29464) of the formula

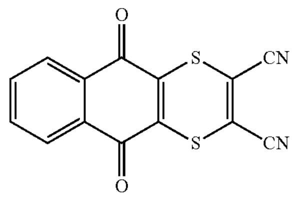 [SMILES: N#Cc1sc2c(=O)c3ccccc3c(=O)c=2sc1C#N]

(19-12) metrafenone (known from EP-A 0 897 904) of the formula

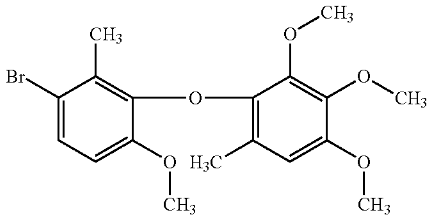 [SMILES: COc1ccc(Br)c(C)c1Oc1c(C)cc(OC)c(OC)c1OC]

(19-13) fenamidone (known from EP-A 0 629 616) of the formula

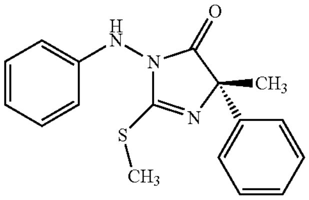 [SMILES: CSC1=N[C@@](C)(c2ccccc2)C(=O)N1Nc1ccccc1]

(19-14) 2,3-dibutyl-6-chlorothieno[2,3-d]pyrimidin-4(3H) one (known from WO 99/14202) of the formula

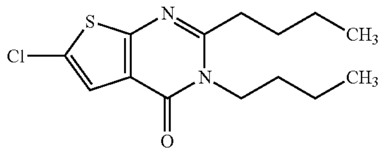 [SMILES: CCCCc1nc2sc(Cl)cc2c(=O)n1CCCC]

(19-15) probenazole (known from U.S. Pat. No. 3,629,428) of the formula

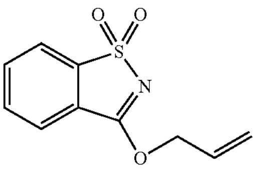

(19-16) isoprothiolane (known from U.S. Pat. No. 3,856, 814) of the formula

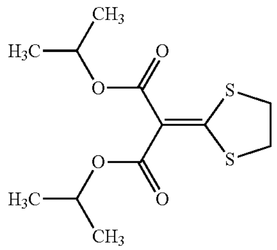 [SMILES: CC(C)OC(=O)C(C(=O)OC(C)C)=C1SCCS1]

(19-17) kasugamycin (known from GB 1094 567) of the formula

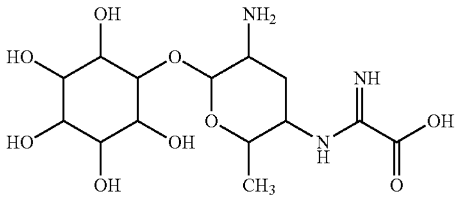 [SMILES: CC1OC(OC2C(O)C(O)C(O)C(O)C2O)C(N)CC1NC(=N)C(=O)O]

(19-18) phthalide (known from JP-A 57-55844) of the formula

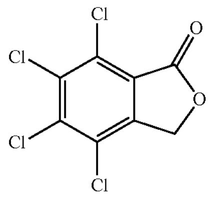 [SMILES: O=C1OCc2c(Cl)c(Cl)c(Cl)c(Cl)c21]

(19-19) ferimzone (known from EP-A 0 019 450) of the formula

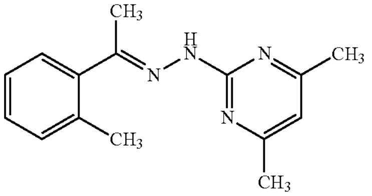 [SMILES: C/C(=N\Nc1nc(C)cc(C)n1)c1ccccc1C]

(19-20) tricyclazole (known from DE-A 22 50 077) of the formula

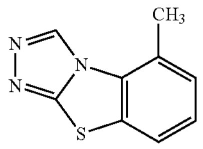

(19-21) N-({4-[(cyclopropylamino)carbonyl] phenyl}sulphonyl)-2-methoxybenzamide of the formula

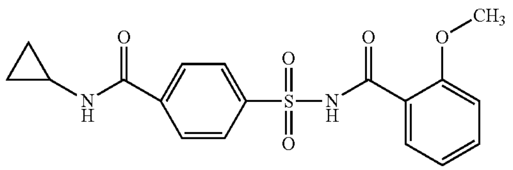 [SMILES: COc1ccccc1C(=O)NS(=O)(=O)c1ccc(C(=O)NC2CC2)cc1]

Preferred mixing partners of group (20) are (20-1) pencycuron (known from DB-A 27 32 257) of the formula

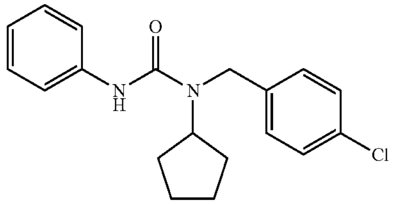 [SMILES: O=C(Nc1ccccc1)N(Cc1ccc(Cl)cc1)C1CCCC1]

(20-2) thiophanate-methyl (known from DE-A 18 06 123) of the formula

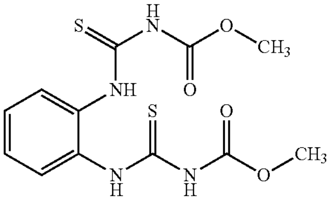 [SMILES: COC(=O)NC(=S)Nc1ccccc1NC(=S)NC(=O)OC]

(20-3) thiophanate-ethyl (known from DE-A 18 06 123) of the formula

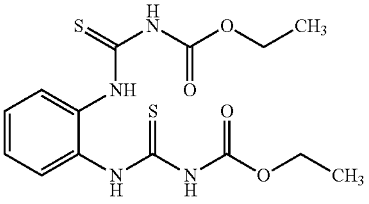 [SMILES: CCOC(=O)NC(=S)Nc1ccccc1NC(=S)NC(=O)OCC]

Preferred mixing partners of group (21) are (21-1) fenoxanil (known from EP-A 0 262 393) of the formula

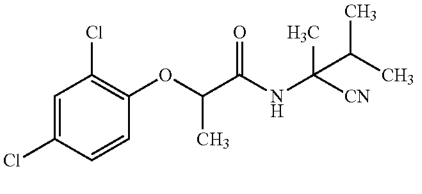 [SMILES: CC(Oc1ccc(Cl)cc1Cl)C(=O)NC(C)(C#N)C(C)C]

(21-2) dicylcomat (known from JP-A 7-206608) of the formula

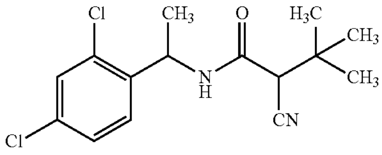 [SMILES: CC(NC(=O)C(C#N)C(C)(C)C)c1ccc(Cl)cc1Cl]

Preferred mixing partners of group (22) are (22-1) 5-chloro-N-[(1S)-2,2,2-trifluoro-1-methylethyl]-6-(2,4,6-trifluorophenyl)[1,2,4]triazolo-[1,5-a]pyrimidine-7-amine (known from U.S. Pat. No. 5,986,135) of the formula

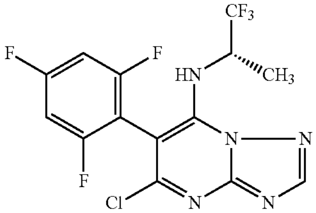 [SMILES: C[C@H](Nc1c(-c2c(F)cc(F)cc2F)c(Cl)nc2ncnn12)C(F)(F)F]

(22-2) 5-chloro-N-[(1R)-1,2-dimethylpropyl]-6-(2,4,6-trifluorophenyl)[1,2,4]triazolo[1,5-a]-pyrimidine-7-amine (known from WO 02/38565) of the formula

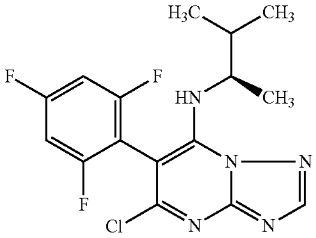 [SMILES: CC(C)[C@@H](C)Nc1c(-c2c(F)cc(F)cc2F)c(Cl)nc2ncnn12]

(22-3) 5-chloro-6-(2-chloro-6-fluorophenyl)-7-(4-methylpiperidin-1-yl)[1,2,4]triazolo[1,5-a]-pyrimidine (known from U.S. Pat. No. 5,593,996) of the formula

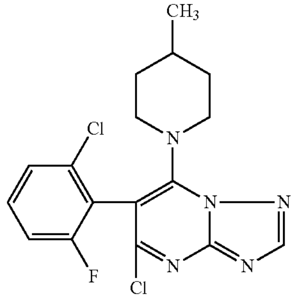 [SMILES: CC1CCN(c2c(-c3c(F)cccc3Cl)c(Cl)nc3ncnn23)CC1]

Preferred mixing partners of group (23) are (23-1) 2-butoxy-6-iodo-3-propylbenzopyran-4-one (known from WO 03/014103) of the formula

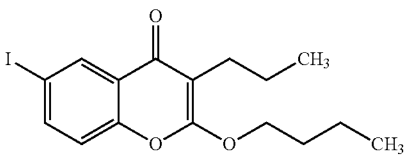 [SMILES: CCCCOc1oc2ccc(I)cc2c(=O)c1CCC]

(23-2) 2-ethoxy-6-iodo-3-propylbenzopyran-4-one (known from WO 03/014103) of the formula

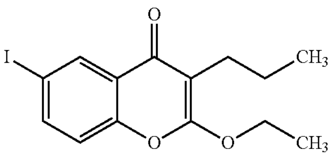

(23-3) 6-iodo-2-propoxy-3-propylbenzopyran-4-one (known from WO 03/014103) of the formula

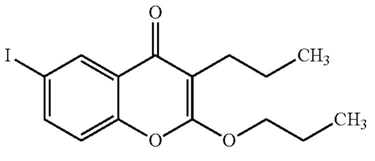 [SMILES: CCCOc1oc2ccc(I)cc2c(=O)c1CCC]

(23-4) 2-but-2-ynyloxy-6-iodo-3-propylbenzopyran-4-one (known from WO 03/014103) of the formula

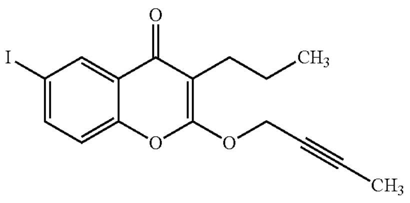 [SMILES: CC#CCOc1oc2ccc(I)cc2c(=O)c1CCC]

(23-5) 6-iodo-2-(1-methylbutoxy)-3-propylbenzopyran-4-one (known from WO 03/014103) of the formula

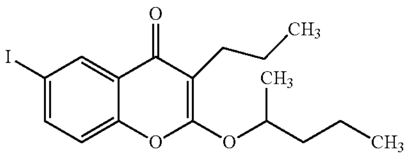 [SMILES: CCCc1c(OC(C)CCC)oc2ccc(I)cc2c1=O]

(23-6) 2-but-3-enyloxy-6-iodobenzopyran-4-one (known from WO 03/014103) of the formula

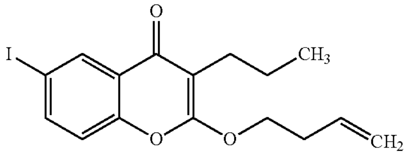

(23-7) 3-butyl-6-iodo-2-isopropoxybenzopyran-4-one (known from WO 03/014103) of the formula

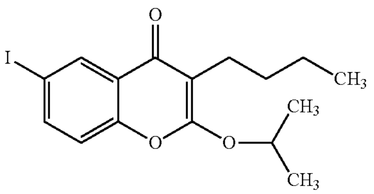 [SMILES: CCCCc1c(OC(C)C)oc2ccc(I)cc2c1=O]

Preferred mixing partners of group (24) are (24-1) N-(3',4'-dichloro-5-fluoro-1,1'-biphenyl-2-yl)-3-(difluoromethyl)-1-methyl-1H-pyrazole-4-carboxamide (known from WO 03/070705) of the formula

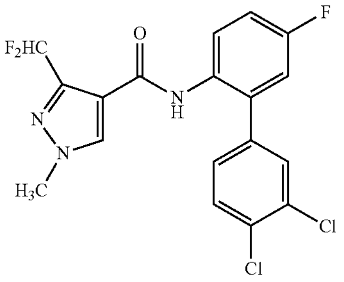 [SMILES: Cn1cc(C(=O)Nc2ccc(F)cc2-c2ccc(Cl)c(Cl)c2)c(C(F)F)n1]

(24-2) 3-(difluoromethyl)-N-{3'-fluoro-4'-[(E)-(methoxyimino)methyl]-1,1'-biphenyl-2-yl}-methyl-1H-pyrazole-4-carboxamide (known from WO 02/08197) of the formula

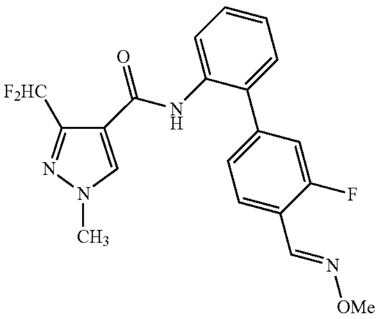 [SMILES: CO/N=C/c1ccc(-c2ccccc2NC(=O)c2cn(C)nc2C(F)F)cc1F]

(24-3) 3-(trifluoromethyl)-N-{3'-fluoro-4'-[(E)-(methoxyimino)methyl]-1,1'-biphenyl-2-yl}-1-methyl-1H-pyrazole-4-carboxamide (known from WO 02/08197) of the formula

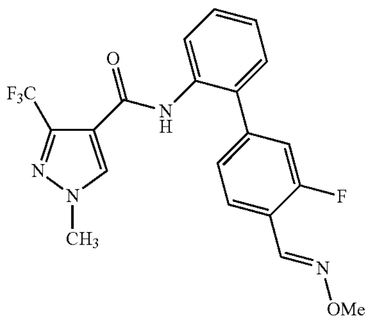 [SMILES: CO/N=C/c1ccc(-c2ccccc2NC(=O)c2cn(C)nc2C(F)(F)F)cc1F]

(24-4) N-(3',4'-dichloro-1,1'-biphenyl-2-yl)-5-fluoro-1,3-dimethyl-1H-pyrazole-4-carboxamide (known from WO 00/14701) of the formula

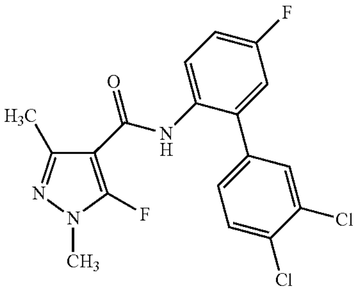 [SMILES: Cc1nn(C)c(F)c1C(=O)Nc1ccc(F)cc1-c1ccc(Cl)c(Cl)c1]

(24-5) N-(4'-chloro-3'-fluoro-1,1'-biphenyl-2-yl)-2-methyl-4-trifluoromethyl)-1,3-thiazole-5-carboxamide (known from WO 03/066609) of the formula

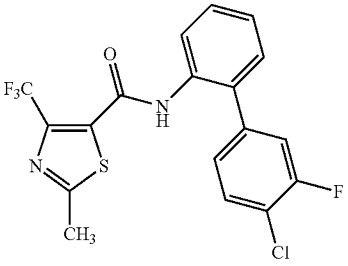 [SMILES: Cc1nc(C(F)(F)F)c(C(=O)Nc2ccccc2-c2ccc(Cl)c(F)c2)s1]

(24-6) N-(4'-chloro-1,1'-biphenyl-2-yl)-4-(difluoromethyl)-2-methyl-1,3-thiazole-5-carboxamide (known from WO 03/066610) of the formula

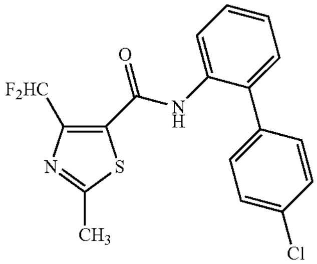 [SMILES: Cc1nc(C(F)F)c(C(=O)Nc2ccccc2-c2ccc(Cl)cc2)s1]

(24-7) N-(4'-bromo-1,1'-biphenyl-2-yl)-4-(difluoromethyl)-2-methyl-1,3-thiazole-5-carboxamide (known from WO 03/066610) of the formula

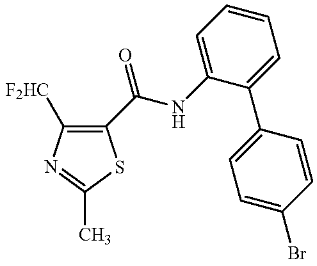 [SMILES: Cc1nc(C(F)F)c(C(=O)Nc2ccccc2-c2ccc(Br)cc2)s1]

(24-8) 4-(difluoromethyl)-2-methyl-N-[4'-(trifluoromethyl)-1,1'-biphenyl-2-yl]-1,3-thiazole-5-carboxamide (known from WO 03/066610) of the formula

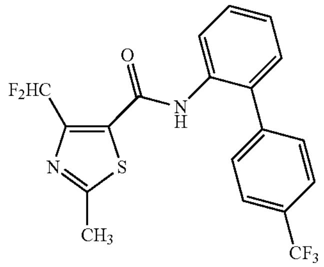 [SMILES: Cc1nc(C(F)F)c(C(=O)Nc2ccccc2-c2ccc(C(F)(F)F)cc2)s1]

Compound (6-7), carpropamid, has three asymmetrically substituted carbon atoms. Accordingly, compound (6-7) can be present as a mixture of different isomers or else in the form of a single component. Particular preference is given to the compounds (1S,3R)-2,2-dichloro-N-[(1R)-1-(4-chlorophenyl)ethyl]-1-ethyl-3-methylcyclopropanecarboxamide of the formula

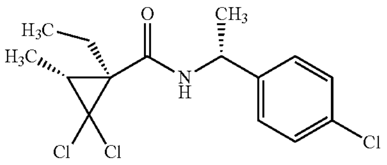 [SMILES: CC[C@@]1(C(=O)N[C@H](C)c2ccc(Cl)cc2)[C@@H](C)C1(Cl)Cl]

and (1R,3S)-2,2-dichloro-N-[(1R)-1-(4-chlorophenyl)ethyl]-1-ethyl-3-methylcyclopropanecarboxamide of the formula

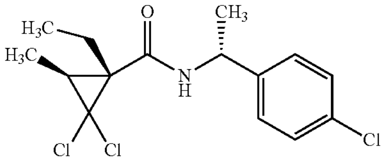 [SMILES: CC[C@]1(C(=O)N[C@H](C)c2ccc(Cl)cc2)[C@H](C)C1(Cl)Cl]

The following fungicidal active compounds are particularly preferred:

(2-1) azoxystrobin (2-2) fluoxastrobin (2-3) (2E)-2-(2-{[6-(3-chloro-2-methylphenoxy)-5-fluoro-4-pyrimidinyl]oxy}phenyl)-2-(methoxyimino)-N-methylethanamide (2-4) trifloxystrobin (2-5) (2E)-2-(methoxyimino)-N-methyl-2-(2-{[({(1E)-1-[3-(trifluoromethyl)-phenyl]ethylidene}amino)oxy]methyl}phenyl)ethanamide (2-6) (2E)-2-(methoxyimino)-N-methyl-2-{2-[(E)-({1-[3-(trifluoromethyl)phenyl]-ethoxy}imino)methyl]phenyl}ethanamide (2-8) 5-methoxy-2-methyl-4-(2-{[({(1E)-1-[3-(trifluoromethyl)phenyl]ethylidene}-amino)oxy]methyl}phenyl)-2,4-dihydro-3H-1,2,4-triazol-3-one (2-9) kresoxim-methyl (2-10) dimoxystrobin (2-11) picoxystrobin
(2-12) pyraclostrobin
(2-13) metominostrobin
(3-3) propiconazole
(3-4) difenoconazole
(3-6) cyproconazole
(3-7) hexaconazole
(3-8) penconazole
(3-9) myclobutanil
(3-10) tetraconazole
(3-13) flusilazole
(3-15) prothioconazole
(3-16) fenbuconazole
(3-17) tebuconazole
(3-21) bitertanol
(3-22) triadimenol
(3-23) triadimefon
(3-12) epoxiconazole
(3-19) metconazole
(3-24) fluquinconazole
(4-1) dichlofluanid
(4-2) tolylfluanid
(5-1) iprovalicarb
(5-3) benthiavalicarb
(6-2) boscalid
(6-5) ethaboxam
(6-6) fenhexamid
(6-7) carpropamid
(6-8) 2-chloro-4-[(2-fluoro-2-methylpropenoyl)amino]-N,N-dimethylbenzamide
(6-9) picobenzamid
(6-10) zoxamide
(6-11) 3,4-dichloro-N-(2-cyanophenyl)isothiazole-5-carboxamide
(6-14) penthiopyrad
(6-16) N-[2-(1,3-dimethylbutyl)phenyl]-1-methyl-4-(trifluoromethyl)-1H-pyrrole-3-carboxamide
(7-1) mancozeb
(7-2) maneb
(7-4) propineb
(7-5) thiram
(7-6) zineb
(8-1) benalaxyl
(8-2) furalaxyl
(8-3) metalaxyl
(8-4) metalaxyl-M
(8-5) benalaxyl-M
(9-1) cyprodinil
(9-2) mepanipyrim
(9-3) pyrimethanil
(10-1) 6-chloro-5-[(3,5-dimethylisoxazol-4-yl)sulphonyl]-2,2-difluoro-5H-[1,3]dioxolo[4,5-f]-benzimidazole
(10-3) carbendazim
(11-1) diethofencarb
(11-2) propamocarb
(11-3) propamocarb-hydrochloride
(11-4) propamocarb-fosetyl
(12-2) captan
(12-3) folpet
(12-4) iprodione
(12-5) procymidone
(13-1) dodine
(13-2) guazatine
(13-3) iminoctadine triacetate
(14-1) cyazofamid
(14-2) prochloraz
(14-3) triazoxide
(15-5) dimethomorph
(15-4) fenpropimorph
(16-2) fludioxonil
(17-1) fosetyl-Al
(17-2) phosphonic acid
(19-1) acibenzolar-S-methyl
(19-2) chlorothalonil
(19-3) cymoxanil
(19-5) famoxadone
(19-7) copper oxychloride
(19-6) fluazinam
(19-9) oxadixyl
(19-10) spiroxamine
(19-13) fenamidone
(20-1) pencycuron
(20-2) thiophanate-methyl
(22-1) 5-chloro-N-[(1S)-2,2,2-trifluo-1-methylethyl]-6-(2,4,6-trifluorophenyl)[1,2,4]-triazolo[1,5-a]pyrimidine-7-amine
(22-2) 5-chloro-N-[(1R)-1,2-dimethylpropyl]-6-(2,4,6-trifluorophenyl)[1,4]triazolo[1,5-a]-pyrimidine-7-amine
(23-1) 2-butoxy-6-iodo-3-propylbenzopyran-4-one
(23-2) 2-ethoxy-6-iodo-3-propylbenzopyran-4-one
(23-3) 6-iodo-2-propoxy-3-propylbenzopyran-4-one
(24-1) N-(3',4'-dichloro-5-fluoro-1,1'-biphenyl-2-yl)-3-(difluoromethyl)-1-methyl-1H-pyrazole-4-carboxamide
(24-3) 3-(trifluoromethyl)-N-{(3'-fluoro-4'-[(E)-(methoxyimino)methyl]-1,1'-biphenyl-2-yl}-1-methyl-1H-pyrazole-4-carboxamide
(24-7) N-(4'-bromo-1,1'-biphenyl-2-yl)-4-(difluoromethyl)-2-methyl-1,3-thiazole-5-carboxamide Very particularly preferred mixing partners are the following active compounds:
(2-2) fluoxastrobin
(2-3) (2E)-2-(2-{[6-(3-chloro-2-methylphenoxy)-5-fluoro-4-pyrimidinyl]oxy}phenyl)-2-(methoxyimino)-N-methylethanamide
(2-4) trifloxystrobin
(3-15) prothioconazole
(3-17) tebuconazole
(3-21) bitertanol
(3-22) triadimenol
(3-24) fluquinconazole
(4-1) dichlofluanid
(4-2) tolylfluanid
(5-1) iprovalicarb
(6-6) fenhexamid
(6-7) carpropamid
(6-9) picobenzamid
(6-14) penthiopyrad
(7-4) propineb
(8-4) metalaxyl-M
(8-5) benalaxyl-M
(9-3) pyrimethanil
(10-3) carbendazim
(11-4) propamocarb-fosetyl
(12-4) iprodione
(14-2) prochloraz
(14-3) triazoxide
(16-2) fludioxonil
(19-10) spiroxamine
(24-1) N-(3',4'-dichloro-5-fluoro-1,1'-biphenyl-2-yl)-3-(difluoromethyl)-1-methyl-1H-pyrazole-4-carboxamide Preference is given to safener/fungicide combinations used according to the invention comprising a preferred compound of group 1 and a preferred compound of groups 2 to 24.

Particular preference is given to safener/fungicide combinations used according to the invention comprising a particularly preferred compound of group 1 and a particularly preferred compound of groups 2 to 24.

Very particular preference is given to safener/fungicide combinations used according to the invention comprising a very particularly preferred compound of group 1 and a very particularly preferred compound of groups 2 to 24.

Especially preferred are the safener/fungicide combinations listed below.

1. Combinations of cloquintocet-mexyl (S1) with particularly preferred fungicidally active compounds of groups 2 to 24:
   (S1)/(2-1), (S1)/(2-2), (S1)/(2-3), (S1)/(2-4), (S1)/(2-5), (S1)/(2-6), (S1)/(2-8), (S1)/(2-9), (S1)/(2-10), (S1)/(2-11), (S1)/(2-12), (S1)/(2-13);
   (S1)/(3-3), (S1)/(3-4), (S1)/(3-6), (S1)/(3-7), (S1)/(3-8), (S1)/(3-9), (S1)/(3-10), (S1)/(3-12), (S1)/(3-13), (S1)/(3-S15), (S1)/(3-16), (S1)/(3-17), (S1)/(3-19), (S1)/(3-21), (S1)/(3-22),
   (S1)/(3-23), (S1)/(3-24);
   (S1)/(4-1), (S1)/(4-2);
   (S1)/(5-1), (S1)/(5-3);
   (S1)/(6-2), (S1)/(6-5), (S1)/(6-6), (S1)/(6-7), (S1)/(6-8), (S1)/(6-9), (S1)/(6-10), (S1)/(6-11), (S1)/(6-14), (S1)/(6-16);
   (S1)/(7-1), (S1)/(7-2), (S1)/(7-4), (S1)/(7-5), (S1)/(7-6);
   (S1)/(8-1), (S1)/(8-2), (S1)/(8-3), (S1)/(8-4), (S1)/(8-5);
   (S1)/(9-1), (S1)/(9-2), (S1)/(9-3);
   (S1)/(10-1), (S1)/(10-3);
   (S1)/(11-1), (S1)/(11-2), (S1)/(11-3), (S1)/(11-4);
   (S1)/(12-2), (S1)/(12-3), (S1)/(12-4), (S1)/(12-5);
   (S1)/(13-1), (S1)/(13-2), (S1)/(13-3);
   (S1)/(14-1), (S1)/(14-2), (S1)/(14-3);
   (S1)/(15-4), (S1)/(15-5);
   (S1)/(16-2);
   (S1)/(17-1), (S1)/(17-2);
   (S1)/(19-1), (S1)/(19-2), (S1)/(19-3), (S1)/(19-5), (S1)/(19-6), (S1)/(19-7), (S1)/(19-9), (S1)/(19-10), (S1)/(19-13);
   (S1)/(20-1), (S1)/(20-2);
   (S1)/(22-1), (S1)/(22-2);
   (S1)/(23-1), (S1)/(23-2), (S1)/(23-3);
   (S1)/(24-1), (S1)/(24-3), (S1)/(24-7);
2. Combinations of fenchlorazole-ethyl (S2) with particularly preferred fungicidally active compounds of groups 2 to 24:
   (S2)/(2-1), (S2)/(2-2), (S2)/(2-3), (S2)/(2-4), (S2)/(2-5), (S2)/(2-6), (S2)/(2-8), (S2)/(2-9), (S2)/(2-10), (S2)/(2-11), (S2)/(2-12), (S2)/(2-13);
   (S2)/(3-3), (S2)/(3-4), (S2)/(3-6), (S2)/(3-7), (S2)/(3-8), (S2)/(3-9), (S2)/(3-10), (S2)/(3-12), (S2)/(3-13), (S2)/(3-15), (S2)/(3-16), (S2)/(3-1 7), (S2)/(3-19), (S2)/(3-21), (S2)/(3-22),
   (S2)/(3-23), (S2)/(3-24);
   (S2)/(4-1), (S2)/(4-2);
   (S2)/(5-1), (S2)/(5-3);
   (S2)/(6-2), (S2)/(6-5), (S2)/(6-6), (S2)/(6-7), (S2)/(6-8), (S2)/(6-9), (S2)/(6-10), (S2)/(6-11), (S2)/(6-14), (S2)/(6-16);
   (S2)/(7-1), (S2)/(7-2), (S2)/(7-4), (S2)/(7-5), (S2)/(7-6);
   (S2)/(8-1), (S2)/(8-2), (S2)/(8-3), (S2)/(8-4), (S2)/(8-5);
   (S2)/(9-1), (S2)/(9-2), (S2)/(9-3);
   (S2)/(10-1), (S2)/(10-3);
   (S2)/(11-1), (S2)/(11-2), (S2)/(11-3), (S2)/(11-4);
   (S2)/(12-2), (S2)/(12-3), (S2)/(12-4), (S2)/(12-5);
   (S2)/(13-1), (S2)/(13-2), (S2)/(13-3);
   (S2)/(14-1), (S2)/(14-2), (S2)/(14-3);
   (S2)/(15-4), (S2)/(15-5);
   (S2)/(16-2);
   (S2)/(1 7-1), (S2)/(17-2);
   (S2)/(19-1), (S2)/(19-2), (S2)/(19-3), (S2)/(19-5), (S2)/(19-6), (S2)/(19-7), (S2)/(19-9), (S2)/(19-10), (S2)/(19-13);
   (S2)/(20-1), (S2)/(20-2);
   (S2)/(22-1), (S2)/(22-2);
   (S2)/(23-1), (S2)/(23-2), (S2)/(23-3);
   (S2)/(24-1), (S2)/(24-3), (S1)/(24-7);
3. Combinations of isoxadifen-ethyl (S3) with particularly preferred fungicidally active compounds of groups 2 to 24:
   (S3)/(2-1), (S3)/(2-2), (S3)/(2-3), (S3)/(2-4), (S3)/(2-5), (S3)/(2-6), (S3)/(2-8), (S3)/(2-9), (S3)/(2-10), (S3)/(2-11), (S3)/(2-12), (S3)/(2-13);
   (S3)/(3-3), (S3)/(3-4), (S3)/(3-6), (S3)/(3-7), (S3)/(3-8), (S3)/(3-9), (S3)/(3-10), (S3)/(3-12), (S3)/(3-13), (S3)/(3-15), (S3)/(3-16), (S3)/(3-17), (S3)/(3-19), (S3)/(3-21), (S3)/(3-22), (S3)/(3-23), (S3)/(3-24);
   (S3)/(4-1), (S3)/(4-2);
   (S3)/(5-1), (S3)/(5-3);
   (S3)/(6-2), (S3)/(6-5), (S3)/(6-6), (S3)/(6-7), (S3)/(6-8), (S3)/(6-9), (S3)/(6-10), (S3)/(6-11), (S3)/(6-14), (S3)/(6-16);
   (S3)/(7-1), (S3)/(7-2), (S3)/(7-4), (S3)/(7-5), (S3)/(7-6);
   (S3)/(8-1), (S3)/(8-2), (S3)/(8-3), (S3)/(8-4), (S3)/(8-5);
   (S3)/(9-1), (S3)/(9-2), (S3)/(9-3);
   (S3)/(10-1), (S3)/(10-3);
   (S3)/(11-1), (S3)/(11-2), (S3)/(11-3), (53)/(11-4);
   (S3)/(12-2), (S3)/(12-3), (S3)/(12-4), (S3)/(12-5);
   (S3)/(13-1), (S3)/(13-2), (S3)/(13-3);
   (S3)/(14-1), (S3)/(14-2), (S3)/(14-3);
   (S3)/(15-4), (S3)/(15-5);
   (S3)/(16-2);
   (S3)/(17-1), (S3)/(17-2);
   (S3)/(19-1), (S3)/(19-2), (S3)/(19-3), (S3)/(19-5), (S3)/(19-6), (S3)/(19-7), (83)/(19-9), (S3)/(19-10), (S3)/(19-13);
   (S3)/(20-1), (S3)/(20-2);
   (S3)/(22-1), (S3)/(22-2);
   (S3)/(23-1), (S3)/(23-2), (S3)/(23-3);
   (S3)/(24-1), (S3)/(24-3), (S3)/(24-7);
4. Combinations of mefenpyr-diethyl (S4) with particularly preferred fungicidally active compounds of groups 2 to 24:
   (S4)/(2-1), (S4)/(2-2), (S4)/(2-3), (S4)/(2-4), (S4)/(2-5), (S4)/(2-6), (S4)/(2-8), (S4)/(2-9), (S4)/(2-10), (S4)/(2-1), (S4)/(2-12), (S4)/(2-13);
   (S4)/(3-3), (S4)/(3-4), (S4)/(3-6), (S4)/(3-7), (S4)/(3-8), (S4)/(3-9), (S4)/(3-10), (4)/(3-12), (S4)/(3-13), (S4)/(3-15), (S4)/(3-16), (S4)/(3-17), (S4)/(3-19), (S4)/(3-21), (S4)/(3-22), (S4)/(3-23), (S4)/(3-24);
   (S4)/(4-1), (S4)/(4-2);
   (S4)/(5-1), (S4)/(5-3);
   (S4)/(6-2), (S4)/(6-5), (S4)/(6-6), (S4)/(6-7), (S4)/(6-8), (S4)/(6-9), (S4)/(6-10), (S4)/(6-11), (S4)/(6-14), (S4)/(6-16);
   (S4)/(7-1), (S4)/(7-2), (S4)/(7-4), (S4)/(7-5), (S4)/(7-6);
   (S4)/(8-1), (S4)/(8-2), (S4)/(8-3), (S4)/(8-4), (S4)/(8-5);
   (S4)/(9-1), (S4)/(9-2), (S4)/(9-3);
   (S4)/(10-1), (S4)/(10-3);
   (S4)/(11-1), (S4)/(11-2), (S4)/(11-3), (S4)/(11-4);
   (S4)/(12-2), (S4)/(12-3), (S4)/(12-4), (S4)/(12-5);
   (S4)/(13-1), (S4)/(13-2), (S4)/(13-3);
   (S4)/(14-1), (S4)/(14-2), (S4)/(14-3);

(S4)/(15-4), (S4)/(15-5);
(S4)/(16-2);
(S4)/(17-1), (S4)/(17-2);
(S4)/(19-1), (S4)/(19-2), (S4)/(19-3), (S4)/(19-5), (S4)/(19-6), (S4)/(19-7), (S4)/(19-9), (S4)/(19-10), (S4)/(19-13);
(S4)/(20-1), (S4)/(20-2);
(S4)/(22-1), (S4)/(22-2);
(S4)/(23-1), (S4)/(23-2), (S4)/(23-3);
(S4)/(24-1), (4)/(24-3), (S4)/(24-7);

5. Combinations of furilazole (S5) with particularly preferred fungicidally active compounds of groups 2 to 24:
(S5)/(2-1), (S5)/(2-2), (S5)/(2-3), (S5)/(2-4), (S5)/(2-5), (S5)/(2-6), (5)/(2-8), (S5)/(2-9), (S5)/(2-10), (S5)/(2-11), (S5)/(2-12), (S5)/(2-13);
(S5)/(3-3), (S5)/(3-4), (S5)/(3-6), (S5)/(3-7), (5)/(3-8), (S5)/(3-9), (S5)/(3-10), (S5)/(3-12), (S5)/(3-13), (S5)/(3-15), (S5)/(3-16), (S5)/(3-17), (S5)/(3-19), (S5)/(3-21), (S5)/(3-22), (S5)/(3-23), (S5)/(3-24);
(S5)/(4-1), (S5)/(4-2);
(S5)/(5-1), (S5)/(5-3);
(S5)/(6-2), (S5)/(6-5), (S5)/(6-6), (S5)/(6-7), (S5)/(6-8), (S5)/(6-9), (S5)/(6-10), (S5)/(6-11), (S5)/(6-14), (S5)/(6-16);
(S5)/(7-1), (S5)/(7-2), (S5)/(7-4), (S5)/(7-5), (S5)/(7-6);
(S5)/(8-1), (S5)/(8-2), (S5)/(8-3), (S5)/(8-4), (S5)/(8-5);
(S5)/(9-1), (S5)/(9-2), (S5)/(9-3);
(S5)/(10-1), (S5)/(10-3);
(S5)/(11-1), (S5)/(11-2), (S5)/(11-3), (S5)/(11-4);
(S5)/(12-2), (S5)/(12-3), (S5)/(12-4), (S5)/(12-5);
(S5)/(13-1), (S5)/(13-2), (S5)/(13-3);
(S5)/(14-1), (S5)/(14-2), (S5)/(14-3);
(S5)/(15-4), (S5)/(15-5);
(S5)/(16-2);
(S5)/(17-1), (S5)/(17-2);
(S5)/(19-1), (S5)/(19-2), (S5)/(19-3), (S5)/(19-5), (S5)/(19-6), (S5)/(19-7), (S5)/(19-9), (S5)/(19-10), (S5)/(19-13);
(S5)/(20-1), (S5)/(20-2);
(S5)/(22-1), (S5)/(22-2);
(S5)/(23-1), (S5)/(23-2), (S5)/(23-3);
(S5)/(24-1), (S5)/(24-3), (S5)/(24-7);

6. Combinations of fenclorim (S6) with particularly preferred fungicidally active compounds of groups 2 to 24:
(S6)/(2-1), (S6)/(2-2), (S6)/(2-3), (S6)/(2-4), (S6)/(2-5), (S6)/(2-6), (S6)/(2-8), (S6)/(2-9), (S6)/(2-10), (S6)/(2-11), (S6)/(2-12), (S6)/(2-13);
(S6)/(3-3), (S6)/(3-4), (S6)/(3-6), (S6)/(3-7), (S6)/(3-8), (S6)/(3-9), (S6)/(3-10), (S6)/(3-12), (S6)/(3-13), (S6)/(3-15), (S6)/(3-16), (S6)/(3-17), (S6)/(3-19), (S6)/(3-21), (S6)/(3-22), (S6)/(3-23), (S6)/(3-24);
(S6)/(4-1), (S6)/(4-2);
(S6)/(5-1), (S6)/(5-3);
(S6)/(6-2), (S6)/(6-5), (S6)/(6-6), (S6)/(6-7), (S6)/(6-8), (S6)/(6-9), (S6)/(6-10), (S6)/(6-11), (S6)/(6-14), (S6)/(6-16);
(S6)/(7-1), (S6)/(7-2), (S6)/(7-4), (S6)/(7-5), (S6)/(7-6);
(S6)/(8-1), (S6)/(8-2), (S6)/(8-3), (S6)/(8-4), (S6)/(8-5);
(S6)/(9-1), (S6)/(9-2), (S6)/(9-3);
(S6)/(10-1), (S6)/(10-3);
(S6)/(11-1), (S6)/(11-2), (S6)/(11-3), (S6)/(11-4);
(S6)/(12-2), (S6)/(12-3), (S6)/(12-4), (S6)/(12-5);
(S6)/(13-1), (S6)/(13-2), (S6)/(13-3);
(S6)/(14-1), (S6)/(14-2), (S6)/(14-3);
(S6)/(15-4), (S6)/(15-5);
(S6)/(16-2);
(S6)/(17-1), (S6)/(17-2);

(S6)/(19-1), (S6)/(19-2), (S6)/(19-3), (S6)/(19-5), (S6)/(19-6), (S6)/(19-7), (S6)/(19-9), (S6)/(19-10), (S6)/(19-13);
(S6)/(20-1), (S6)/(20-2);
(S6)/(22-1), (S6)/(22-2);
(S6)/(23-1), (S6)/(23-2), (S6)/(23-3);
(S6)/(24-1), (S6)/(24-3), (S6)/(24-7);

7. Combinations of cumyluron (S7) with particularly preferred fungicidally active compounds of groups 2 to 24:
(S7)/(2-1), (S7)/(2-2), (S7)/(2-3), (S7)/(2-4), (S7)/(2-5), (S7)/(2-6), (S7)/(2-8), (S7)/(2-9), (S7)/(2-10), (S7)/(2-11), (S7)/(2-12), (S7)/(2-13);
(S7)/(3-3), (S7)/(3-4), (S7)/(3-6), (S7)/(3-7), (S7)/(3-8), (S7)/(3-9), (S7)/(3-10), (S7)/(3-12), (S7)/(3-13), (S7)/(3-15), (S7)/(3-16), (S7)/(3-17), (S7)/(3-19), (S7)/(3-21), (S7)/(3-22),
(S7)/(3-23), (S7)/(3-24);
(S7)/(4-1), (S7)/(4-2);
(S7)/(5-1), (S7)/(5-3);
(S7)/(6-2), (S7)/(6-5), (S7)/(6-6), (S7)/(6-7), (S7)/(6-8), (S7)/(6-9), (S7)/(6-10), (S7)/(6-11), (S7)/(6-14), (S7)/(6-16);
(S7)/(7-1), (S7)/(7-2), (S7)/(7-4), (S7)/(7-5), (S7)/(7-6);
(S7)/(8-1), (S7)/(8-2), (S7)/(8-3), (S7)/(8-4), (S7)/(8-5);
(S7)/(9-1), (S7)/(9-2), (S7)/(9-3);
(S7)/(10-1), (S7)/(10-3);
(S7)/(11-1), (S7)/(11-2), (S7)/(11-3), (S7)/(11-4);
(S7)/(12-2), (S7)/(12-3), (S7)/(12-4), (S7)/(12-5);
(S7)/(13-1), (S7)/(13-2), (S7)/(13-3);
(S7)/(14-1), (S7)/(14-2), (S7)/(14-3);
(S7)/(15-4), (S7)/(15-5);
(S7)/(16-2);
(S7)/(17-1), (S7)/(17-2);
(S7)/(19-1), (S7)/(19-2), (S7)/(19-3), (S7)/(19-5), (S7)/(19-6), (S7)/(19-7), (S7)/(19-9), (S7)/(19-10), (S7)/(19-13);
(S7)/(20-1), (S7)/(20-2);
(S7)/(22-1), (S7)/(22-2);
(S7)/(23-1), (S7)/(23-2), (S7)/(23-3);
(S7)/(24-1), (S7)/(24-3), (S7)/(24-7);

8. Combinations of daimuron/dymron (S8) with particularly preferred fungicidally active compounds of groups 2 to 24:
(S8)/(2-1), (S8)/(2-2), (S8)/(2-3), (S8)/(2-4), (S8)/(2-5), (S8)/(2-6), (S8)/(2-8), (S8)/(2-9), (S8)/(2-10), (S8)/(2-11), (S8)/(2-12), (S8)/(2-13);
(S8)/(3-3), (S8)/(3-4), (S8)/(3-6), (S8)/(3-7), (S8)/(3-8), (S8)/(3-9), (S8)/(3-10), (S8)/(3-12), (S8)/(3-13), (S8)/(3-15), (S8)/(3-16), (S8)/(3-17), (S8)/(3-19), (S8)/(3-21), (S8)/(3-22), (S8)/(3-23), (S8)/(3-24);
(S8)/(4-1), (S8)/(4-2);
(S8)/(5-1), (S8)/(5-3);
(S8)/(6-2), (S8)/(6-5), (S8)/(6-6), (S8)/(6-7), (S8)/(6-8), (S8)/(6-9), (S8)/(6-10), (S8)/(6-11), (S8)/(6-14), (S8)/(6-16);
(S8)/(7-1), (S8)/(7-2), (S8)/(7-4), (S8)/(7-5), (S8)/(7-6);
(S8)/(8-1), (S8)/(8-2), (S8)/(8-3), (S8)/(8-4), (S8)/(8-5);
(S5)/(9-1), (S8)/(9-2), (S8)/(9-3);
(S8)/(10-1), (S8)/(10-3);
(S8)/(11-1), (S8)/(11-2), (S8)/(11-3), (S8)/(11-4);
(S8)/(12-2), (S8)/(12-3), (S8)/(12-4), (S8)/(12-5);
(S8)/(13-1), (S8)/(13-2), (S8)/(13-3);
(S8)/(14-1), (S8)/(14-2), (S8)/(14-3);
(S8)/(15-4), (S8)/(15-5);
(S8)/(16-2);
(S8)/(17-1), (S8)/(17-2);

(S8)/(19-1), (S8)/(19-2), (S8)/(19-3), (S8)/(19-5), (S8)/(19-6), (S8)/(19-7), (S8)/(19-9), (S8)/(19-10), (S8)/(19-13);
(S8)/(20-1), (S8)/(20-2);
(S8)/(22-1), (S8)/(22-2);
(S8)/(23-1), (S8)/(23-2), (S8)/(23-3);
(S8)/(24-1), (S8)/(24-3), (S8)/(24-7);

9. Combinations of dimepirate (S9) with particularly preferred fungicidally active compounds of groups 2 to 24:
(S9)/(2-1), (S9)/(2-2), (S9)/(2-3), (S9)/(2-4), (S9)/(2-5), (S9)/(2-6), (S9)/(2-8), (S9)/(2-9), (S9)/(2-10), (S9)/(2-11), (S9)/(2-12), (S9)/(2-13);
(S9)/(3-3), (S9)/(3-4), (S9)/(3-6), (S9)/(3-7), (S9)/(3-8), (S9)/(3-9), (S9)/(3-10), (S9)/(3-12), (S9)/(3-13), (S9)/(3-15), (S9)/(3-16), (S9)/(3-17), (S9)/(3-19), (S9)/(3-21), (S9)/(3-22),
(S9)/(3-23), (S9)/(3-24);
(S9)/(4-1), (S9)/(4-2);
(S9)/(5-1), (S9)/(5-3);
(S9)/(6-2), (S9)/(6-5), (S9)/(6-6), (S9)/(6-7), (S9)/(6-8), (S9)/(6-9), (S9)/(6-10), (S9)/(6-11), (S9)/(6-14), (S9)/(6-16);
(S9)/(7-1), (S9)/(7-2), (S9)/(7-4), (S9)/(7-5), (S9)/(7-6);
(S9)/(8-1), (S9)/(8-2), (S9)/(8-3), (S9)/(8-4), (S9)/(8-5);
(S9)/(9-1), (S9)/(9-2), (S9)/(9-3);
(S9)/(10-1), (S9)/(10-3);
(S9)/(11-1), (S9)/(11-2), (S9)/(11-3), (S9)/(11-4);
(S9)/(12-2), (S9)/(12-3), (S9)/(12-4), (S9)/(12-5);
(S9)/(13-1), (S9)/(13-2), (S9)/(13-3);
(S9)/(14-1), (S9)/(14-2), (S9)/(14-3);
(S9)/(15-4), (S9)/(15-5);
(S9)/(16-2);
(S9)/(17-1), (S9)/(17-2);
(S9)/(19-1), (S9)/(19-2), (S9)/(19-3), (S9)/(19-5), (S9)/(19-6), (S9)/(19-7), (S9)/(19-9),
(S9)/(19-10), (S9)/(19-13);
(S9)/(20-1), (S9)/(20-2);
(S9)/(22-1), (S9)/(22-2);
(S9)/(23-1), (S9)/(23-2), (S9)/(23-3);
(S9)/(24-1), (S9)/(24-3), (S9)/(24-7);

10. Combinations of the compound (I-e-11) (S10) with particularly preferred fungicidally active compounds of groups 2 to 24:
(S10)/(2-1), (S10)/(2-2), (S10)/(2-3), (S10)/(2-4), (S10)/(2-5), (S10)/(2-6), (S10)/(2-8), (S10)/(2-9), (S10)/(2-10), (S10)/(2-11), (S10)/(2-12), (S10)/(2-13);
(S10)/(3-3), (S10)/(3-4), (S10)/(3-6), (S10)/(3-7), (S10)/(3-8), (S10)/(3-9), (S10)/(3-10), (S10)/(3-12), (S10)/(3-13), (S10)/(3-15), (S10)/(3-16), (S10)/(3-17), (S10)/(3-19), (S10)/(3-21), (S10)/(3-22), (S10)/(3-23), (S10)/(3-24);
(S10)/(4-1), (S10)/(4-2);
(S10)/(5-1), (S10)/(5-3);
(S10)/(6-2), (S10)/(6-5), (S10)/(6-6), (S10)/(6-7), (S10)/(6-8), (S10)/(6-9), (S10)/(6-10), (S10)/(6-11), (S10)/(6-14), (S10)/(6-16);
(S10)/(7-1), (S10)/(7-2), (S10)/(7-4), (S10)/(7-5), (S10)/(7-6);
(S10)/(8-1), (S10)/(8-2), (S10)/(8-3), (S10)/(8-4), (S10)/(8-5);
(S10)/(9-1), (S10)/(9-2), (S10)/(9-3);
(S10)/(10-1), (S10)/(10-3);
(S10)/(11-1), (S10)/(11-2), (S10)/(11-3), (S10)/(11-4);
(S10)/(12-2), (S10)/(12-3), (S10)/(12-4), (S10)/(12-5);
(S10)/(13-1), (S10)/(13-2), (S10)/(13-3);
(S10)/(14-1), (S10)/(14-2), (S10)/(14-3);
(S10)/(15-4), (10)/(15-5);
(S10)/(16-2);
(S10)/(17-1), (S10)/(17-2);
(S10)/(19-1), (S10)/(19-2), (S10)/(19-3), (S10)/(19-5), (S10)/(19-6), (S10)/(19-7),
(S10)/(19-9), (S10)/(19-10), (S10)/(19-13);
(S10)/(20-1), (S10)/(20-2);
(S10)/(22-1), (S10)/(22-2);
(S10)/(23-1), (S10)/(23-2), (S10)/(23-3);
(S10)/(24-1), (S10)/(24-3), (S10)/(24-7);

11. Combinations of the compound (I-e-5) (S11) with particularly preferred fungicidally active compounds of groups 2 to 24:
(S11)/(2-1), (S11)/(2-2), (S11)/(2-3), (S11)/(2-4), (S11)/(2-5), (S11)/(2-6), (S11)/(2-8), (S11)/(2-9), (S11)/(2-10), (S11)/(2-11), (S11)/(2-12), (S11)/(2-13);
(S11)/(3-3), (S11)/(3-4), (S11)/(3-6), (S11)/(3-7), (S11)/(3-8), (S11)/(3-9), (S11)/(3-10), (S11)/(3-12), (S11)/(3-13), (S11)/(3-15), (S11)/(3.16), (S11)/(3-17), (S11)/(3-19), (S11)/(3-21), (S11)/(3-22), (S1)/(3-23), (S11)/(3-24);
(S11)/(4-1), (S11)/(4-2);
(S11)/(5-1), (S11)/(5-3);
(S11)/(6-2), (S11)/(6-5), (S11)/(6-6), (S11)/(6-7), (S11)/(6-8), (S11)/(6-9), (S11)/(6-10), (S11)/(6-11), (S11)/(6-14), (S11)/(6-16);
(S11)/(7-1), (S11)/(7-2), (S11)/(7-4), (S11)/(7-5), (S11)/(7-6);
(S11)/(8-1), (S11)/(8-2), (S11)(8-3), (S11)/(8-4), (S11)/(8-5);
(S11)/(9-1), (S11)/(9-2), (S11)/(9-3);
(S11)/(10-1), (S11)/(10-3);
(S11)/(11-1), (S11)/(11-2), (S11)/(11-3), (S11)/(11-4);
(S11)/(12-2), (S11)/(12-3), (S11)/(12-4), (S11)/(12-5);
(S11)/(13-1), (S11)/(13-2), (S11)/(13-3);
(S11)/(14-1), (S11)/(14-2), (S11)/(14-3);
(S11)/(15-4), (S11)/(15-5);
(S11)/(16-2);
(S11)/(17-1), (S11)/(17-2);
(S11)/(19-1), (S11)/(19-2), (S11)/(19-3), (S11)/(19-5), (S11)/(19-6), (S11)/(19-7), (S11)/(19-9), (S11)/(19-10), (S11)/(19-13);
(S11)/(20-1), (S11)/(20-2);
(S11)/(22-1), (S11)/(22-2);
(S11)/(23-1), (S11)/(23-2), (S11)/(23-3);
(S11)/(24-1), (S11)/(24-3), (S11)/(24-7);

Particular preference is furthermore given to combinations of safeners, in particular the compounds (S1) to S11), and systemic fungicides, in particular those from groups 2 to 24.

In addition to a safener, the combinations according to the invention comprise at least one active compound from the compounds of groups (2) to (24).

As such or in their formulations, the combinations according to the invention can also be used as a mixture with further known fungicides, preferably from groups 1 to 24, bactericides, acaricides, nematicides or insecticides—in particular when treating seed—to broaden the activity spectrum or to prevent the development of resistance, for example.

Preference is given, for example, to combinations of safeners, in particular the compounds (S1) to (S11), and the following fungicide combinations:
prothioconazole and fluoxastrobin,
prothioconazole and trifloxystrobin,
prothioconazole and spiroxamine,
prothioconazole and tebuconazole,
prothioconazole and prochloraz,
fluoxastrobin and trifloxystrobin, fluoxastrobin and spiroxamine,
fluoxastrobin and tebunconazole,
fluoxastrobin and prochloraz,
trifloxystrobin and spiroxamine
trifloxystrobin and tebuconazole
trifloxystrobin and prochloraz,
spiroxamine and tebuconazole,
spiroxamine and prochloraz,
tebucanozole and prochloraz.

Preference is furthermore given to the following combinations:

mefenpyr-diethyl and prothioconazole,
mefenpyr-diethyl and fluoxastrobin,
mefenpyr-diethyl and trifloxystrobin,
mefenpyr-diethyl and spiroxamine,
mefenpyr-diethyl and tebuconazole,
mefenpyr-diethyl and prochloraz, in each case in combination with a further compound from 2 to 24.

A mixture with other known active compounds, such as herbicides, or with fertilizers and growth regulators is also possible.

If the safeners and fungicides in the active compound combinations according to the invention are present in particular weight ratios, the activity-enhancing (synergistic) effect is particularly pronounced. However, the weight ratios of the active compounds in the active compound combinations can be varied within a relatively wide range. In general, the combinations according to the invention comprise safener and a fungicide from one of groups (2) to (24) in the mixing ratios given in an exemplary manner in the table below.

The mixing ratios are based on weight ratios. The ratio is to be understood as meaning active compound of formula (I): mixing partner.

TABLE 22

| Mixing partner | Mixing ratios<br>Preferred mixing ratio | Particularly preferred mixing ratio |
|---|---|---|
| Group (2): strobilurins | 50:1 to 1:50 | 10:1 to 1:20 |
| Group (3): triazoles without (3-15) | 50:1 to 1:50 | 20:1 to 1:20 |
| (3-15): prothioconazole | 50:1 to 1:50 | 10:1 to 1:20 |
| Group (4): sulphenamides | 1:1 to 1:150 | 1:1 to 1:100 |
| Group (5): valinamides | 50:1 to 1:50 | 10:1 to 1:20 |
| Group (6): carboxamides | 50:1 to 1:50 | 20:1 to 1:20 |
| Group (7): dithiocarbamates | 1:1 to 1:150 | 1:1 to 1:100 |
| Group (8): acylalanines | 10:1 to 1:150 | 5:1 to 1:100 |
| Group (9): anilino-pyrimidines | 5:1 to 1:50 | 1:1 to 1:20 |
| Group (10): benzimidazoles | 10:1 to 1:50 | 5:1 to 1:20 |
| Group (11): carbamates without (11-1) | 1:1 to 1:150 | 1:1 to 1:100 |
| (11-1): diethofencarb | 50:1 to 1:50 | 10:1 to 1:20 |
| Group (12): (12-1)/(12-2)/12-3) | 1:1 to 1:150 | 1:5 to 1:100 |
| Group (12): (12-4)/(12-5)/12-6) | 5:1 to 1:50 | 1:1 to 1:20 |
| Group (13): guanidines | 100:1 to 1:150 | 20:1 to 1:100 |
| Group (14): imidazoles | 50:1 to 1:50 | 10:1 to 1:20 |
| Group (15): morpholines | 50:1 to 1:50 | 10:1 to 1:20 |
| Group (16): pyrroles | 50:1 to 1:50 | 10:1 to 1:20 |
| Group (17): phosphonates | 10:1 to 1:150 | 1:1 to 1:100 |
| Group (18): phenylethanamides | 50:1 to 1:50 | 10:1 to 1:20 |
| (19-1): acibenzolar-S-methyl | 50:1 to 1:50 | 20:1 to 1:20 |
| (19-2): chlorothalonil | 1:1 to 1:150 | 1:1 to 1:100 |
| (19-3): cymoxanil | 10:1 to 1:50 | 5:1 to 1:20 |
| (19-4): edifenphos | 10:1 to 1:50 | 5:1 to 1:20 |
| (19-5): famoxadone | 50:1 to 1:50 | 10:1 to 1:20 |
| (19-6): fluazinam | 50:1 to 1:50 | 10:1 to 1:20 |
| (19-7): copper oxychloride | 1:1 to 1:150 | 1:5 to 1:100 |
| (19-8): copper hydroxide | 1:1 to 1:150 | 1:5 to 1:100 |
| (19-9): oxadixyl | 10:1 to 1:150 | 5:1 to 1:100 |

TABLE 22-continued

| Mixing partner | Mixing ratios<br>Preferred mixing ratio | Particularly preferred mixing ratio |
|---|---|---|
| (19-10): spiroxamine | 50:1 to 1:50 | 10:1 to 1:20 |
| (19-11) dithianon | 50:1 to 1:50 | 10:1 to 1:20 |
| (19-12) metrafenone | 50:1 to 1:50 | 10:1 to 1:20 |
| (19-13) fenamidone | 50:1 to 1:50 | 10:1 to 1:20 |
| (19-14): 2,3-dibutyl-6-chlorothieno-[2,3-d]pyrimidin-4(3H)one | 50:1 to 1:50 | 10:1 to 1:20 |
| (19-15): probenazole | 10:1 to 1:150 | 5:1 to 1:100 |
| (19-16): isoprothiolane | 10:1 to 1:150 | 5:1 to 1:100 |
| (19-17): kasugamycin | 50:1 to 1:50 | 10:1 to 1:20 |
| (19-18): phthalide | 10:1 to 1:150 | 5:1 to 1:100 |
| (19-19): ferimzone | 50:1 to 1:50 | 10:1 to 1:20 |
| (19-20): tricyclazole | 50:1 to 1:50 | 10:1 to 1:20 |
| (19-21): N-({4-[(cyclopropylamino)-carbonyl]phenyl}sulphonyl)-2-methoxybenzamide | 10:1 to 1:150 | 5:1 to 1:100 |
| Group (20): (thio)urea derivatives | 50:1 to 1:50 | 10:1 to 1:20 |
| Group (21): amides | 50:1 to 1:50 | 10:1 to 1:20 |
| Group (22): triazolopyrimidines | 50:1 to 1:50 | 10:1 to 1:20 |
| Group (23): iodochromone | 50:1 to 1:50 | 10:1 to 1:20 |
| Group (24): biphenylcarboxamides | 50:1 to 1:50 | 10:1 to 1:20 |

In each case, the mixing ratio is to be chosen such that a synergistic mixture is obtained. The mixing ratios of safener and a compound from one of groups (2) to (24) may also vary between the individual compounds of a group.

The compounds of group 1 and of groups 2 to 24 can be applied simultaneously, that is jointly or separately, or in succession, the sequence in the case of separate application generally not having any effect on the control results.

The combinations according to the invention have very good fungicidal properties and can be used for controlling phytopathogenic fungi, such as plasmodiophoromycetes, oomycetes, chytridiomycetes, zygomycetes, ascomycetes, basidiomycetes, deuteromycetes etc.

The combinations according to the invention are particularly suitable for controlling *Erysiphe graminis, Pyrenophora teres* and *Leptosphaeria nodorum.*

Some pathogens causing fungal and bacterial diseases which come under the generic names listed above may be mentioned as examples, but not by way of limitation:

*Xanthomonas* species, such as, for example, *Xanthomonas campestris* pv. *oryzae;*

*Pseudomonas* species, such as, for example, *Pseudomonas syringae* pv. *lachrymans;*

*Erwinia* species, such as, for example, *Erwinia amylovora;*

Diseases caused by powdery mildew pathogens, such as, for example,

*Blumeria* species, such as, for example, *Blumeria graminis;*

*Podosphaera* species, such as, for example, *Podosphaera leucotricha;*

*Sphaerotheca* species, such as, for example, *Sphaerotheca fuliginea;*

*Uncinula* species, such as, for example, *Uncinula necator;*

Diseases caused by rust disease pathogens, such as, for example,

*Gymnosporangium* species, such as, for example, *Gymnosporangium sabinae*

*Hemileia* species, such as, for example, *Hemileia vastatrix;*

*Phakopsora* species, such as, for example, *Phakopsora pachyrhizi* and *Phakopsora meibomiae;*

*Puccinia* species, such as, for example, *Puccinia recondita;*

*Uromyces* species, such as, for example, *Uromyces appendiculatus;*

Diseases caused by pathogens from the group of the Oomycetes, such as, for example,

*Bremia* species, such as, for example, *Bremia lactucae;*

*Peronospora* species, such as, for example, *Peronospora pisi* or *P. brassicae;*

*Phytophthora* species, such as, for example *Phytophthora infestans;*

*Plasmopara* species, such as, for example, *Plasmopara viticola;*

*Pseudoperonospora* species, such as, for example, *Pseudoperonospora humuli* or *Pseudoperonospora cubensis;*

*Pythium* species, such as, for example, *Pythium ultimum;*

Leaf blotch diseases and leaf wilt diseases caused, for example, by

*Alternaria* species, such as, for example, *Alternaria solani;*

*Cercospora* species, such as, for example, *Cercospora beticola;*

*Cladiosporum* species, such as, for example, *Cladiosporium cucumerinum;*

*Cochliobolus* species, such as, for example, *Cochliobolus sativus* (conidia form: Drechslera, Syn: *Helminthosporium*);

*Colletotrichum* species, such as, for example, *Colletotrichum lindemuthanium;*

*Cycloconium* species, such as, for example, *Cycloconium oleaginum;*

*Diaporthe* species, such as, for example, *Diaporthe citri;*

*Elsinoe* species, such as, for example, *Elsinoe fawcettii;*

*Gloeosporium* species, such as, for example, *Gloeosporium lacticolor;*

*Glomerella* species, such as, for example, *Glomerella cingulata;*

*Guignardia* species, such as, for example, *Guignardia bidwelli;*

*Leptosphaeria* species, such as, for example, *Leptosphaeria maculans;*

*Magnaporthe* species, such as, for example, *Magnaporthe grisea;*

*Mycosphaerella* species, such as, for example, *Mycosphaerella graminicola;*

*Phaeosphaeria* species, such as, for example, *Phaeosphaeria nodorum;*

*Pyrenophora* species, such as, for example, *Pyrenophora teres;*

*Ramularia* species, such as, for example, *Ramularia collo-cygni;*

*Rhynchosporium* species, such as, for example, *Rhynchosporium secalis;*

*Septoria* species, such as, for example, *Septoria apii;*

*Typhula* species, such as, for example, *Typhula incarnata;*

*Venturia* species, such as, for example, *Venturia inaequalis;*

Root and stem diseases caused, for example, by

*Corticium* species, such as, for example, *Corticium graminearum;*

*Fusarium* species, such as, for example, *Fusarium oxysporum;*

*Gaeumannomyces* species, such as, for example, *Gaeumannomyces graminis;*

*Rhizoctonia* species, such as, for example *Rhizoctonia solani;*

*Tapesia* species, such as, for example, *Tapesia acuformis;*

*Thielaviopsis* species, such as, for example, *Thielaviopsis basicola;*

Ear and panicle diseases (including maize crops) caused, for example, by

*Alternaria* species, such as, for example, *Alternaria* spp.;

*Aspergillus* species, such as, for example, *Aspergillus flavus;*

*Cladosporium* species, such as, for example, *Cladosporium* spp.;

*Claviceps* species, such as, for example, *Claviceps purpurea;*

*Fusarium* species, such as, for example, *Fusarium culmorum;*

*Gibberella* species, such as, for example, *Gibberella zeae;*

*Monographella* species, such as, for example, *Monographella nivalis;*

Diseases caused by smut fungi, such as, for example,

*Sphacelotheca* species, such as, for example, *Sphacelotheca reiliana;*

*Tilletia* species, such as, for example, *Tilletia caries;*

*Urocystis* species, such as, for example, *Urocystis occulta;*

*Ustilago* species, such as, for example, *Ustilago nuda;*

Fruit rot caused, for example, by

*Aspergillus* species, such as, for example, *Aspergillus flavus;*

*Botrytis* species, such as, for example, *Botrytis cinerea;*

*Penicillium* species, such as, for example, *Penicillium expansum;*

*Sclerotinia* species, such as, for example, *Sclerotinia selerotiorum;*

*Verticilium* species, such as, for example, *Verticilium alboatrum;*

Seed- and soil-borne rot and wilt diseases, and also diseases of seedlings, caused, for example, by

*Fusarium* species, such as, for example, *Fusarium culmorum;*

*Phytophthora* species, such as, for example, *Phytophthora cactrum;*

*Pythium* species, such as, for example, *Pythium ultimum;*

*Rhizoctonia* species, such as, for example, *Rhizoctonia solani;*

*Sclerotium* species, such as, for example, *Sclerotium rolfsii;*

Cancerous diseases, galls and witches' broom caused, for example, by

*Nectria* species, such as, for example, *Nectria galligena;*

Wilt diseases caused, for example, by

*Monilinia* species, such as, for example, *Monilinia laxa;*

Deformations of leaves, flowers and fruits caused, for example, by

*Taphrina* species, such as, for example, *Taphrina deformans;*

Degenerative diseases of woody plants caused, for example, by

*Esca* species, such as, for example, *Phaemoniella clamydospora;*

Diseases of flowers and seeds caused, for example, by

*Botrytis* species, such as, for example, *Botrytis cinerea;*

Diseases of plant tubers caused, for example, by

*Rhizoctonia* species, such as, for example, *Rhizoctonia solani.*

The fact that the combination is well tolerated by plants at the concentrations required for controlling plant diseases permits a treatment of entire plants (above-ground parts of plants and roots), of propagation stock and seed, and of the soil. The combinations according to the invention can be used for foliar application or else as seed dressings.

The fact that the combinations which can be used are well tolerated by plants at the concentrations required for controlling plant diseases permits a treatment of the seed. Accordingly, the combinations according to the invention can be used as seed dressings.

A large part of the damage to crop plants which is caused by phytopathogenic fungi occurs as early as when the seed is attacked during storage and after the seed is introduced into the soil, as well as during and immediately after germination of the plants. This phase is particularly critical since the roots and shoots of the growing plant are particularly sensitive and even minor damage can lead to the death of the whole plant. Protecting the seed and the germinating plant by the use of suitable compositions is therefore of particularly greet interest.

The control of phytopathogenic fungi which damage plants post-emergence is carried out primarily by treating the soil and the above-ground parts of plants with crop protection agents. Owing to the concerns regarding a possible impact of crop protection agents on the environment and the health of man and animals, there are efforts to reduce the amount of active compounds applied.

The control of phytopathogenic fungi by treating the seeds of plants has been known for a long time and is subject-matter of continuous improvements. However, the treatment of seed frequently entails a series of problems which cannot always be solved in a satisfactory manner. Thus, it is desirable to develop methods for protecting the seed and the germinating plant which dispense with the additional application of crop protection agents after sowing or after the emergence of the plants or where additional application is at least reduced. It is furthermore desirable to optimize the amount of active compound employed in such a way as to provide maximum protection for the seed and the germinating plant from attack by phytopathogenic fungi, but without damaging the plant itself by the active compound employed. In particular, methods for the treatment of seed should also take into consideration the intrinsic fungicidal properties of transgenic plants in order to achieve optimum protection of the seed and the germinating plant with a minimum of crop protection agents being employed.

The present invention therefore in particular also relates to a method for the protection of seed and germinating plants from attack by phytopathogenic fungi, by treating the seed with a combination according to the invention.

The invention likewise relates to the use of the combination according to the invention for the treatment of seed for protecting the seed and the germinating plant from phytopathogenic fungi.

Furthermore, the invention relates to seed which has been treated, in particular coated, with a combination according to the invention so as to afford protection from phytopathogenic fungi.

One of the advantages of the present invention is that, when systemic fungicides are used, treatment of the seed with the combinations according to the invention not only protects the seed itself, but also the resulting plants after emergence, from phytopathogenic fungi. In this manner, the immediate treatment of the crop at the time of sowing or shortly thereafter can be dispensed with.

Furthermore, it must be considered as advantageous that the combinations according to the invention can also be employed in particular in transgenic seed.

The combinations according to the invention are suitable for protecting seed of any plant variety which is employed in agriculture, in the greenhouse, in forests or in horticulture. In particular, this takes the form of seed of cereals (such as wheat, barley, rye, millet and oats), maize, cotton, soya beans, rice, potatoes, sunflowers, beans, coffee, beet (for example sugar beet and fodder beet), peanuts, vegetables (such as tomatoes, cucumbers, onions and lettuce), lawn and ornamental plants. The treatment of seed of cereals (such as wheat, barley, rye and oats), maize and rice is of particular importance.

In the context of the present invention, the combination according to the invention is applied to the seed either alone or in a suitable formulation. Preferably, the seed is treated in a state which is stable enough to avoid damage during treatment. In general, the seed may be treated at any point in time between harvest and sowing. The seed usually used has been separated from the plant and freed from cobs, shells, stalks, coats, hairs or the flesh of the fruits. Thus, for example, it is possible to use seed which has been harvested, cleaned and dried to a moisture content of below 15% by weight. Alternatively, it is also possible to use seed which, after drying, has, for example, been treated with water and then dried again.

When treating the seed, care must generally be taken that the amount of the combination according to the invention applied to the seed and/or the amount of further additives is chosen in such a way that the germination of the seed is not adversely affected, or that the resulting plant is not damaged. This must be borne in mind in particular in the case of active compounds which may have phytotoxic effects at certain application rates.

The combinations according to the invention can be applied directly, that is to say without comprising further components and without having been diluted. In general, it is preferable to apply the composition to the seed in the form of a suitable formulation. Suitable formulations and methods for the treatment of seed are known to the skilled worker and are described, for example, in the following documents: U.S. Pat. Nos. 4,272,417, 4,245,432, 4,808,430, 5,876,739, US 2003/0176428 A1, WO 2002/080675 A1, WO 2002/028186 A2.

The combinations according to the invention are also suitable for increasing the yield of crops. In addition, they show reduced toxicity and are well tolerated by plants.

According to the invention, it is possible to treat all plants and parts of plants. Plants are to be understood here as meaning all plants and plant populations, such as desired and undesired wild plants or crop plants (including naturally occurring crop plants). Crop plants can be plants which can be obtained by conventional breeding and optimization methods or by biotechnological and genetic engineering methods or combinations of these methods, including the transgenic plants and including plant cultivars which can or cannot be protected by plant breeders' certificates. Parts of plants are to be understood as meaning all above-ground and below-ground parts and organs of plants, such as shoot, leaf, flower and root, examples which may be mentioned being leaves, needles, stems, trunks, flowers, fruit-bodies, fruits and seeds and also roots, tubers and rhizomes. Parts of plants also include harvested material and vegetative and generative propagation material, for example seedlings, tubers, rhizomes, cuttings and seeds.

The treatment of the plants and parts of plants according to the invention with the active compounds is carried out directly or by action on their environment, habitat or storage area according to customary treatment methods, for example by dipping, spraying, evaporating, atomizing, broadcasting, brushing-on and, in the case of propagation material, in particular in the case of seeds, furthermore by one- or multilayer coating.

As already mentioned above, it is possible to treat all plants and their parts according to the invention. In a preferred embodiment, wild plant species and plant cultivars, or those obtained by conventional biological breeding, such as crossing or protoplast fusion, and parts thereof, are treated. In a further preferred embodiment, transgenic plants and plant cultivars obtained by genetic engineering, if appropriate in combination with conventional methods (Genetically Modified Organisms), and parts thereof, are treated. The term “parts” or “parts of plants” or “plant parts” has been explained above.

Particularly preferably, plants of the plant cultivars which are in each case commercially available or in use are treated according to the invention.

Depending on the plant species or plant cultivars, their location and growth conditions (soils, climate, vegetation period, diet), the treatment according to the invention may also result in superadditive (“synergistic”) effects. Thus, for example, reduced application rates and/or a widening of the activity spectrum and/or an increase in the activity of the substances and compositions which can be used according to the invention, better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products are possible which exceed the effects which were actually to be expected.

The transgenic plants or plant cultivars (i.e. those obtained by genetic engineering) which are preferably to be treated according to the invention include all plants which, in the genetic modification, received genetic material which imparted particularly advantageous useful properties (“traits”) to these plants. Examples of such properties are better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products. Further and particularly emphasized examples of such properties are a better defence of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, cotton, oilseed rape and also fruit plants (with the fruits apples, pears, citrus fruits and grapes), and particular emphasis is given to maize, soya beans, potatoes, cotton and oilseed rape. Traits that are emphasized are in particular increased defence of the plants against insects, by toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF and also combinations thereof) (hereinbelow referred to as “Bt plants”). Traits that are furthermore particularly emphasized are the increased tolerance of the plants to certain herbicidally active compounds, for example imidazolinones, sulphonylureas, glyphosate or phosphinotricin (for example the “PAT” gene). The genes which impart the desired traits in question can also be present in combination with one another m the transgenic plants. Examples of “Bt plants” which may be mentioned are maize varieties, cotton varieties, soya bean varieties and potato varieties which are sold under the trade names YIELD GARD® (for example maize, cotton, soya beans), KnockOut® (for example maize), Bollgard® (cotton), Nucotn® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinotricin, for example oilseed rape), IMI® (tolerance to imidazolinones) and STS4® (tolerance to sulphonylureas, for example maize). Herbicide-resistant plants (plants bred in a conventional manner for herbicide tolerance) which may be mentioned also include the varieties sold under the name Clearfield® (for example maize). Of course, these statements also apply to plant cultivars which have these genetic traits or genetic traits still to be developed, and which will be developed and/or marketed in the future.

Depending on their particular physical and/or chemical properties, the combinations according to the invention can be converted into the customary formulations, such as solutions, emulsions, suspensions, powders, dusts, foams, pastes, soluble powders, granules, aerosols, suspoemulsion concentrates, natural and synthetic materials impregnated with active compound and microencapsulations in polymeric substances and in coating compositions for seeds, and ULV cool and warm fogging formulations.

These formulations are produced in a known manner, for example by mixing the active compounds or active compound combinations with extenders, that is liquid solvents, liquefied gases under pressure, and/or solid carriers, optionally with the use of surfactants, that is emulsifiers and/or dispersants, and/or foam formers.

If the extender used is water, it is also possible to employ, for example, organic solvents as auxiliary solvents. Essentially, suitable liquid solvents are: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, or else water.

Liquefied gaseous extenders or carriers are to be understood as meaning liquids which are gaseous at standard temperature and under atmospheric pressure, for example aerosol propellants such as butane, propane, nitrogen and carbon dioxide.

Suitable solid carriers are: for example ammonium salts and ground natural minerals such as kaolins, clays, talc, chalk, quartz, attapulgite, montmorillonite or diatomaceous earth, and ground synthetic minerals such as finely divided silica, alumina and silicates. Suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks. Suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates.

Suitable dispersants are: for example lignosulphite waste liquors and methylcellulose.

Tackifiers such as carboxymethylcellulose, natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other possible additives are mineral and vegetable oils.

It is possible to use colorants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The active compound content of the use forms prepared from the commercial formulations may be varied within wide ranges. The concentration of active compound of the use forms for controlling animal pests, such as insects and acarids, may be from 0.0000001 to 95% by weight of active compound and is preferably from 0.0001 to 1% by weight. Application is in a manner adapted to the use forms.

The formulations for controlling unwanted phytopathogenic fungi generally comprise between 0.1 and 95% by weight of active compounds, preferably between 0.5 and 90%.

The combinations according to the invention can be used as such, in the form of their formulations or as the use forms prepared therefrom, such as ready-to-use solutions, emulsifiable concentrates, emulsions, suspensions, wettable powders, soluble powders, dusts and granules. They are used in a customary manner, for example by watering (drenching), drip irrigation, spraying, atomizing, broadcasting, dusting, foaming, spreading-on, and as a powder for dry seed treatment, a solution for seed treatment, a water-soluble powder for seed treatment, a water-soluble powder for slurry treatment, or by encrusting etc.

The combinations according to the invention can, in commercial formulations and in the use forms prepared from these formulations, be present as a mixture with other active compounds, such as insecticides, attractants, sterilants, bactericides, acaricides, nematicides, fungicides, growth regulators or herbicides.

The combinations according to the invention can be applied simultaneously, that is jointly or separately, or in succession, the sequence in the case of separate application generally not having any effect on the control results. In a preferred embodiment, the combination according to the invention is applied simultaneously, preferably jointly.

In a further preferred embodiment, the combination according to the invention is applied in succession.

When using the active compound combinations according to the invention, the application rates can be varied within a relatively wide range, depending on the kind of application. In the treatment of parts of plants, the application rates of active compound combination are generally between 0.1 and 10 000 g/ha, preferably between 10 and 1000 g/ha. In the treatment of seed, the application rates of active compound combination are generally between 0.001 and 50 g per kilogram of seed, preferably between 0.01 and 10 g per kilogram of seed. In the treatment of the soil, the application rates of active compound combination are generally between 0.1 and 10 000 g/ha, preferably between 1 and 5000 g/ha.

The combinations can be used as such, in the form of concentrates or in the form of generally customary formulations, such as powders, granules, solutions, suspensions, emulsions or pastes.

The formulations mentioned can be prepared in a manner known per se, for example by mixing the active compounds with at least one solvent or diluent, emulsifier, dispersant and/or binder or fixative, water repellent, if desired desiccants and UV stabilizers, and, if desired, colorants and pigments and other processing auxiliaries.

Accordingly, the invention also provides a fungicidal composition comprising one or more safeners of group 1 and one or more fungicides of groups 2 to 24, except for the following safener/fungicidal combinations:

daimuron and metominostrobin, oxabetrinil and metalaxyl,

N-methylsulphonyloxyphenyl-N-methylthiolcarbamate and kasugamycin.

Preferably, the fungicidal composition according to the invention comprises one or more of the safeners from group 1 mentioned as being preferred and one or more of the fungicides from groups 2 to 24 mentioned as being preferred.

Particularly preferably, the fungicidal composition according to the invention comprises one or more of the safeners from group 1 mentioned as being particularly preferred and one or more of the fungicides from groups 2 to 24 mentioned as being particularly preferred.

Very particularly preferably, the fungicidal composition according to the invention comprises one or more of the safeners from group 1 mentioned as being very particularly preferred and one or more of the fungicides from groups 2 to 24 mentioned as being very particularly preferred.

Especially preferred are fungicidal compositions according to the invention comprising one of the especially preferred combinations of safener and fungicide.

The good fungicidal action of the combinations according to the invention is demonstrated by the examples below. While the individual active compounds show weaknesses in their fungicidal action, the combinations show an action which exceeds a simple sum of actions, although the safeners used according to the invention generally do not have any fungicidal action.

A synergistic effect in the fungicides is always present when the fungicidal action of the active compound combinations exceeds the total of the action of the active compounds when applied individually.

The expected fungicidal action for a given combination of two active compounds can be calculated as follows, according to S. R. Colby ("Calculating Synergistic and Antagonistic Responses of Herbicide Combinations", Weeds 1967, 15, 20-22):

If

X is the efficacy when employing active compound A at an application rate of m g/ha, Y is the efficacy when employing active compound B at an application rate of n g/ha and E is the efficacy when employing active compounds A and B at application rates of m and n g/ha, then $$E = X + Y - \frac{X \times Y}{100}$$

Here, the efficacy is determined in %. 0% means an efficacy which corresponds to that of the control, whereas an efficacy of 100% means that no infection is observed.

If the actual fungicidal action exceeds the calculated value, the action of the combination is superadditive, i.e. a synergistic effect is present. In this case, the actually observed efficacy must exceed the value calculated using the above formula for the expected efficacy (E).

The invention is illustrated by the examples below. However, the invention is not limited to the examples.

EXAMPLE

*Erysiphe* Test (Wheat)/Curative

To prepare a suitable preparation of active compound, a commercial formulation of active compound is diluted with water to the desired concentration.

To test for curative activity, young plants were dusted with spores of *Erysiphe graminis* f.sp. *tritici.* 48 hours after the inoculation, the plants were sprayed with the preparation of active compound at the stated application rates.

The plants were placed in a greenhouse at a temperature of about 20° C. and a relative atmospheric humidity of about 80% to promote the development of mildew pustules.

Evaluation was carried out 7 days after the inoculation. 0% means an efficacy which corresponds to that of the control, whereas an efficacy of 100% means that no infection is observed.

TABLE

*Erysiphe* test (wheat)/curative

| Active compounds | Active compound application rate in g/ha | efficacy in % found* | efficacy in % calc.** |
|---|---|---|---|
| Mefenpyr | 25 | 0 | |
| Trifloxystrobin | 125 | 86 | |
| Fluoxastrobin | 125 | 0 | |
| Spiroxamin | 125 | 0 | |
| Prothioconazole | 125 | 43 | |
| Tebuconazole | 125 | 57 | |
| Mefenpyr + Trifloxystrobin 1:5 | 25 + 125 | 100 | 86 |
| Mefenpyr + Fluoxastrobin 1:5 | 25 + 125 | 100 | 0 |
| Mefenpyr + Spiroxamin 1:5 | 25 + 125 | 86 | 0 |
| Mefenpyr + Prothioconazole 1:5 | 25 + 125 | 100 | 43 |
| Mefenpyr + Tebuconazole 1:5 | 25 + 125 | 100 | 57 |

*found = activity found

**calc. = activity calculated using Colby's formula

The invention claimed is:

1. A method of increasing the microbiocidal activity of a fungicide comprising treating a seed or a plant with the fungicide and a safener, wherein the safener is mefenpyr diethyl and wherein the fungicide is tebuconazole, wherein the mefenpyr diethyl and the tebuconazole are applied to the seed or plant in synergistic amounts, wherein the weight ratio of mefenpyr diethyl to tebuconazole is from 50:1 to 1:50.

2. The method according to claim 1 wherein the seed or the plant is treated with a composition comprising the fungicide and the safener.

3. The method according to claim 1 wherein the seed is treated with the fungicide and the safener.

4. The method according to claim 1 wherein the plant is treated with the fungicide and the safener.

5. The method according to claim 1 wherein the seed is in contact with the fungicide and the safener.

6. The method according to claim 1 wherein the plant is in contact with the fungicide and the safener.

7. The method according to claim 6 wherein the plant is a transgenic plant.

8. The method according to claim 1, wherein the weight ratio of mefenpyr diethyl to tebuconazole is 20:1 to 1:20.

9. A method of controlling phytopathogenic fungi comprising treating a seed or a plant with a fungicide and a safener, wherein the safener is mefenpyr diethyl and wherein the fungicide is tebuconazole, wherein the mefenpyr diethyl and the tebuconazole are applied to the seed or plant in synergistic amounts, wherein the weight ratio of mefenpyr diethyl to tebuconazole is from 50:1 to 1:50.

10. A method according to claim 9, wherein the fungi is plasmodiophoromycetes, oomycetes, chytridiomycetes, zygomycetes, ascomycetes, basidiomycetes, or deuteromycetes.

11. The method according to claim 9, wherein the fungi is Erysiphe graminis, Pyrenophora teres, or Leptosphaeria nodorum.

12. The method according to claim 1, wherein the plant treated is wheat.

13. The method according to claim 9, wherein the mefenpyr diethyl and the tebuconazole are applied to the seed or plant simultaneously.

14. The method according to claim 9, wherein the mefenpyr diethyl and the tebuconazole are applied to the seed or plant in succession.

15. The method according to claim 9, wherein the weight ratio of mefenpyr diethyl to tebuconazole is 20:1 to 1:20.

* * * * *